US010138510B2

(12) United States Patent
Clarke et al.

(10) Patent No.: US 10,138,510 B2
(45) Date of Patent: Nov. 27, 2018

(54) DUAL LABELING METHODS FOR MEASURING CELLULAR PROLIFERATION

(71) Applicant: LIFE TECHNOLOGIES CORPORATION, Carlsbad, CA (US)

(72) Inventors: Scott Clarke, Eugene, OR (US); Jolene Bradford, Eugene, OR (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 14/300,728

(22) Filed: Jun. 10, 2014

(65) Prior Publication Data

US 2016/0130637 A1  May 12, 2016

Related U.S. Application Data

(62) Division of application No. 12/993,079, filed as application No. PCT/US2009/044024 on May 14, 2009, now abandoned.

(60) Provisional application No. 61/054,102, filed on May 16, 2008.

(51) Int. Cl.
| C12Q 1/68 | (2018.01) |
|---|---|
| C12Q 1/6809 | (2018.01) |
| C12Q 1/6844 | (2018.01) |
| C12Q 1/6804 | (2018.01) |

(52) U.S. Cl.
CPC ......... *C12Q 1/6809* (2013.01); *C12Q 1/6804* (2013.01); *C12Q 1/6846* (2013.01)

(58) Field of Classification Search
None
See application file for complete search history.

(56) References Cited

U.S. PATENT DOCUMENTS

| 4,603,209 A | 7/1986 | Tsien et al. |
|---|---|---|
| 4,714,763 A | 12/1987 | Theodoropulos |
| 4,774,339 A | 9/1988 | Haugland et al. |
| 4,810,636 A | 3/1989 | Corey et al. |
| 4,849,362 A | 7/1989 | Demarinis et al. |
| 4,945,171 A | 7/1990 | Haugland et al. |
| 4,981,977 A | 1/1991 | Southwick et al. |
| 5,187,288 A | 2/1993 | Kang et al. |
| 5,227,487 A | 7/1993 | Haugland et al. |
| 5,248,782 A | 9/1993 | Haugland et al. |
| 5,268,486 A | 12/1993 | Waggoner et al. |
| 5,274,113 A | 12/1993 | Kang et al. |
| 5,433,896 A | 7/1995 | Kang et al. |
| 5,442,045 A | 8/1995 | Haugland et al. |
| 5,451,343 A | 9/1995 | Neckers et al. |
| 5,459,276 A | 10/1995 | Kuhn et al. |
| 5,486,616 A | 1/1996 | Waggoner et al. |
| 5,501,980 A | 3/1996 | Katerinopoulos et al. |
| 5,569,587 A | 10/1996 | Waggoner |
| 5,569,766 A | 10/1996 | Waggoner et al. |
| 5,627,027 A | 5/1997 | Waggoner |
| 5,696,157 A | 12/1997 | Wang et al. |
| 5,705,622 A | 1/1998 | McCapra |
| 5,798,276 A | 8/1998 | Haugland et al. |
| 5,800,996 A | 9/1998 | Lee et al. |
| 5,808,044 A | 9/1998 | Brush et al. |
| 5,830,912 A | 11/1998 | Gee et al. |
| 5,846,737 A | 12/1998 | Kang |
| 5,863,727 A | 1/1999 | Lee et al. |
| 5,874,532 A | 2/1999 | Pieken et al. |
| 5,877,310 A | 3/1999 | Reddington et al. |
| 5,945,526 A | 8/1999 | Lee et al. |
| 6,002,003 A | 12/1999 | Shen et al. |
| 6,004,536 A | 12/1999 | Leung et al. |
| 6,008,373 A | 12/1999 | Waggoner et al. |
| 6,043,025 A | 3/2000 | Minden et al. |
| 6,127,134 A | 10/2000 | Minden et al. |
| 6,130,094 A | 10/2000 | Waggoner et al. |
| 6,130,101 A | 10/2000 | Mao et al. |
| 6,133,445 A | 10/2000 | Waggoner et al. |
| 6,162,931 A | 12/2000 | Gee et al. |
| 6,229,055 B1 | 5/2001 | Klaubert et al. |
| 6,255,475 B1 | 7/2001 | Kwiatkowski |
| 6,339,392 B1 | 1/2002 | Ashihara et al. |
| 6,562,632 B1 | 5/2003 | Szalecki et al. |

(Continued)

FOREIGN PATENT DOCUMENTS

| EP | 1065250 | 12/2004 |
|---|---|---|
| WO | WO-89/02475 | 3/1989 |

(Continued)

OTHER PUBLICATIONS

"Invitrogen: "EdU", (5-ethynyl-2'deosyuridine), Cat. No. A100444"Oct. 6, 2008 (Oct. 6, 2008), XP007909962, 2008.
Agard, N. et al., "A Strain-Promoted [3+2]Azide-Alkyne Cycloaddition for Covalent Modification of Biomolecules in Living Systems", *J. Am. Chem Soc*, vol. 126(46), 2004, pp. 15046-15047.
Anonymous, , ""Telomerase PCR ELISA. For fast and sensitive detection of telomerase activity."", *Biochemica*, [Online] Jan. 1, 1996 (Jan. 1, 1996), pp. 7-8,, vol. 1996, No. 4,, 1996, 7-8.
Anonymous, , "TRAPeze telomerase detection kit. S770", XP7913582, 2005.
Antos, J. M. et al., "Transition metal catalyzed methods for site-selective protein modification", *Current Opinion in Chemical Biology*; vol. 10(3), Jun. 1, 2006, 253-262.

(Continued)

*Primary Examiner* — Addison D Ault

(57) ABSTRACT

The present invention provides a method for measuring cellular nascent nucleic acid synthesis by dual pulse labeling of nucleic acid. The first pulse labeling of nucleic acid with a nucleoside analog allows establishment of a baseline nucleic acid synthesis rate. Pulse labeling of the nucleic acid with a second nucleoside analog then allows measurement of any changes to nucleic acid synthesis. The nucleic acid synthesis can be measured as cell proliferation, DNA, or gene expression, RNA. This method does not require a potentially artifact-inducing intermediary wash step between pulse labels. Additionally, this method may be used to screen compounds for their affect on cellular proliferation by treating cells or an organism with the test compound simultaneous to or before treatment with a competitive nucleoside analog.

9 Claims, 49 Drawing Sheets

(56) References Cited

U.S. PATENT DOCUMENTS

| | | | |
|---|---|---|---|
| 6,716,979 | B2 | 4/2004 | Diwu et al. |
| 6,737,236 | B1 | 5/2004 | Pieken et al. |
| 6,849,745 | B2 | 2/2005 | Lee et al. |
| 6,967,250 | B1 | 11/2005 | Kumar et al. |
| 7,122,703 | B2 | 10/2006 | Saxon et al. |
| 7,169,939 | B2 | 1/2007 | Lee et al. |
| 7,256,034 | B2 | 8/2007 | Zahner |
| 7,375,234 | B2 | 5/2008 | Sharpless et al. |
| 7,427,678 | B2 | 9/2008 | Pieken et al. |
| 7,763,736 | B2 | 7/2010 | Sharpless |
| 2003/0171570 | A1 | 9/2003 | Schweitzer |
| 2003/0175728 | A1 | 9/2003 | Belousov |
| 2006/0110782 | A1 | 5/2006 | Bertozzi et al. |
| 2006/0147963 | A1 | 7/2006 | Barone |
| 2007/0037964 | A1 | 2/2007 | Saxon et al. |
| 2007/0099222 | A1 | 5/2007 | Gee et al. |
| 2007/0207476 | A1 | 9/2007 | Salic et al. |
| 2009/0215635 | A1 | 8/2009 | Carell et al. |
| 2011/0118142 | A1 | 5/2011 | Clarke et al. |

FOREIGN PATENT DOCUMENTS

| | | |
|---|---|---|
| WO | WO-96/09316 | 3/1996 |
| WO | WO-96/020289 | 7/1996 |
| WO | WO-96/34984 | 11/1996 |
| WO | WO1997/040104 | 10/1997 |
| WO | WO-98/30575 | 7/1998 |
| WO | WO-1999051702 | 10/1999 |
| WO | WO2001/021624 | 3/2001 |
| WO | WO2002/026891 | 4/2002 |
| WO | WO-2002/029003 | 4/2002 |
| WO | WO-03/101972 | 12/2003 |
| WO | WO-2004/018497 | 3/2004 |
| WO | WO-2006/038184 | 4/2006 |
| WO | WO-2006/116629 | 11/2006 |
| WO | WO-2006/117161 | 11/2006 |
| WO | WO2009/140541 | 11/2009 |
| WO | WO-2009/140541 A3 | 1/2010 |

OTHER PUBLICATIONS

Baskin, J et al., "Copper-free click chemistry for dynamic in vivo imaging", *PNAS*, vol. 104(43), 2007, pp. 16793-16797.

Berthod, T. et al., "Synthesis and Mass Spectrometry Analysis of Oligonucleotides Bearing 5-Formyl-2'-Deoxyuridine in Their Structure", *Nucleosides and Nucleotides*; 15:7-8, 1996, 1287-1305.

Beverloo, et al., "Immunochemical detection of proteins and nucleic acids on filters using small luminescent inorganic crystals as marker.", *Analytical Biochemistry*, 203, 1992, 326-34.

Buck, Suzanne B , ""Detection of S-phase cell cycle progression using 5-ethynyl-2", deoxyuridine incorporation with click chemistry an alternative to using 5-bromo-2'-deoxyuridine antibodies" *Biotechniques*, vol. 44, No. 7, Jun. 2008 (Jun. 2008), pp. 927-929, XP001537196, Bradford Jolene; Gee Kyle R; Agnew Brian J; Clarke Scott T; Salic Adrian:, 2008, 927-929.

Buff, R et al., "Z-DNA formation by 2'-C-ethynyl-modified oligonucleotides", *Synlett, no. Spec. Iss.*, 1999, 905-908.

Burley, Glenn et al., "Directed DNA Metallization", *J. Am. Chem. Soc.*, 128, 2006, 1398-1399.

Burley, Glenn et al., "New labelling strategies for the sensitive detection of nucleic acids", *Chemistry of Nucleic Acid Components ACAD Sci Czech Republic, Inst Organic Chem & Biochem*, Flemingovoniam 2, Prague 166106, *Czech Republic Series: Collection Symposium Series*, SP008068569 & *13th Symposium on Chemistry Nucleic Acid Components*: Spinderuv Mly, 2005, 229-232.

Burns, Kevin A et al., ""Low doses of bromo- and iododeoxyuridine produce near-saturation labeling of adult proliferat ive populations i n the dentate gyrus"", *European Journal of Neuroscience* , Oxforduniversity Press,GB , vol. 21, No. 3, Feb. 1, 2005 (Feb. 1, 2005) , pp. 803-807, XP009123437, Kuan Chia-Yi, 2005, 803-807.

Byun, Youngjoo et al., "Synthesis and Biological Evaluation of Neutral and Zwitterionic 3-Carboranyl Thymidine Analogues for Boron Neutron Capture Therapy", *M. Med. Chem.*, 48, 2005, 1188-1198.

Caburet, S et al., "Coming the genome for genomic instability", *Trends in Biotechnology*, Elsevier Publications, Cambridge, GB, vol. 20, No. 8, Aug. 1, 2002 (2002 pp. 344-350, XP004371920, 2002, 344-350.

Cappella, et al., "A novel method based on click chemistry, which overcomes limitations of cell cycle analysis by classical determination of BrdU incorporation,allowing multiplex antibody staining", *Cytometry. Part A*, John Wiley &Sons, Inc, US, [Online] vol. 73, No. 7, Jul. 1, 2008 (Jul. 1, 2008), pp. 626-636, XP009123406, Paolo; Gasparri Fabio; Pulicimaurizio; Moll Juergen: , 2008, 626-636.

Chien, Wei-Ming et al., "Alternative Fates of Keratinocytes Transduced by Human Papillomavirus Type 18 E7 during Squamous Differentiation", *J Virol*, vol. 76, No. 6, DOIL 10.1128/JVI.76.6.2964-2972. 2002, 2002, 2964-2972.

Clarke, Scott T , ""Click catalyzed nucleic acid labeling as a novel replacement for the BrdU antibody based cell proliferation assay"", *FASEB Journal, Fed. of American Soc. For Experimental Biology*, Bethesda, MD, US, vol. 21, No. 5, Apr. 1, 2007 (Apr. 1, 2007), pp. A289-A290, XP009123420, Bradford Jolene A; Gee Kyle; Agnew Brian; Salic Adrian:, 2007, A289-A290.

Cozzarelli, Nicholas , "The Mechanism of Action of Inhibitors of DNA Synthesis", *Ann. Rev. Biochem.*, 46, 1977, 641-668.

Curtis, Maurice et al., "Increased cell proliferation and neurogenesis in the adult human Huntington's disease brain", *PNAS*, vol. 100, No. 15, 2003, 9023-9027.

Deiters, Alexander , "In vivo incorporation of an alkyne into proteins in *Escherichia coli*", *Bioorganic & Medicinal Chemistry Letters*; 15, 2005, 1521-1524.

Diermeier-Daucher, et al., ""Comparing the effect of the thymidine analogues EdU and BrdU on cell cycle progression"", *Cytometry. Part A*, John Wiley, Hoboken, NJ, US, vol. ?IA, No. 9, Sep. 1, 2007 (Sep. 1, 2007), pp. 766-767, XP009123426, Simone (Reprint); Clarke Scott; Bradford Jolene; Hill Dani; Brockhoff Gero:, 2007, 766-767.

Hassane, Fatouma S. et al., "Targeted Liposomes: Convenient coupling of ligands to preformed vesicles using click chemistry", *Bioconjugate Chemistry*,17(3), May 6-Jun. 6, 849-854.

Higashiya, Seiichiro et al., "A FAcile Synthesis of 2-Azidoadenosine Derivatives from Guanosine as Photoaffinity Probes", *Bioorganic & Medicinal Chemistry Letters*; vol. 6, No. 1, 1996, 39-42.

Hyde, Robyn et al., "Antiviral Amphipathic Oligo- and Polyribonucleotides: Analogue Development and Biological Studies", *J. Med. Chem.*, 46, 2003, 1878-1885.

Kagel, John et al., "A Chemical Model for the Fragmentation Reaction in Thymidylate Synthase Catalysis. Synthesis and Evaluation of a 5-Methylene-1-(1,2.3,4-tetrahydroquinolyl)-6-allyluridine", *J. Org. Chem.*, 58, 1993, 2738-2746.

Kolb, H. C. et al., "Click Chemistry: Diverse Chemical Function from a Few Good Reactions", *Angewandte Chemie International Edition in English*, 40, 2001, 2004-2021.

Kolb, Hartmuth C. et al., "The growing impact of click chemistry on drug discovery", *Drug Discovery Today*, vol. 8(24), 2003, pp. 1128-1137.

Langenhan, J. M. et al., "Recent Carbohydrate-based chemoeslective ligation applications", *Current organics systhesis*, 2(1), Jan. 2005, 59-81.

Lee, Lac et al., "A Potent and Highly Selective Inhibitor of Human alpha-1,3-Fucosyltransferase via Click Chemistry", *J. Am. Chem. Soc.*; 125, 2003, 9588-9589.

Lewis, W. G. et al., "Click chemistry in Situ: Acetylcholinesterase as a Reaction Vessel for the Selectivity Assembly of a Femtomolar Inhibitor from an Array of building Blocks", *Angewandte Chemie International Edition in English*, 41(6), 2002, 1053-1057.

Mar, Eng-Chun et al., "Some nucleoside analogs with anti-human immunodeficiency virus activity inhibit replication of Epstein-Barr virus", *Antiviral Research*, vol. 28, 1995, 1-11.

(56) References Cited

OTHER PUBLICATIONS

Marsh, Andrew et al., "The synthesis and properties of oligoribonucleotide-spermine conjugates", *Organic & Biomolecular Chemistry*; vol. 2, No. 14, 2004, 2103-2112.

Masata, M, "'Dynamics of repl ication fociin early S phase as visualized by cross-correlation function'", *Journal of Structural Biology*, Orlando, US, vol. 151, No. 1, Jul. 1, 2005 (Jul. 1, 2005), pp. 61-68, XP004949562, Malinsky J; Fidlerova H; Smirnov E; Raska I:, 2005, 61-68.

Minakawa, Noriaki et al., "A Versatile Modification of On-Column Oligodeoxynucleotides Using a Copper-Catalyzed Oxidative Acetylenic Coupling Reaction", *J. Am Chem. Soc.*; 125, 2003, 11545-11552.

Nam, Nguyen-Hai et al., "ATP-phosphopeptide conjugates as inhibitors of Src tyrosine kinases", *Bioorganic & Medicinal Chemistry*, 12, 2004, 5753-5766.

Nguyen, Hong-Khanh et al., "Studies Towards the Design of a Modified GC Base Pair with Stability Similar to that of the AT Base Pair", *Tetrahedron Letters*, vol. 38, No. 23, 1997, 4083-4086.

Okamoto, Kaoru et al., "Synthesis of ara-Cadeguomycin. 2-Amino-3,4-dihydro-4-oxo-7-(beta-D-arabinofuranosyl)-7H-pyrrolo[2,3-d]pyrimidine-5-carboxylic Acid", *Bull. Chem. Soc. Jpn.*, 59, 1986, 1915-1919.

PCT/US08/053870,, "International Preliminary Report on Patentability dated Jul. 31, 2008", Jul. 31, 2008.

PCT/US09/44024,, "International Preliminary Report on Patentability dated Nov. 25, 2010", 11.

PCT/US2008/053870,, "Search Report dated Jul. 31, 2008", International Application Serial No. PCT/US2008/053870,, P220, Jul. 31, 2008, 15 Pgs.

PCT/US2009/044024,, "International Search Report dated Nov. 5, 2009", 19 pgs.

Riggins, James et al., "Kinetic and Thermodynamic Analysis of the Hydrolytic Ring-Opening of the Malondialdehyde-Deoxyguanosine Adduct, 3-(2'-Deoxy-beta-D-erythro-pentofuranosyl)-pyrimido[1,2-alpha]purin-10(3H)-one", *J. Am. Chem. Soc.*; 126, 2004, 8237-8243.

Rodionov, V. et al., "Mechanism of the Ligand-Free Cu-Catalyzed Azide-Alkyne Cycloaddition Reaction", *Angew. Chem. Int. Ed.*, vol. 44, 2005, 2210-2215.

Rostovtsev, et al., "A step-wise Huisgen cycloaddition process copper (I) -catalyzed regioselective ligation of azides and terminal alkynes", *Angewandte Chemie. International Edition*, vol. 41, No. 14, 2002, 2596-2599.

Salic, Adrian et al., "'A chemical method for fast and sensitive detection of DNA synthesis in vivo'", *Proceedings of the National Academy of Sciences of USA*, National Academy of, Science, Washington, DC, US, [Online] vol. 105, No. 7, Feb. 19, 2008 (Feb. 19, 2008), pp. 2415-2420, XP009123400, 2008, 2415-2420.

Saxon, Eliana et al., "Cell Surface Engineering by a Modified Staudinger Reaction.", *Science*, vol. 287, No. 5460, Mar. 17, 2000, 2007-2010.

Seo, Tae S. et al., "Click Chemistry to Construct Fluorescent Oligonucleotides for DNA Sequencing", *J. Org. Chem.*, 68, 2003, 609-612.

Shimura, et al., "'DNA-PK Is Involved in Repairing a Transient Surge of DNA Breaks Induced by Deceleration of DNA Replication'", *Journal of Molecular Biology*, London, GB, vol. 367, No. 3, Mar. 3, 2007 (Mar. 3, 2007)pp. 665-680, XP005910827, Martin T; Torres MM; Gu MJ; Pluth C; Dibernardi J M; McDonald MA; Aladjem J S; MI:, 2007, 665-680.

Sivakumar, Krishnamoorthy et al., "A Fluorogenic 1,3-Dipolar Cycloaddition Reaction of 3-Azidocoumarins and Acetylenes", *Organic Letters*, vol. 6, No. 24, 2004, 4603-4606.

Speers, Anna E. et al., "Profiling Enzyme Activities in Vivo Using Click Chemistry Methods", *Chemistry & Biology*, vol. 11, Apr. 1, 2004, 535-546.

Stanek D,, "Non-i sot opi c.mappi ng of r ibosomal RNA synthesis and processing i n the nucleous .", *Chromosoma* Dec. 2001, vol. 110, No. 7, Dec. 2001 (Dec. 2001 pp. 460-470, XP009123496, Koberna K; Pliss A; Malinsky J; Masata M; Vecerova J; Risueno MC; Raska I:, 2001, 460-470.

Sunthankar, Prasanna et al., "Synthesis of 5-Azido-UDP-N-Acetylhexosamine Photoaffinity Analogs and Radiolabeled UDP-N-Acetylhexosamines", *Analytical Biochemistry*, vol. 258, No. 2, May 1, 1998, 195-201.

Tornoe, Christian et al., "Peptidotriazoles on Solid Phase: [1,2,3]-Triazoles by Regiospecific Copper(I)-Catalyzed 1,3-Dipolar Cycloadditions of Terminal Alkynes to Azides", *J. Org. Chem.*, 67, 2002, 3057-3064.

Trevisiol, Emmanuelle et al., "The Oxyamino-Aldehyde Coupling Reaction: An Efficient Method for the Derivatization of Oligonucleotides", *Tetrahedron Letters*, vol. 38, No. 50, 1997, 8687-8690.

Venyaminova, A.G. et al., "New Photoreactive mRNA Analogues for the Affinity Labeling of Ribosomes", *Nucleosides and Nucleotides*, 14:3-5, 1995, 1069-1072.

Wei-Ming, Chien, "'Alternative . fates of keratinocytestransduced by human papillomavirus type 18 E7 duri ng squamous differentiation'", *Journal of Virology, The American Society for Microbiology*, US, [Online], vol. 76, No. 6, Mar. 1, 2002 (Mar. 1, 2002), pp. 2964-2972, XP009123457, Noya Francisco; 1-2 ,6-9, Benedict-Hamilton Heather M,' Broker Thomas 13-15, R,' Chow Louise T:, 2002, 2964-2972.

Yu et al., "Synthesis of (E)-5-[2-(Tri-n-butylstannyl)vinyl] Substituted 2'-Deoxyuridine Derivatives for Use in Halogenation and Radiohalogenation Reactions", *Synlett*, No. 1, 2000, 86-88.

Merrick, C. et al., "Visualization of Altered Replication Dynamics after DNA Damage in Human Cells", *J. Biol. Chem.* 279, 2004, 20067-20075.

Karl, D. , "Measurement of Microbial Activity and Growth in the Ocean by Rates of Stable Ribonucleic Acid Synthesis", *Applied and Environmental Microbiology*, 1979, p. 850-860.

| Specimen Name: | Edu then BrdU incorp |
| Tube Name: | Edu then click+cycle |

| Population | %Parent |
|---|---|
| ☐ Q1 | 5.2 |
| ☐ Q2 | 36.2 |
| ☐ Q3 | 56.1 |
| ☐ Q4 | 2.5 |

FIG. 4B

DUAL LABELING METHODS FOR MEASURING CELLULAR PROLIFERATION

CROSS-REFERENCE TO RELATED APPLICATIONS

This application is a Division of U.S. application Ser. No. 12/993,079, filed Feb. 1, 2011, which is a national stage entry of PCT/US09/44024, filed May 14, 2009 and claims priority to U.S. application No. 61/054,102, filed May 16, 2008, which disclosures are herein incorporated by reference in their entirety.

FIELD OF THE INVENTION

The present disclosure relates to methods for the dual pulse labeling of nucleic acid.

DESCRIPTION OF RELATED ART

Pulse labeling cellular DNA for the purpose of determining the rate of growth is typically performed by the addition of a nucleic acid sugar analog (nucleoside) to the medium that a cell is grown in, or in the drinking water of the animal it is being fed to, or by injection in the animal which is being labeled. A timed exposure to a DNA analog with the potential of incorporation of that analog into the actively synthesized DNA is defined as a pulse. Standard methods for pulse labeling DNA include use of 5-bromo 2'-deoxyuridine (BrdU) or radioactively-labeled nucleoside analogs.

Methods for detecting BrdU-labeled DNA or radioactively-labeled DNA are well known in the art. For example, cells containing BrdU-labeled DNA may be treated with an anti-BrdU monoclonal antibody followed by a fluorescently-labeled secondary antibody. The fluorescent label may then be visualized and quantified by standard techniques, including plate assays, fluorescence microscopy, imaging, high content screening, or flow cytometry.

Dissecting complex cellular processes, including cell proliferation, requires the ability to track biomolecules as they function within their native habitat. In recent years, an alternative tool for tagging biomolecules has emerged from the chemical biology community—the bioorthogonal chemical reporter. The use of bioorthogonal reactive moieties has been described for the detection of metabolites and post-translational modifications using the azide moiety as a bioorthogonal chemical reporter. Once introduced into target biomolecules, either metabolically or through chemical modification, the azide can be tagged with probes using one of three highly selective reactions: the Staudinger ligation, the Cu(I)-catalyzed azide-alkyne cycloaddition, or the strain-promoted [3+2] cycloaddition. Agard et al. J Am Chem Soc. 2004 Nov. 24; 126(46):15046-7

The use of bioorthogonal chemical reporter molecules has previously been used in labeling of nucleic acid through the incorporation of nucleoside analogs. Thus, one can pulse label DNA using bioorthogonal labeling such as the Staudinger ligation, Cu(I)-catalyzed [3+2] cycloaddition of azides and alkynes ("click chemistry") or "copper-less" click chemistry independently described by Barry Sharpless and Carolyn Bertozzi. Sharpless et al. Angew Chem Int Ed Engl. 2002 Mar. 15; 41(6):1053-7 (herein incorporated fully by reference); Meldal et al. J. Org. Chem. 2002, 67, 3057 (herein incorporated fully by reference); Agard et al. J Am Chem Soc. 2004 Nov. 24; 126(46):15046-7 (herein incorporated fully by reference); U.S. Pat. No. 7,122,703; US Publication No. 2003000516671. Click chemistry and the Staudinger ligation have been adapted to measure cellular proliferation through the direct detection of nucleotide incorporation. See Salic, et al., Methods and Compositions for Labeling Nucleic Acids, U.S. Publication No. 20070207476 and 20070099222 (filed Oct. 27, 2006) (herein incorporated fully by reference).

The term "click chemistry" refers to a [3+2] cycloaddition reaction when performed in the presence of a copper(I) catalyst. The copper(I) catalyst may consist of copper(I) ions or a copper(I) chelating moiety. The copper(I) chelating moiety may be "any entity characterized by the presence of two or more polar groups that can participate in the formation of a complex (containing more than one coordinate bond) with copper(I) ions." Salic et al., U.S. Pat. App. No. 20070207476 (supra). Copper(I) chelating agents are well known in the art and include, but are not limited to, neocuproine and bathocuproine disulphonate. Salic et al., U.S. Pat. App. No. 20070207476 and Sharpless et al., US Publication No. 2003000516671.

[3+2] cycloaddition reactions are also known as 1,3 dipolar cycloadditions, and may occur between 1,3-dipoles and dipolarophiles. Examples of 1,3-dipoles and dipolarphiles are well known in the art. As one example, the 1,3-dipole may be an azide, and the dipolarphile may be an alkyne.

Click chemistry techniques to pulse label DNA involve treating a cell with a first nucleoside analog containing a reactive unsaturated group such that the first nucleoside analog is incorporated into newly synthesized DNA. Then, the cell is contacted with a reagent comprising a second reactive unsaturated group attached to a label, such that a [3+2] cycloaddition occurs between the first and second reactive unsaturated groups.

The following descriptions of [3+2] cycloaddition reactions to pulse label DNA are provided as examples only and are not intended to limit the scope of the present invention.

As one example of pulse labeling DNA using click chemistry, cells are treated with an effective amount of an alkyne-modified nucleoside analog, for example, ethynyl-deoxyuracil (EdU), for a defined period of time such that the EdU is incorporated into newly synthesized DNA. After being pulse labeled with EdU, the cells are fixed, permeabilized, and reacted, in the presence of a copper(I) catalyst, with a dye-labeled azide. A covalent bond is formed between the dye and the incorporated nucleoside analog, via a [3+2] cycloaddition reaction, and the dye label may then be measured using standard methods, including, but not limited to, flow cytometry, fluorescence microscopy, imaging, multi-well plate assays, or high content screening.

In a second example of pulse labeling DNA using click chemistry, cells are treated with an effective amount of an azide-modified nucleoside analog, for example, 5-azido-2'-deoxyuracil (AzdU), for a defined period of time such that AzdU is incorporated into the newly synthesized DNA. After this pulse labeling with AzdU, the cells are fixed, permeabilized and reacted, in the presence of a copper(I) catalyst, with a dye-labeled alkyne. As a result of a [3+2] cycloaddition reaction between the azide and alkyne moieties, a covalent bond is formed. The dye label may then be measured using standard methods, including, but not limited to, flow cytometry, fluorescence microscopy, imaging, multi-well plate assays, or high content screening.

One alternative to click chemistry, which takes advantage of strained [3+2] cycloaddition reactions without using a copper(I) catalyst, has been described by Bertozzi et al. is the "copper-less" click chemistry reaction. Bertozzi et al., Compositions and methods for modification of biomolecules, U.S. Patent App. No. 20060110782 (filed Oct. 31, 2005)(herein incorporated fully by reference).

For example, cells may be first treated with an effective amount of an azide-modified nucleoside analog, for example, AzdU, for a defined period of time such that the azide-modified nucleoside analog is incorporated into newly synthesized DNA. After this pulse of AzdU, cells are treated with an effective amount of a compound or molecule with a reactive cycloalkyne moiety such that a strained [3+2] cycloaddition reaction occurs between the azide and cycloalkyne moieties. The cycloalkyne may be modified to further comprise a dye label, which may then be measured using standard methods, including but not limited to, flow cytometry, fluorescence microscopy, imaging, multi-well plate assays, or high content screening. Cycloalkynes that may be used in strained [3+2] cycloaddition reactions in order to pulse label DNA include, but are not limited to: cyclooctynes, difluorocyclooctynes, heterocycloalkynes, dichlorocyclooctynes, dibromocyclooctynes, or diiodocyclooctynes.

Other chemistries known in the art may be applied to the pulse labeling of DNA. For example, azide-phosphine chemistry described by Bertozzi et al., also know as the Staudinger ligation, may be used to detect incorporation of an azide-modified nucleoside analog, e.g. AzdU, into newly synthesized DNA. See Bertozzi et al., Chemoselective ligation, U.S. Patent App. No. 20070037964 (filed Sep. 19, 2006) (herein incorporated fully by reference). Cells are first contacted with an effective amount of an azide-modified nucleoside analog, e.g. AzdU, for a defined period of time. Then, cells are reacted with an engineered phosphine moiety. One example of an engineered phosphine moiety is 2-diphenylphosphanyl-benzoic acid methyl ester. When azide-phosphine chemistry is used to pulse label DNA, the engineered phosphine moiety further comprises a dye label. Once the reaction between the azide and phosphine moieties has taken place, the dye label may then be measured using standard methods, including, but not limited to, flow cytometry, fluorescence microscopy, imaging, multi-well plate assays, or high content screening.

In some experiments, it is desirable to pulse label DNA with two different nucleoside analogs such that a baseline proliferation rate may be established. Current methods known in the art, including those described above, require removal of the first pulse label of nucleoside analog from the culture medium or organism before addition of the second pulse label. This wash requirement introduces artifacts that affect quantification of DNA synthesis. Therefore, there is a need in the art for a method for the dual pulse labeling of DNA without an intermediary wash step.

SUMMARY OF INVENTION

This invention provides methods of using two or more nucleoside analogs to pulse label nucleic acid to measure baseline and a change in cellular nucleic acid synthesis.

In one embodiment is provided a method for measuring a change in cellular nucleic acid synthesis, wherein the method comprises:
a) incubating a sample with an effective amount of a first nucleoside or nucleotide analog to form a primary incubated sample;
b) incubating the primary incubated sample with at least one second nucleoside or nucleotide analog to form a secondary incubated sample;
c) incubating the secondary incubated sample with a first labeling reagent and at least one second labeling reagent to form a labeled sample;
d) detecting the labeled sample wherein a level of incorporation of the first and at least one second nucleoside or nucleotide analog is measured,
wherein a difference in a level of incorporation of the at least one second nucleoside or nucleotide analog relative to the level of incorporation of the first nucleoside or nucleotide analog is measured as a change in cellular nucleic acid synthesis,
with the proviso that either the first nucleoside or nucleotide or the at least one second nucleoside or nucleotide contains a bioorthogonal functional moiety.

In other embodiments are provided methods for measuring a change in cellular RNA synthesis, methods for measuring a change in cellular DNA synthesis, and methods for screening compounds for effects on cellular proliferation or gene expression.

In certain aspects the first and/or second nucleoside analog contains a bioorthogonal functional moiety, wherein the functional moiety can undergo a [3+2] cycloaddition reaction or a Staudinger ligation. In one instance the bioorthogonal functional moiety contains an azido, alkyne or phosphine moiety. In a particular aspect the nucleoside analog is ethynyl-deoxyuracil (EdU) or 5-azido-2'-deoxyuracil (AzdU). At least the first or the second nucleoside analog contains a bioorthogonal functional moiety.

In another embodiment the first or second nucleoside analog contains a halogen moiety, which may be bromo, chloro or iodo. In one aspect the nucleoside analog is BrdU.

Also provided are a first and at least one second labeling reagent, wherein the labeling reagent covalently or non-covalently bond to the incorporated nucleoside analog. In one embodiment, the first labeling reagent and second labeling reagent is an antibody or a label that contains a bioorthogonal functional moiety. In one aspect the label is a fluorescent dye. In another aspect the antibody is an anti-BrdU antibody.

In certain aspects the bioorthogonal function moiety is an azide, wherein the labeling reagent is rhodamine-azide, Alexa Fluor® 350-azide, Alexa Fluor® 488-azide, Alexa Fluor® 555-azide, Alexa Fluor® 568-azide, Alexa Fluor® 568-azide, Alexa Fluor® 594-azide, Alexa Fluor® 633-azide, Alexa Fluor® 647-azide, Pacific Blue™ azide, Cascade Blue® azide, fluorescein-azide, cyanine-azide, or tetramethylrhodamine (TMR)-azide.

In certain embodiments of the present invention, detecting incorporation of the first nucleoside analog and the at least one competitive nucleoside analog may further comprise using flow cytometry, fluorescence microscopy, imaging, high content screening, or multi-well plate assays.

In one embodiment of the present invention, cellular proliferation is measured by: treating a cell with an effective amount of a first nucleoside analog; treating the cell with an effective amount of at least one second nucleoside analog; detecting incorporation of the first nucleoside analog; and detecting incorporation of the at least one competitive nucleoside analog.

In certain embodiments of the present invention, treatment of cells with the first pulse label of a nucleoside analog is followed by the administration of a specific course of treatment or testing. These test treatments or test compounds may cause an intended alteration of cellular proliferation, as in the case of screening for cancer therapeutic drugs by the addition of the drug to the culture medium system or to the animal being tested. This treatment would be simultaneous to or followed by a pulse from the second nucleoside analog (e.g. the addition of BrdU), without an interruption in the course of treatment for the removal of the first nucleoside analog or clearance in the case of an animal.

In certain embodiments of the present invention, the method of measuring cellular proliferation is performed on a cell selected from, but not limited to, the group consisting of: a Jurkat cell, a MOLT4 cell, a HeLa cell, a COS7 cell, a CHOK1 cell, an A549 cell, a 3T3 cell, phorbitol-stimulated peripheral blood lymphocytes, U266, H929, L1210, K562, EL4, SK-BR3, HL60, MCF7, A431, and BT-474.

In another embodiment is provided a kit for measuring a change in cellular nucleic acid synthesis, wherein the kit comprises: a first nucleoside or nucleotide analog; at least one second nucleoside or nucleotide analog, wherein in at least the first analog or the at least one second nucleoside or nucleotide analog contains a bioorthogonal functional moiety; a first labeling reagent; and a second labeling reagent. Additional kit components include buffers, detection reagents and instructions for using the kit components to measure a change in cellular nucleic acid synthesis.

BRIEF DESCRIPTION OF THE FIGURES

FIG. 2B is a graph of EdU vs. DNA cell cycle. Gating applied with P4>P1 demonstrates that some of the EdU-positive cells are BrdU-negative. These are the cells which have passed out of the synthesis phase of the cell cycle during the initial thirty minute pulse of EdU only incorporation (first pulse) before the BrdU-incorporation (second pulse).

FIG. 3A-1, FIG. 3A-2 and FIG. 3A-3 present a series of graphs showing populations of cells treated with a first pulse label of EdU (10 μm) and a second pulse label of BrdU (10 μm) as detected by flow cytometry. The first graph (FIG. 3A-1) is divided into four quadrants with the first quadrant (Q1) located in the upper left hand corner, the second quadrant (Q2) located in the upper right hand corner, the third quadrant (Q3) located in the lower left hand corner, and the fourth quadrant (Q4) located in the lower right hand corner. Populations of cells in quadrant Q3 (lower left) are negative for both EdU (first pulse) and BrdU (second pulse). Populations of cells in quadrant Q2 (upper right) are positive for both EdU (first pulse) and BrdU (second pulse). FIG. 3A-2 is a graph of EdU vs. DNA cell cycle with gating P5>P1. FIG. 3A-2 shows a subpopulation of BrdU-positive cells which are EdU-negative, this subpopulation being the population of cells entering the DNA synthesis phase of the cell cycle after the first pulse of thirty minutes of EdU-only incorporation.

FIG. 4A, FIG. 4B, FIG. 4C and FIG. 4D present a series of graphs showing populations of cells treated with a first pulse label of EdU (10 μm) and a second pulse label of BrdU (10 μm) as detected by flow cytometry. The first graph (FIG. 4A) is divided into four quadrants with the first quadrant (Q1) located in the upper left hand corner, the second quadrant (Q2) located in the upper right hand corner, the third quadrant (Q3) located in the lower left hand corner, and the fourth quadrant (Q4) located in the lower right hand corner. Populations of cells in quadrant Q3 (lower left) are negative for both EdU (first pulse) and BrdU (second pulse). Populations of cells in quadrant Q2 (upper right) are positive for both EdU (first pulse) and BrdU (second pulse). The Q4 quadrant are cells labeled in the first pulse with EdU but not labeled in the second pulse with BrdU because they have moved into G2/M and are no longer synthesizing DNA. The Q1 quadrant subpopulation are cells not labeled in the first pulse with EdU but have just entered into the DNA synthesis phase during the second pulse and are labeled with BrdU. FIG. 4C is a graph of EdU vs. cycle. In FIG. 4C and FIG. 4D, subpopulations moving into or out of the DNA synthesis phase of the cell cycle show only a single label.

FIG. 6A depicts EdU is incorporated into the DNA double helix. When EdU is incorporated into the DNA, the analog is easily accessible for labeling with the Alexa Fluor® azide without requiring a denaturation step. FIG. 6B shows that denaturation is required for standard antibody-based labeling of incorporated BrdU.

A series of result graphs labeled

treated with a first pulse label of EdU (20 µM) and a second pulse label of BrdU (10 µm) as detected by flow cytometry.

Figure 8A:
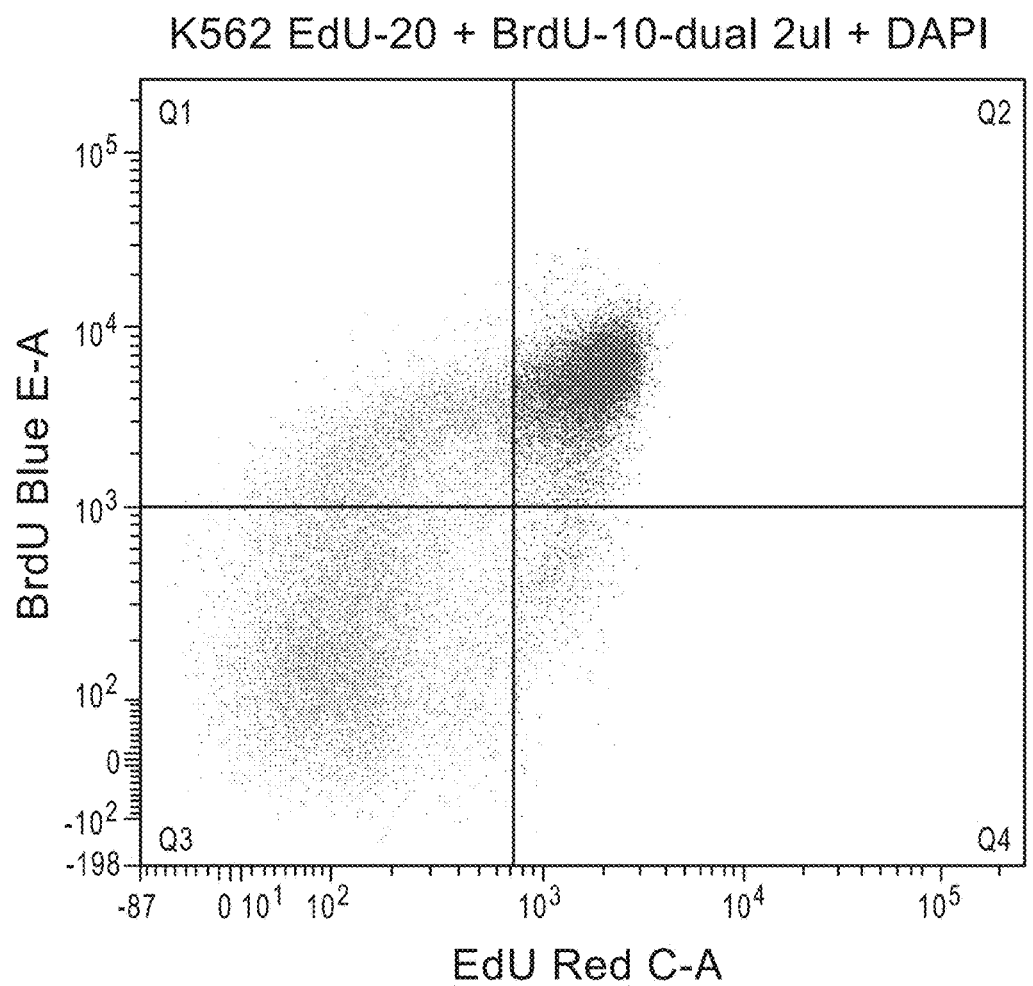
Figure 8B:
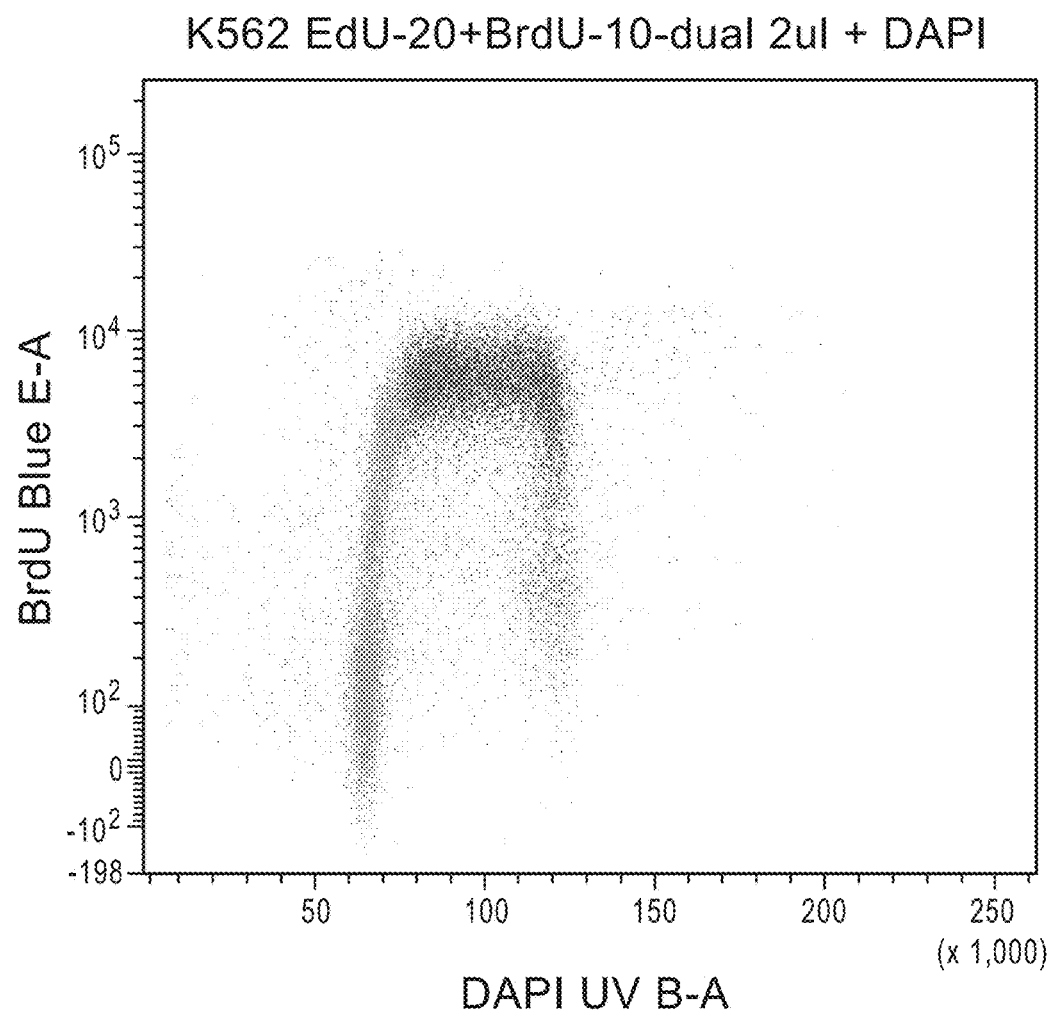
Figure 8C:
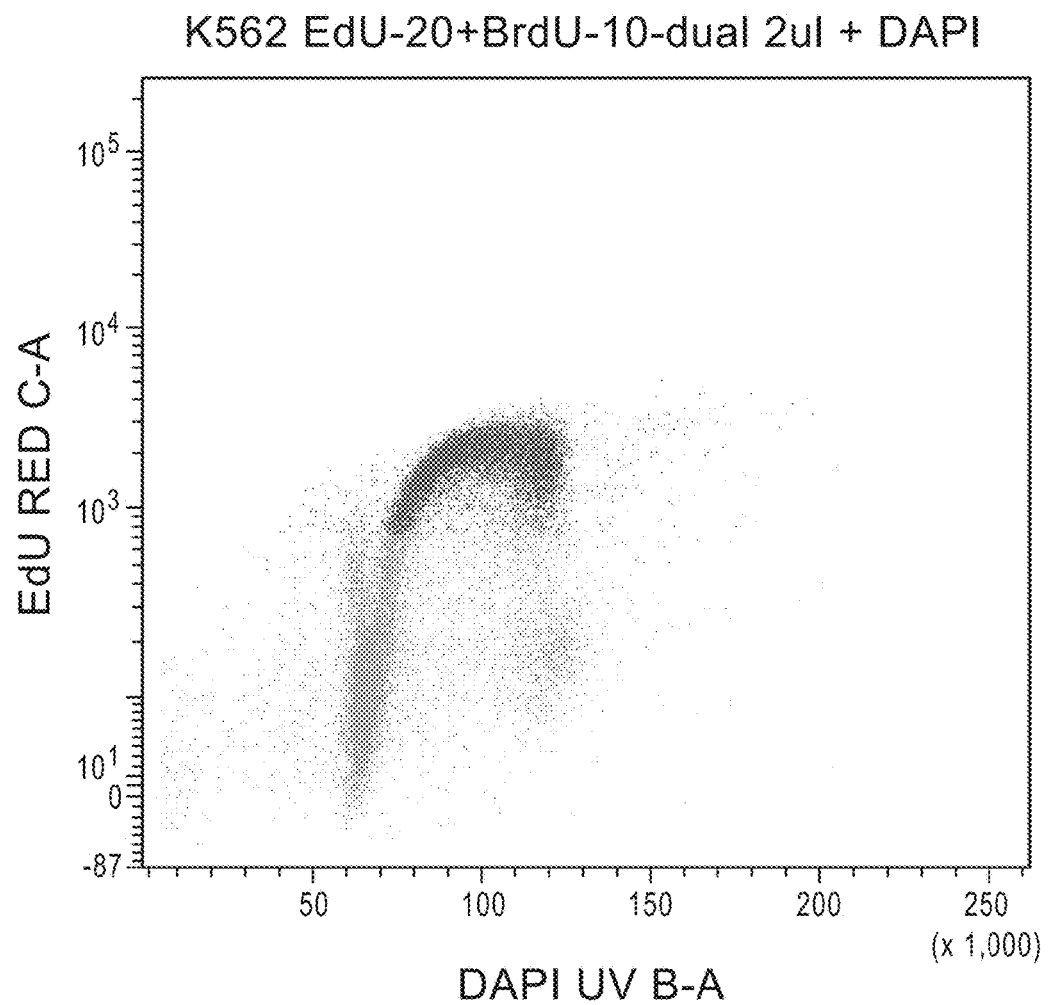

A series of result graphs labeled FIG. 8A, FIG. 8B and FIG. 8C show populations of cells (K562 human lymphoblast from chronic myelogenous leukemia cells) treated with a first pulse label of EdU (20 µM) and a second pulse label of BrdU (10 µm) as detected by flow cytometry.

Figures 1A, 9:
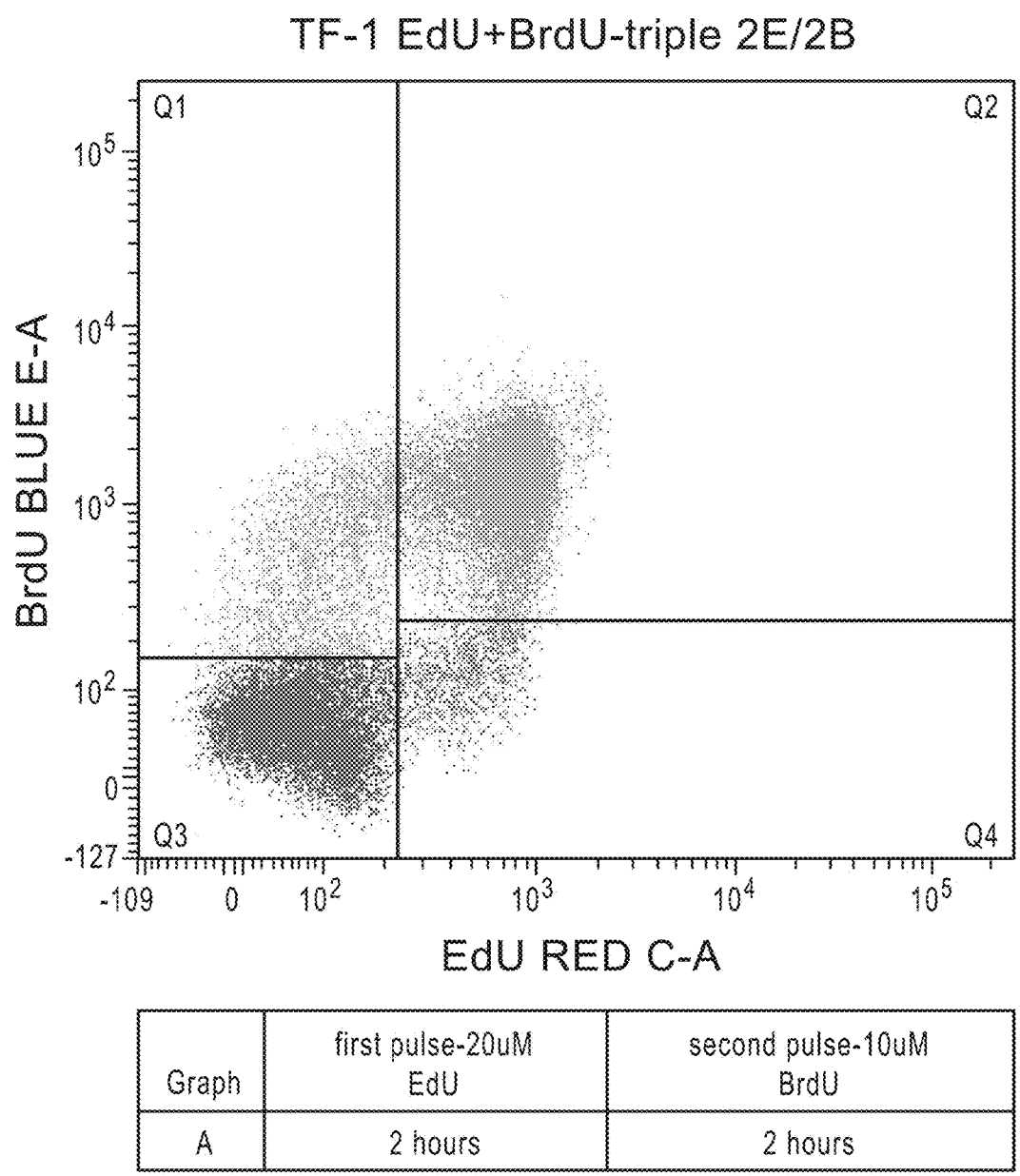
Figures 1B, 9:
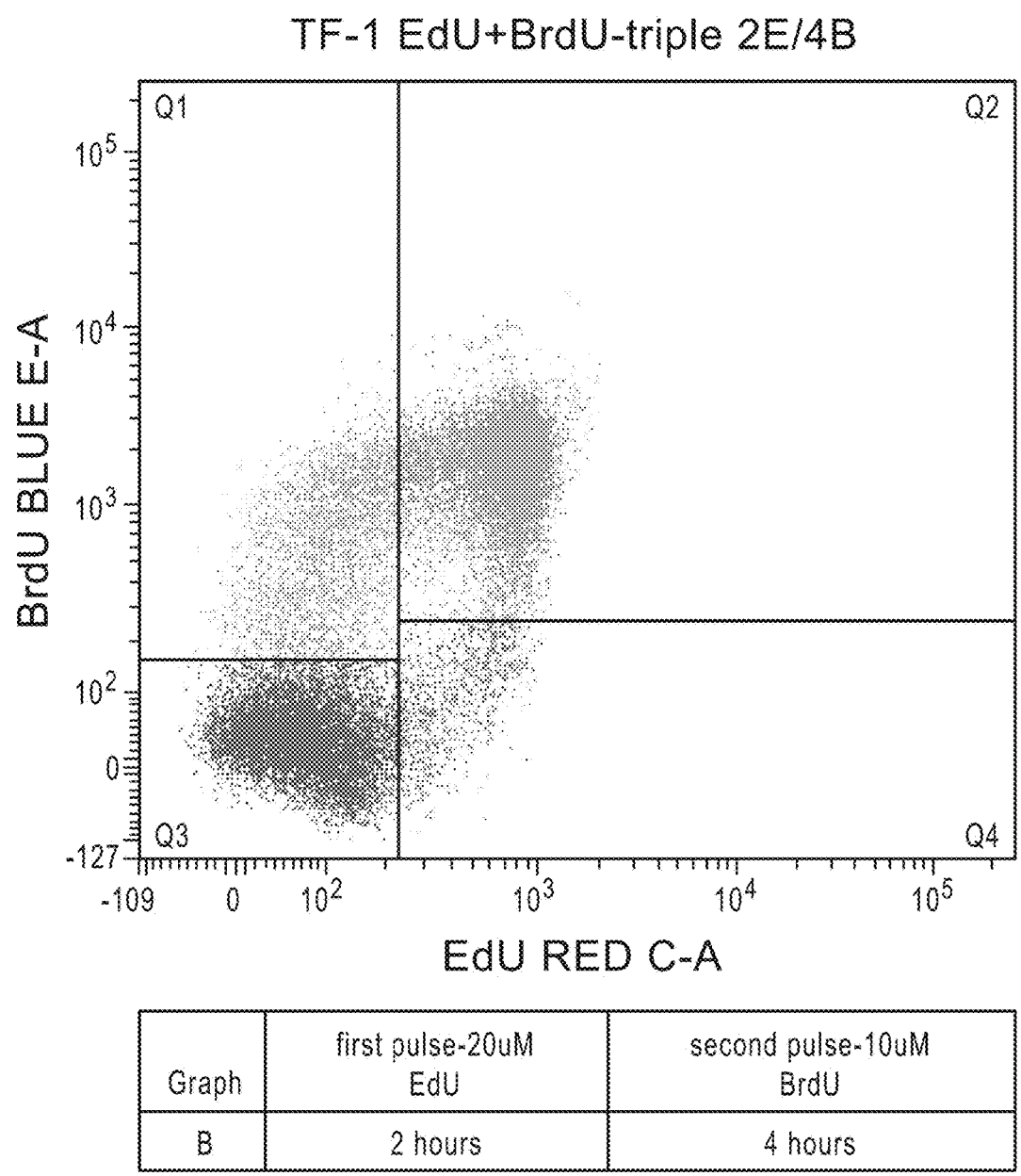
Figures 1C, 9:
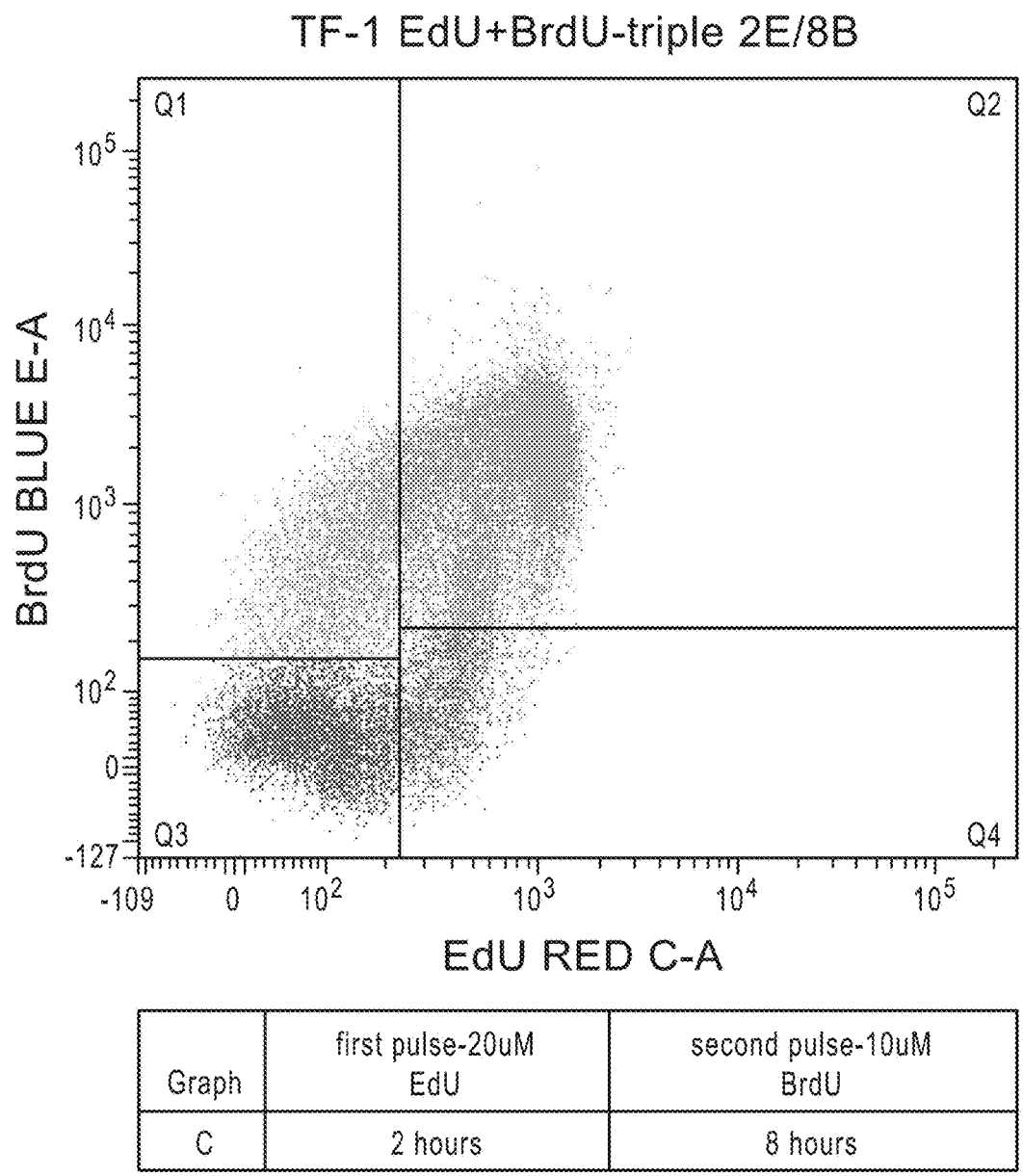
Figures 2D, 9:
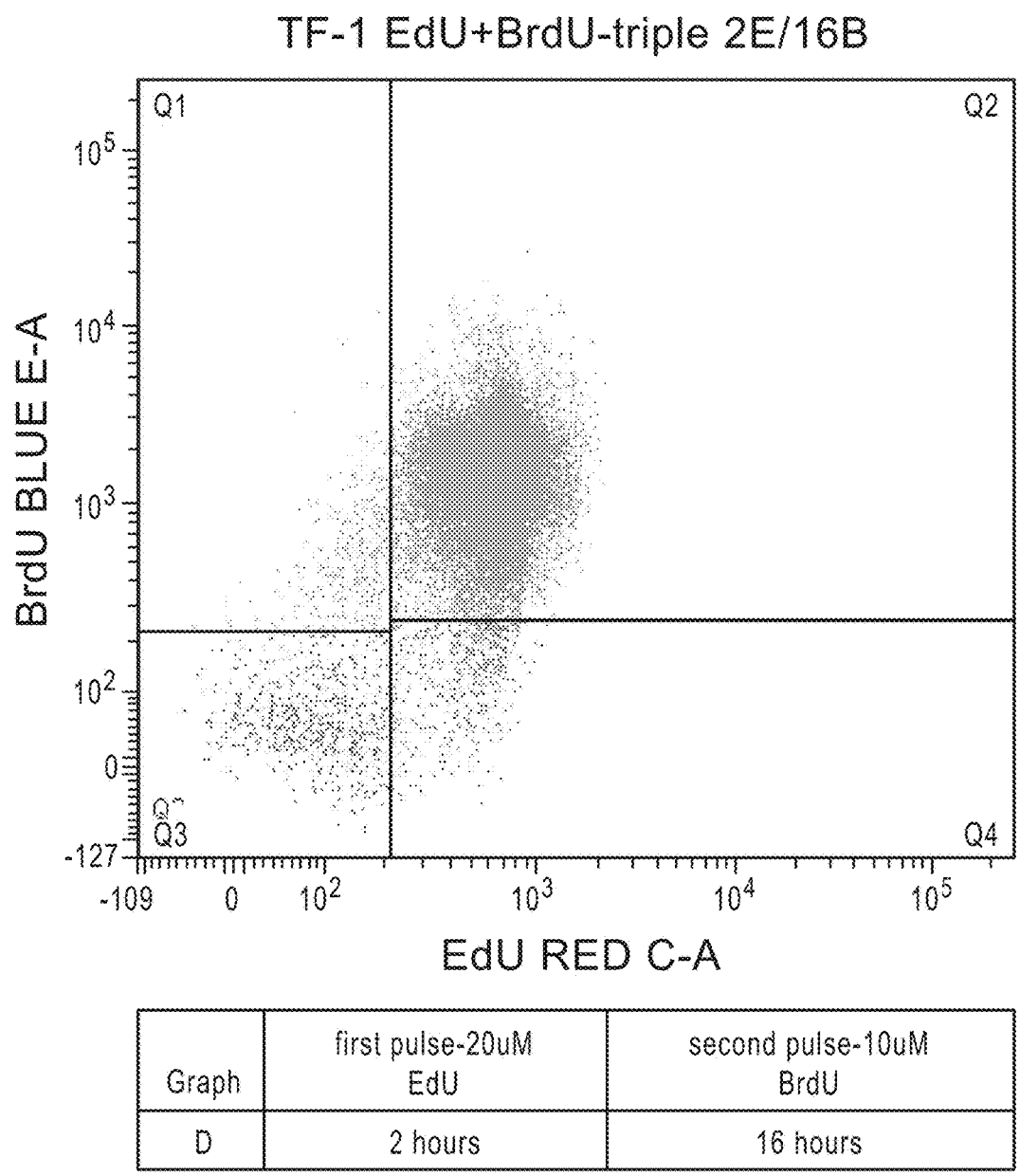
Figures 2E, 9:
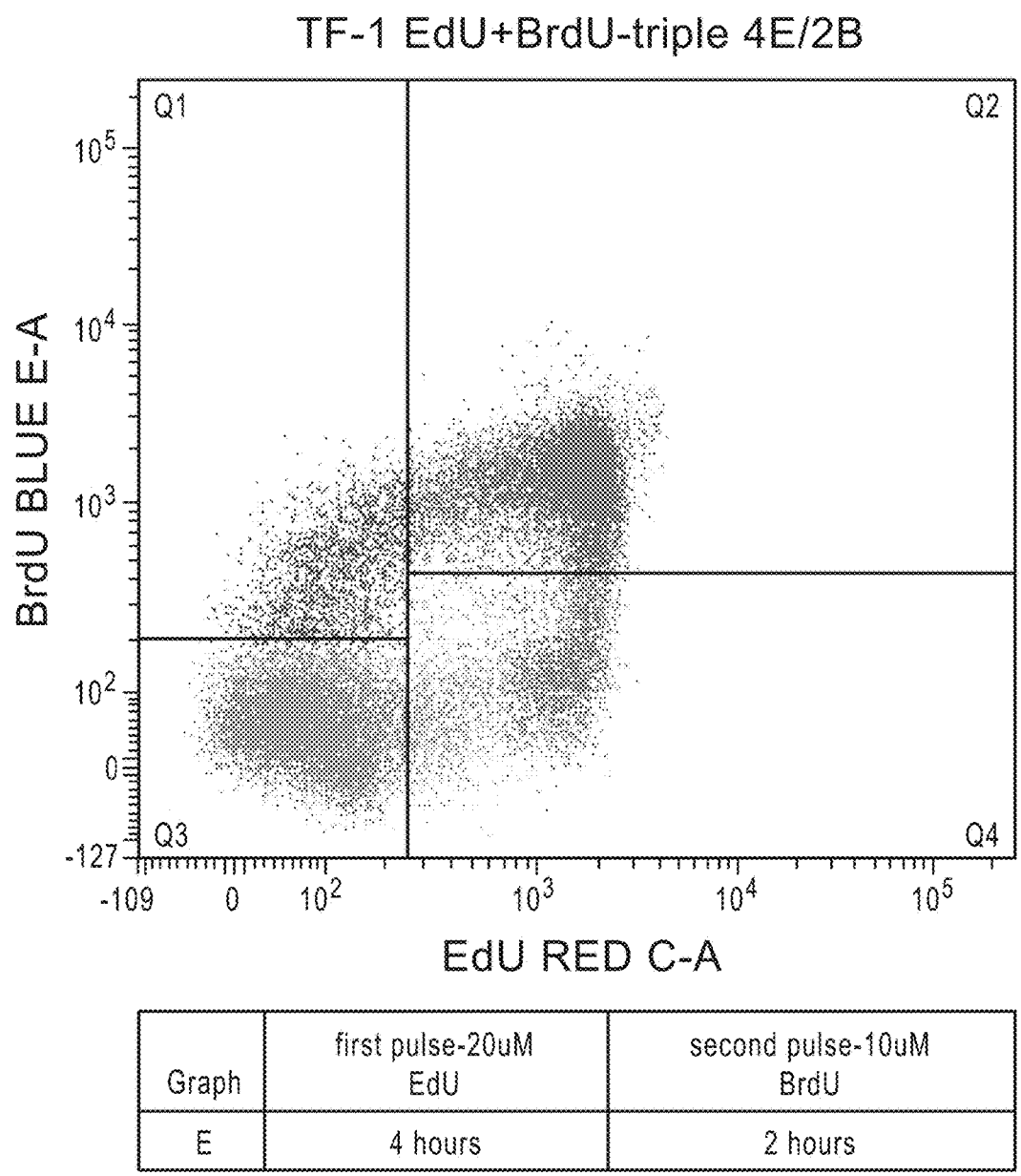
Figures 2F, 9:
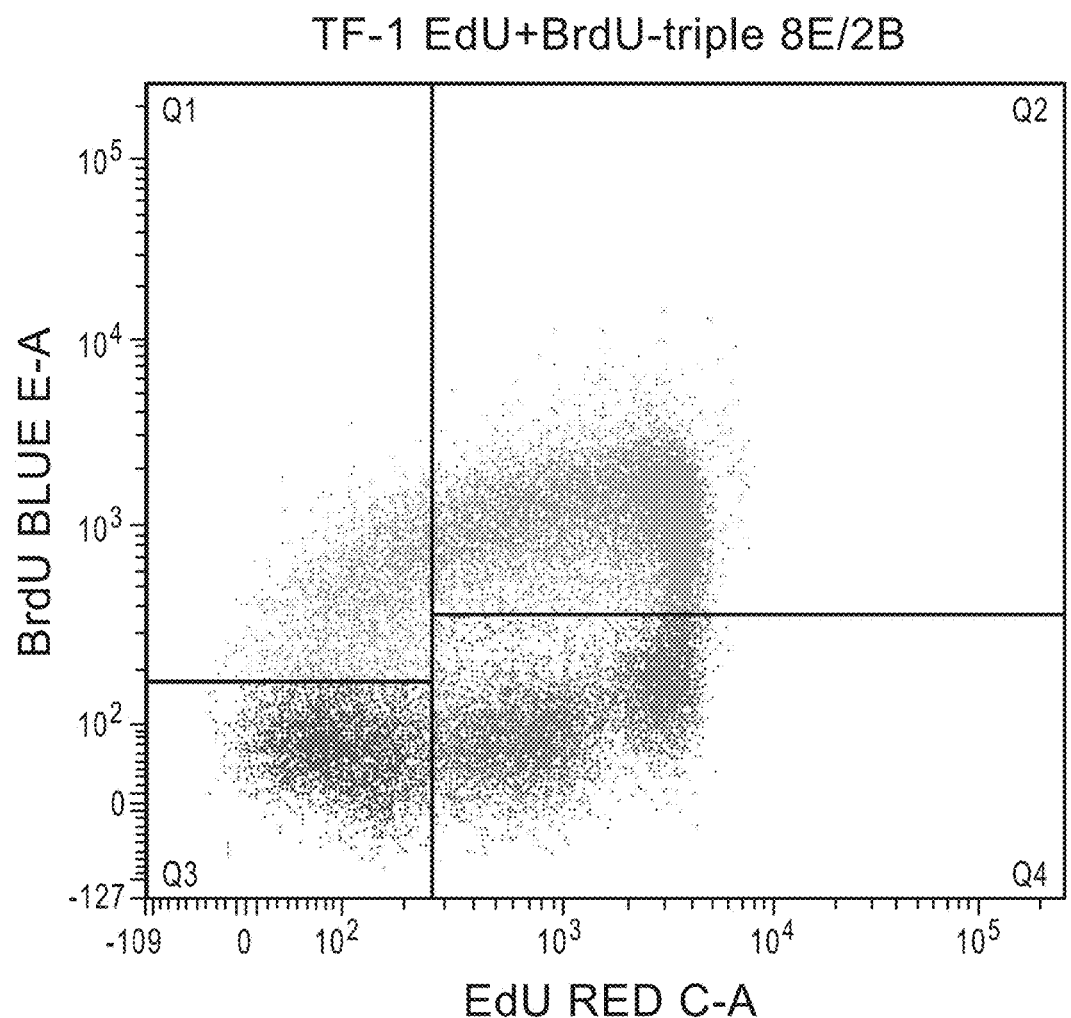
Figures 3G, 9:
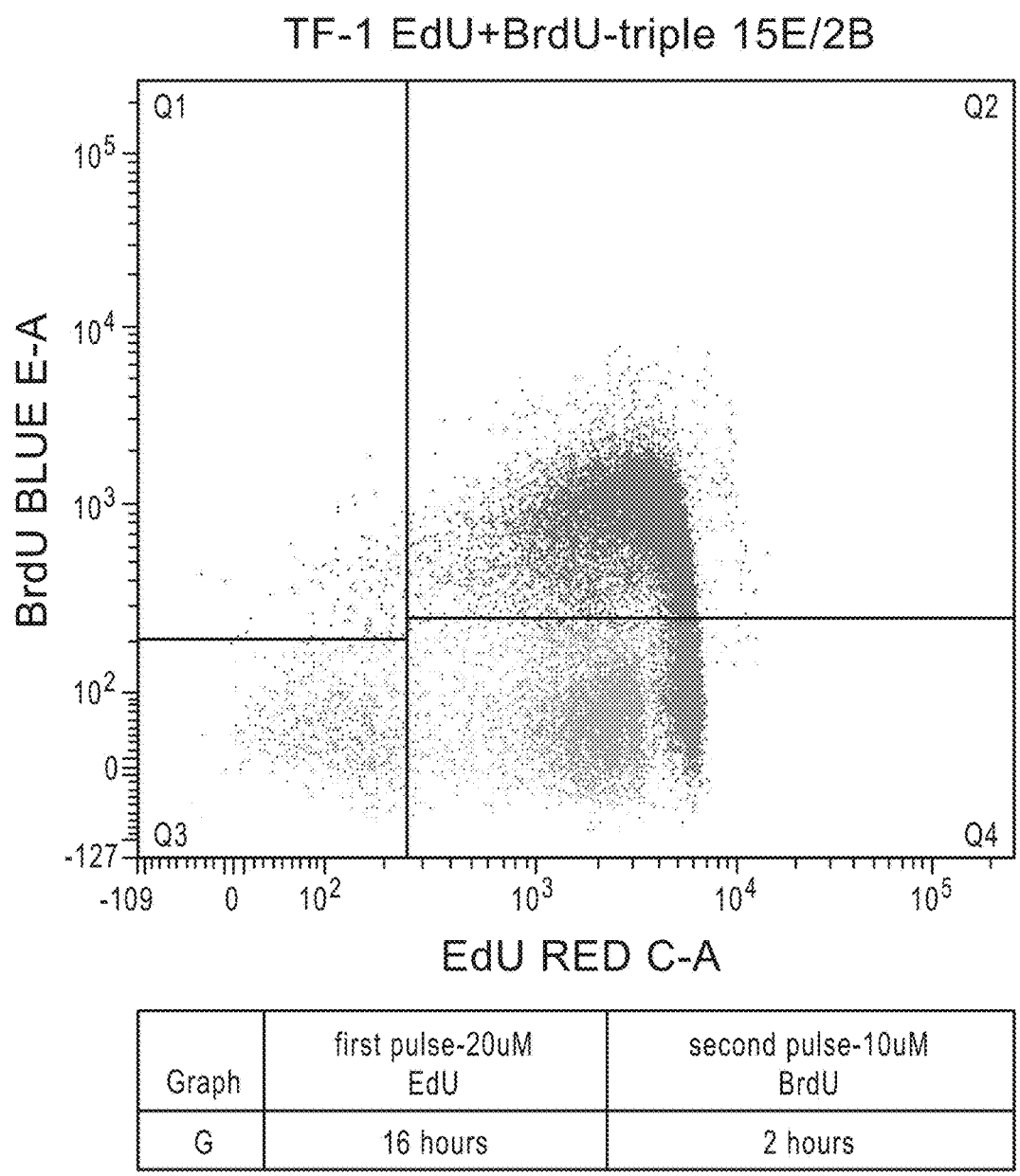
Figures 3H, 9:
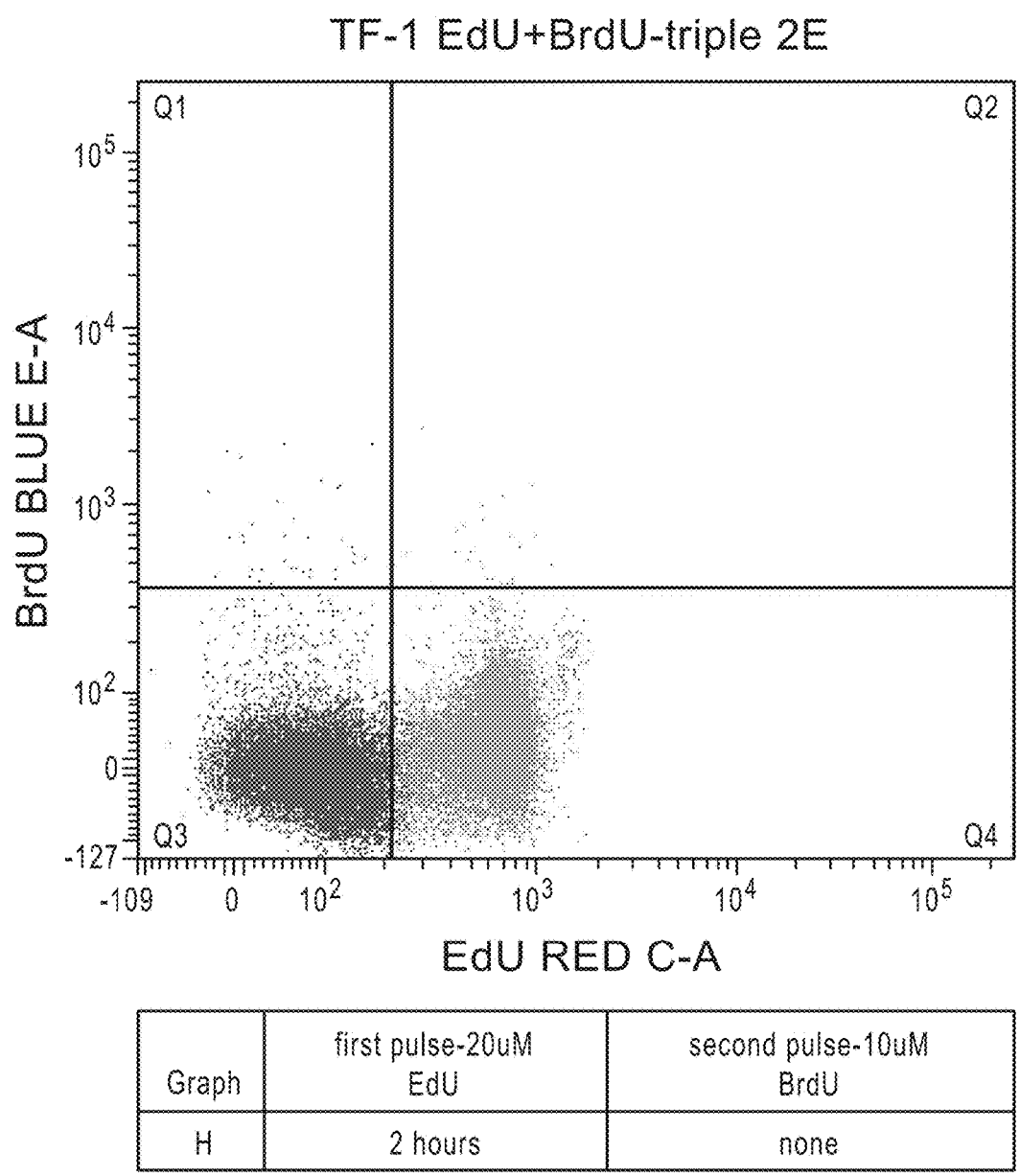
Figures 3I, 9:
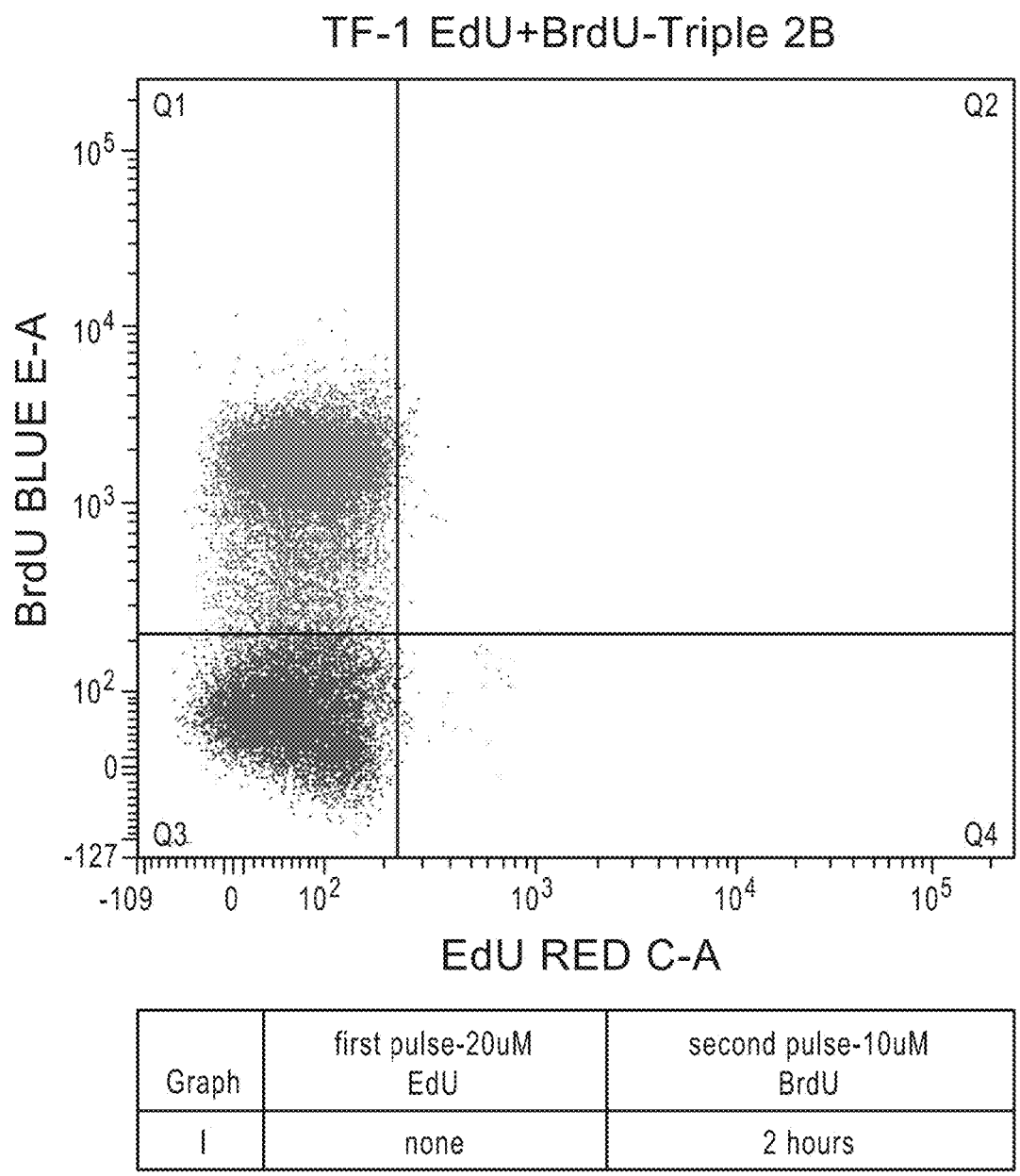

A series of result graphs labeled FIGS. 9-1A, 9-1B, 9-1C, 9-2D, 9-2E, 9-2F, 9-3G, 9-3H and 9-3I show populations of cells (TF-1a human erythroblast cells). FIGS. 9-1A, 9-1B, 9-1C, 9-2D, 9-2E, 9-2F and 9-3G show the population of the cells treated with a first pulse label of EdU (20 µM) and a second pulse label of BrdU (10 µm) with the time of the pulses varied, as detected by flow cytometry. FIGS. 9-3H and 9-3I show the population of the cells treated with one pulse only, with FIG. 9-3H showing the result of a pulse label of EdU (20 µM) only and FIG. 9-3I showing result of a pulse label of BrdU (10 µm) only, as detected by flow cytometry.

A series of result graphs labeled FIG. 10A, FIG. 10B, FIG. 10C, FIG. 10D and FIG. 10E show populations of cells (THP-1 monocyte cells) treated with a first pulse label of EdU (20 µM) and a second pulse label of BrdU (10 µm) as detected by flow cytometry.

Figure 11:
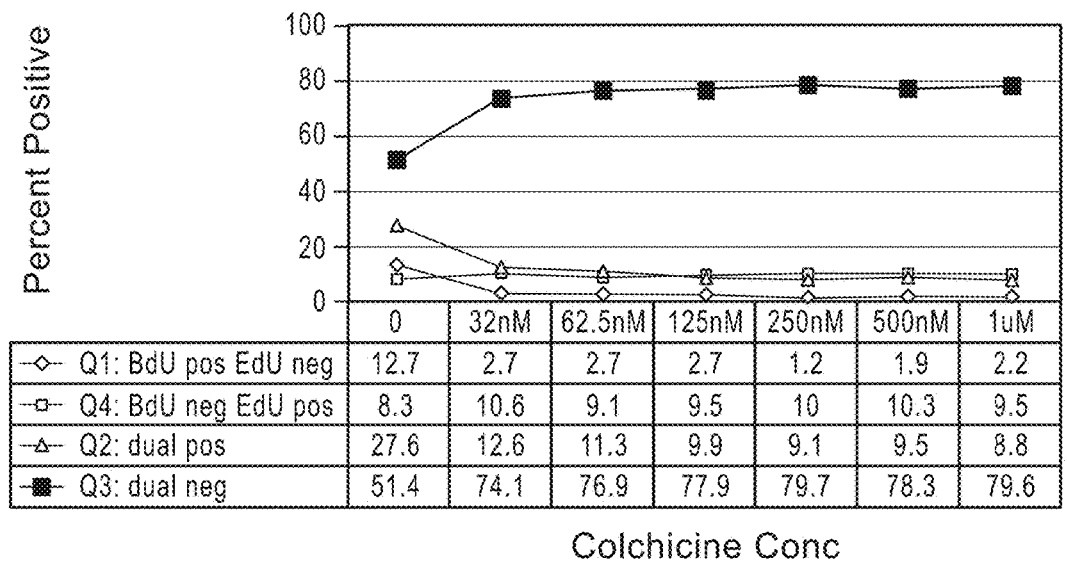

FIG. 11 shows the percentage of cells (Jurkat T-cell lymphocyte cells) which are EdU and BrdU co-positive (Q2), EdU and BrdU co-negative (Q3), BrdU positive and EdU negative (Q1), and BrdU negative and EdU positive (Q4) of the seven different treatment conditions.

A series of result graphs labeled FIGS. 12-1A, 12-1B, 12-1C, 12-1D, 12-1E, 12-2F, 12-2G, 12-2H, 12-2I and 12-2J show populations of cells (Jurkat T-cell lymphocyte cells) treated with a first pulse label of EdU (20 µM) and a second pulse label of BrdU (10 µm) as detected by flow cytometry.

DETAILED DESCRIPTION OF THE INVENTION

Introduction:

Herein we describe methods for measuring cellular nucleic acid synthesis with the incorporation of bio-orthogonal nucleoside or nucleotide analogs such that the newly synthesized cellular nucleic acid can be dual labeled without the need for a disruptive wash step. These analogs include, but are not limited to, halogenated (such as BrdU), an azido modified analog, an alkyne modified analog or a phosphine modified analog. The incorporation of these analogs is then detected by measurement of a fluorescent signal wherein the label is selectively attached to the nucleic acid analog due to the functional groups of the analog and label or through an antibody. A timed exposure to a nucleoside (or nucleotide) analog with the potential of incorporation of that analog into the actively synthesized cellular nucleic acid is defined as a pulse. The pulse may be measuring baseline proliferation, baseline gene expression, or a response to a specific treatment.

We have found that the addition of an additional pulse with a different nucleoside analog, which is selectively labeled, provides a mechanism to measure both baseline proliferation and a subsequent change in proliferation without the introduction of an artifact of washing or clearing the analog out of the cells or system being measured. It is also envisioned that a third pulse could be performed, for example, but not limited to, the ability to measure drug interaction on cell proliferation or gene expression. A baseline synthesis rate can be recorded by the first pulse labeling of the nucleic acid. Without interruption to remove the first pulse, the second pulse can be started. Normally, interruption to the cells by removing the first pulse label alters the rate of cell proliferation and makes assessment of changes in cell proliferations difficult. In addition the no wash step makes the process compatible with high throughput screening (HTS). Having two compatible methods for pulse labeling nucleic acid without the use of radioactive nucleosides creates a very powerful tool which in one instance can be applied to the assessment of cancer therapy ex vivo or in vivo.

This novel dual labeling method is predicated, in part, on the concept that either the analogs from the first pulse are all incorporated before the addition of the second analog or that the second analog is a competitor for the first, such that the second analog is selectively incorporated into the nascent nucleic acid polymer. Without wishing to be bound to a theory, it appears that in the instance of the analogs, EdU and BrdU, that BrdU is selectively incorporated in the presence of EdU. See, Example 3.

Definitions:

Before describing the present invention in detail, it is to be understood that this invention is not limited to specific compositions or process steps, as such may vary. It should be noted that, as used in this specification and the appended claims, the singular form "a", "an" and "the" include plural references unless the context clearly dictates otherwise. Thus, for example, reference to "a fluorescent pH sensitive dye" includes a plurality of dyes and reference to "a cell" includes a plurality of cells and the like.

Unless defined otherwise, all technical and scientific terms used herein have the same meaning as commonly understood by one of ordinary skill in the art to which this invention is related. It is also understood that when describing chemical moieties or molecules that are attached to another compound that these moieties exist in a radical form for the purposes of conjugation. The following terms are defined for purposes of the invention as described herein.

As used herein, the term "alkyne reactive" refers to a chemical moiety that selectively reacts with an alkyne modified group on the nucleoside analog to form a covalent chemical bond between the alkyne modified group and the alkyne reactive group. Examples of alkyne-reactive groups include azides. "Alkyne-reactive" can also refer to a molecule that contains a chemical moiety that selectively reacts with an alkyne group.

As used herein, the term "azide reactive" refers to a chemical moiety that selectively reacts with an azido modified group on another molecule to form a covalent chemical bond between the azido modified group and the azide reactive group. Examples of azide-reactive groups include alkynes and phosphines (e.g. triaryl phosphine). "Azide-reactive" can also refer to a molecule that contains a chemical moiety that selectively reacts with an azido group.

As used herein, the term "azide-selective phosphine dye" refers to a compound, molecule or reagent that comprises an engineered phosphine moiety with a dye label such that when reacted with an azide, provides for production of a covalent bond between the engineered phosphine moiety and the azide. The term "engineered phosphine moiety" refers to a moiety comprising a phosphine and an electrophilic moiety. One example of an engineered phosphine moiety is 2-diphenylphosphanyl-benzoic acid methyl ester. Other engineered phosphine moieties are known in the art. See, e.g., Bertozzi et al., U.S. Pat. App. No. 20070037964.

As used herein the term "bioorthogonal chemical reporter" or "bioorthogonal labeling reagent" means a detectable label that comprises a chemical handle that will react selectively with the present nucleoside analog once incorporated into nucleic acid to form a covalent bond.

As used herein, the term "cell" in the context of the in vivo applications of the invention is meant to encompass eukaryotic and prokaryotic cells of any genus or species, with mammalian cells being of particular interest. "Cell" is also meant to encompass both normal cells and diseased cells, e.g., cancerous cells.

The terms "cell proliferation" and "cellular proliferation" are used herein interchangeably and refer to an expansion of a population of cells by the division of single cells into daughter cells, or to the division of a single cell to daughter cells.

The term, "chemical handle" or "bioorthogonal moiety" as used herein refers to a specific functional group, such as an azide, alkyne, activated alkyne, phosphite, phosphine, and the like. The chemical handle is distinct from biological reactive groups, defined below, in that the chemical handle are moieties that are rarely found in naturally-occurring biomolecules and are chemically inert towards biomolecules (e.g, native cellular components), but when reacted with an azide- or alkyne-reactive group the reaction can take place efficiently under biologically relevant conditions (e.g., cell culture conditions, such as in the absence of excess heat or harsh reactants).

As used herein, the term "click chemistry" refers to the copper-catalyzed version of a [3+2] cycloaddition reaction between a first reactive unsaturated group on the incorporated nucleoside analog (nucleotide analog) or labeling reagent and a second reactive unsaturated group present on the labeling regent or nucleoside analog (nucleotide analog). This click chemistry reaction is described by Sharpless et al. (Sharpless et al., Angew Chem., Int. Ed. Engl., 2002, 41:1596-1599).

As used herein, the term "competitive nucleoside analog" refers to a nucleoside analog, which when added simultaneously to the first nucleoside analog in a cell or an organism, results in a population of cells that are preferentially labeled with the competitive nucleoside analog and not the first nucleoside analog. For example, when BrdU (competitive nucleoside analog) and EdU (first nucleoside analog) are simultaneously added to cells in a dual pulse experiment, only BrdU, the competitive nucleoside analog in this pair of nucleoside analogs, is incorporated into the DNA (see, e.g., FIGS. 5A, 5B, 5C and 5D and Example 3).

As used herein, the term "copper(I) catalyst" refers to a compound, molecule or reagent that catalyzes the [3+2] cycloaddition reaction between a first reactive unsaturated group on the incorporated nucleoside analog (nucleotide analog) or labeling reagent and a second reactive unsaturated group present on the labeling reagent or nucleoside analog (nucleotide analog). The term "copper(I) catalyst" includes exogenous copper(I) as well as copper chelating moieties. The term "copper chelating moieties" refers to any compound, molecule or reagent characterized by the presence of two or more polar groups that can participate in the formation of a complex with copper(I) ions.

As used here, the term "copperless click chemistry" refers to a strain-promoted [3+2] cycloaddition reaction that can be carried out under physiological conditions, as described by Bertozzi et al. US Publication No. 20060110782; Baskin et al. PNAS 2007 Oct. 23; 104(43):16793-7; Agard et al. J Am Chem Soc. 2004 Nov. 24; 126(46):15046-7. The reaction is accomplished through use of a first molecule comprising a strained cycloalkyne moiety (typically the label), and second molecule comprising an azide moiety (typically the nucleoside analog). The azide moiety on the second molecule reacts, in the absence of a catalyst, with the strained cycloalkyne moiety on the first molecule, forming a final conjugate product comprising fused azide/cycloalkyne ring.

As used here, the term "detectable response" refers to an occurrence of or a change in, a signal that is directly or indirectly detectable either by observation or by instrumentation. Typically, the detectable response is an optical response resulting in a change in the wavelength distribution patterns or intensity of absorbance or fluorescence or a change in light scatter, fluorescence lifetime, fluorescence polarization, or a combination of the above parameters.

As used here, the term "dye" refers to a compound that emits light to produce an observable detectable signal.

As used herein, the terms "dye-labeled azide" and "azide-dye molecule" refer to a compound or molecule with a reactive azide group that is also labeled with a dye. Examples include, but are not limited to: rhodamine-azide, Alexa Fluor® 350-azide (Molecular Probes™/Invitrogen™, Carlsbad, Calif.), Alexa Fluor® 488-azide (Molecular Probes™/Invitrogen™, Carlsbad, Calif.), Alexa Fluor® 555-azide (Molecular Probes™/Invitrogen™, Carlsbad, Calif.), Alexa Fluor® 568-azide (Molecular Probes™/Invitrogen™, Carlsbad, Calif.), Alexa Fluor® 568-azide (Molecular Probes™/Invitrogen™, Carlsbad, Calif.), Alexa Fluor® 594-azide, Alexa Fluor® 633-azide (Molecular Probes™/Invitrogen™, Carlsbad, Calif.), Alexa Fluor® 647-azide (Molecular Probes™/Invitrogen™, Carlsbad, Calif.), Cascade Blue® azide (Molecular Probes™/Invitrogen™, Carlsbad, Calif.), fluorescein-azide, coumarin-azide, BODIPY-azide, cyanine-azide, or tetramethylrhodamine (TMR)-azide.

As used herein, the term "dye-labeled cycloalkyne" refers to a cycloalkyne that has been further modified to include a dye label. The term "cycloalkyne" refers to compounds or molecules which may be used in strained [3+2] cycloaddition reactions in order to pulse label DNA. In this context, examples of cycloalkynes include, but are not limited to: cyclooctynes, difluorocyclooctynes, heterocycloalkynes, dichlorocyclooctynes, dibromocyclooctynes, or diiodocyclooctynes.

As used herein, the term "dye-labeled alkyne" refers to an alkyne that has been further modified to include a dye label.

As used herein, the term "dual labeling" refers to a labeling process in which a nucleic acid polymer is labeled with two detectable agents that produce distinguishable signals. The nucleic acid polymer resulting from such a labeling process is said to be dually labeled.

As used herein, the term "effective amount" refers to the amount of a substance, compound, molecule, agent or composition that elicits the relevant response in a cell, a tissue, or an organism. For example, in the case of cells contacted with a nucleoside analog, an effective amount is an amount of nucleoside that is incorporated into the DNA of the cells.

As used here, the term "fluorophore" or "fluorogenic" refers to a composition that demonstrates a change in fluorescence upon binding to a biological compound or analyte interest. Preferred fluorophores of the present invention include fluorescent dyes having a high quantum yield in aqueous media. Exemplary fluorophores include xanthene, indole, borapolyazaindacene, furan, and benzofuran, cyanine among others. The fluorophores of the present invention may be substituted to alter the solubility, spectral properties or physical properties of the fluorophore.

As used here, the term "label" refers to a chemical moiety or protein that retains it's native properties (e.g. spectral properties, conformation and activity) when part of a labeling reagent of the present invention and used in the present methods. Illustrative reporter molecules can be directly detectable (fluorophore) or indirectly detectable (hapten or enzyme). Such reporter molecules include, but are not limited to, radio reporter molecules that can be measured with radiation-counting devices; pigments, dyes or other chromogens that can be visually observed or measured with a spectrophotometer; spin labels that can be measured with a spin label analyzer; and fluorescent moieties, where the output signal is generated by the excitation of a suitable molecular adduct and that can be visualized by excitation with light that is absorbed by the dye or can be measured with standard fluorometers or imaging systems, for example. The reporter molecule can be a luminescent substance such as a phosphor or fluorogen; a bioluminescent substance; a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The reporter molecule may also take the form of a chemical or biochemical, or an inert particle, including but not limited to colloidal gold, microspheres, quantum dots, or inorganic crystals such as nanocrystals or phosphors (see, e.g., Beverloo, et al., Anal. Biochem. 203, 326-34 (1992)). The term reporter molecule can also refer to a "tag" or hapten that can bind selectively to a labeled molecule such that the labeled molecule, when added subsequently, is used to generate a detectable signal. For instance, one can use biotin, iminobiotin or desthiobiotin as a tag and then use an avidin or streptavidin conjugate of horseradish peroxidase (HRP) to bind to the tag, and then use a chromogenic substrate (e.g., tetramethylbenzidine) or a fluorogenic substrate such as Amplex Red or Amplex Gold (Molecular Probes, Inc.) to detect the presence of HRP. In a similar fashion, the tag can be a hapten or antigen (e.g., digoxigenin), and an enzymatically, fluorescently, or radioactively labeled antibody can be used to bind to the tag. Numerous reporter molecules are known by those of skill in the art and include, but are not limited to, particles, fluorescent dyes, haptens, enzymes and their chromogenic, fluorogenic, and chemiluminescent substrates, and other reporter molecules that are described in the MOLECULAR PROBES HANDBOOK OF FLUORESCENT PROBES AND RESEARCH CHEMICALS by Richard P. Haugland, $10^{th}$ Ed., (2005), the contents of which are incorporated by reference, and in other published sources. As used herein a reporter molecule is not an amino acid.

As used here, the term "Labeling Reagent" refers to a reagent used to label and detect the incorporated nucleotide analog. In one instance, the labeling reagent comprises a label and a chemical handle. In another instance, the labeling reagent comprises an antibody and a label, wherein the antibody binds the nucleoside analog.

As used herein, the term "nucleoside analog" and "nucleotide analog" are used interchangeably and refers to a molecule or compound that is structurally similar to a natural nucleoside or nucleotide that is incorporated into newly synthesized nucleic acid. In the case of nucleosides, once inside the cells, they are phosphorylated into nucleotides and then incorporated into nascent nucleic acid polymers. Nucleotides are difficult to get across the cell membrane due to their charges and are more labile than nucleosides, thus their use typically requires and additional step and reagents for transfection to transport the nucleotides across the lipid bilayer. The present nucleoside analogs are incorporated into nucleic acid (DNA or RNA) in a similar manner as a natural nucleotide wherein the correct polymerase enzyme recognizes the analogs as natural nucleotides and there is no disruption in synthesis. These analogs comprise a number of different moieties which are ultimately used for detection, such as halogenated analogs (bromo, chloro, iodo, etc.) and those that comprise a bioorthogonal moiety such as azido, alkyne or phosphine.

As used here, the term "reactive group" refers to a group that is capable of reacting with another chemical group to form a covalent bond, i.e. is covalently reactive under suitable reaction conditions, and generally represents a point of attachment for another substance. As used herein, reactive groups refer to chemical moieties generally found in biological systems and that react under normal biological conditions, these are herein distinguished from the chemical handle or bioorthogonal functional moiety, defined above, such as the azido and activated alkyne moieties of the present invention. As referred to herein the reactive group is a moiety, such as carboxylic acid or succinimidyl ester, that is capable of chemically reacting with a functional group on a different compound to form a covalent linkage. Reactive groups generally include nucleophiles, electrophiles and photoactivatable groups.

As used here, the term "Staudinger ligation" refers to a chemical reaction developed by Saxon and Bertozzi (E. Saxon and C. Bertozzi, Science, 2000, 287:2007-2010) that is a modification of the classical Staudinger reaction. The classical Staudinger reaction is a chemical reaction in which the combination of an azide with a phosphine or phosphite produces an aza-ylide intermediate, which upon hydrolysis yields a phosphine oxide and an amine. A Staudinger reaction is a mild method of reducing an azide to an amine; and triphenylphosphine is commonly used as the reducing agent. In a Staudinger ligation, an electrophilic trap (usually a methyl ester) is appropriately placed on a triarylphosphine aryl group (usually ortho to the phosphorus atom) and reacted with the azide, to yield an aza-ylide intermediate, which rearranges in aqueous media to produce a compound with amide group and a phosphine oxide function. The Staudinger ligation is so named because it ligates (attaches/covalently links) the two starting molecules together, whereas in the classical Staudinger reaction, the two products are not covalently linked after hydrolysis.

As used herein, the terms "test compound" and "test treatment" refer to any substance, compound, molecule, agent, composition, or treatment, which is tested during the claimed methods for its affect on cellular proliferation or the cell cycle. The affect on cellular proliferation of these "test compounds" and "test treatments" is not limited by outcome, that is, they may increase, decrease or not affect cellular proliferation or the cell cycle.

As used herein, the term "reactive partner" refers to a molecule or molecular moiety that specifically reacts with another reactive partner, such as the present nucleoside analog and the reporter molecule.

Dual Labeling Reagents:

In general, for ease of understanding the present invention, the components for dual labeling of nucleic acid through the incorporation of nucleoside or nucleotide analogs will first be described in detail, followed by a description of the dual labeling methods. This will be followed by some embodiments in which such dual labeled nucleic acid is used to measure cell proliferation. Exemplified methods are then disclosed.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Herein we describe a method for screening test compounds for their effect on nascent cellular nucleic acid synthesis, wherein two color labeling is used to measure baseline nucleic acid synthesis compared to post-treatment synthesis. This method uses nucleoside analogs that are "fed" to cells and incorporated into a growing nucleic acid polymer, wherein at least one of the nucleoside analogs comprises a bioorthogonal functional moiety.

In a particular embodiment a method for screening test compounds for their effect on cellular proliferation is provided. Herein we describe a method for dual labeling wherein the baseline proliferation is measured against a change in proliferation from a treatment of the cells, either in vivo or ex vivo. This is accomplished by using a combination of a halogenated analogs (such as BrdU) or nucleoside analogs comprising a chemical handle in combination with nucleoside analogs comprising a chemical handle, which can be selectively labeled using a labeling reagent of the present invention. The present invention uses at least one nucleoside (or nucleotide) analog that comprises a chemical handle, herein also referred to as a bioorthogonal functional moiety.

Similarly, this dual labeling method can also be used to measure cellular gene expression (RNA synthesis) in response to an administered treatment. In this instance, the nucleic acid analogs comprise a ribose sugar and are RNA nucleoside or nucleotide analogs.

The advantage of this dual labeling method is that it does not require the removal of the first pulse of nucleoside analog from the culture medium, or animal prior to the administering of the second pulse of nucleoside analog. The distinct advantage of this 'no wash' treatment for the additional pulse of the second label is that baseline cell proliferation, or gene expression, measurements can be made using the first pulsed nucleoside analog, followed by the administration of a specific course of treatment or testing which may cause an intended alteration of cell proliferation, or gene expression. For example, as in the case of screening cancer therapeutic drugs by the addition of the drug to the culture medium system, or to the animal being tested. This treatment would be simultaneous to or followed by a pulse from the second nucleoside analog, without an interruption in the course of the treatment for the removal of the first analog. At the end of the test, the cells are prepared for detection of the two pulses of labeling of the nucleic acid.

In one particular aspect, a nucleoside analog comprising a bioorthogonal functional moiety is used in the first pulse followed by a second pulse with a halogenated nucleoside analog. In another aspect a nucleoside analog comprising a first bioorthogonal functional moiety is used in the first pulse followed by a second pulse with a nucleoside analog comprising a second bioorthogonal functional moiety. These incorporated analogs are detected using methods known in the art. For the halogenated nucleoside analogs, antibodies that selectively recognize the particular halogen moiety are used, which either comprise a label or are detected by a second antibody that comprises a label. The nucleoside analogs that comprise a bioorthogonal functional moiety are detected using reagents comprising a complimentary bioorthogonal functional moiety and a label, resulting in covalent attachment of the labeling reagent to the nucleoside analog.

This dual labeling method for measuring cell proliferation is distinguished from known methods because 1) no wash treatment is required between the two pulses and 2) the compatibility of the two pulse labeling conditions for detection by two color, a first and second label, fluorescence measurement, wherein one of the nucleoside analogs comprises a bioorthogonal functional moiety. The first and second labels are preferably selected such that they produce distinguishable detectable signals, in other words the labels can be excited at the same or at different wavelengths, but the emission is at different wavelengths.

In one particular aspect when using two thymidine analogs, the first pulsed nucleoside, 5-ethynyl 2'-deoxyuridine (also termed herein ethynyluracil or EdU) does not need to be removed from the test system (cell culture or animal) when BrdU is added because EdU does not appear to incorporate into nucleic acid when in the presence of BrdU. This important feature, and previously undisclosed feature of the nucleoside analogs, allows for uninterrupted observation of baseline cell proliferation measurements followed by the altered state of cell proliferation incurred by the administration of a specific treatment.

Nucleoside and Nucleotide Analogs:

Both nucleoside and nucleotide analogs can be used in the present methods for measuring nascent nucleic acid synthesis. Nucleosides are typically used in experiments wherein the analogs are added to cell culture or administered to animals because the nucleoside analogs are easily taken up by live cells, wherein they are phosphorylated into a nucleotide and then incorporated into a growing nucleic acid polymer. In contrast nucleotides are labile and prone to enzyme cleave, either before or after incorporation into cells, and are generally less stable than nucleosides. In addition, due to the additional charges from the phosphate groups, nucleotides are not easily transported into live cells and generally require a transfection step to get a sufficient concentration of nucleotides across the cellular membrane. This is not ideal for either in vivo or ex vivo/in vivo experiments where cell perturbation should be kept to a minimum to accurately interpret results. For these reasons, the following disclosure generally refers to nucleosides as the analog that is added to cells or animals, however this in no way is intended to be limiting, wherein nucleotides are equally as important.

The nucleoside analogs can be an analog for any of the four DNA bases (adenine (A), cytosine (C), guanine (G) or thymine (T)) or any of the four RNA bases (adenine (A), cytosine (C), guanine (G) or uracil (U)) and include their triphosphate and phosphoramidite forms, wherein these analogs are incorporated into newly synthesized nucleic acid by polymerase present in the cells. The nucleosides are modified into analogs wherein they comprise a moiety that is ultimately used for detection of that nucleoside and the resulting nascent nucleic acid polymer synthesized in the presence of the nucleoside analogs.

In one embodiment the nucleoside analog is a halogenated analog, including but not limited to a bromo, chloro, and iodo moiety. In another embodiment the nucleoside analog comprises a chemical handle or bioorthogonal functional moiety, including but not limited to an azido, alkyne and phosphine moiety. Halogenated analogs are well known in the art, e.g. BrdU, IdU, CldU and BrUTP, and can be purchased from a number of vendors (Sigma, Saint Louis, Mo.; Millipore, Billerica, Mass.; Anaspec, San Jose, Calif.; Invitrogen, Carlsbad, Calif.) Similarly the antibodies used to detect these analogs are also commercially available (Dako, Carpinteria, Calif.; BD Bioscience, San Diego, Calif.; EMD Biosciences, Madison, Wis.).

The nucleoside analogs that comprise a bioorthogonal functional moiety which are suitable for use in the methods described herein include any nucleoside analogue, as defined herein, that contains a reactive bioorthogonal moiety, or chemical handle, that can undergo a [3+2] cycloaddition or Staudinger ligation. In some embodiments, the reactive bioorthogonal moiety is carried by the base of the nucleoside. The base carrying the reactive bioorthogonal moiety can be a purine (e.g., adenine or guanine) or a pyrimidine (e.g., cytosine, uracil or thymine). In certain embodiments, the base is uracil; in some such embodiments, uracil carries the reactive bioorthogonal moiety on the 5-position. In certain embodiments, the base is adenine; in some such embodiments, adenine carries the reactive bioorthogonal moiety. In certain embodiments, the bioorthogonal moiety is indirectly attached to the base, while in other embodiments the bioorthogonal moiety is directly covalently attached to the base. Non-limiting examples of the nucleoside analogues that may be used in the methods described herein include ethynyluracil or EdU and 5-azido-2'-deoxyuracil (also termed herein azidouracil or AzdU) as well as their triphosphate and phosphoramidite forms. EdU can be synthesized essentially as described by C.-S. Yu and F. Oberdorfer, Synlett, 2000, 1:86-88; and AzdU can be synthesized using a method similar to that described in P. Sunthankar et al., Anal. Biochem., 1998, 258:195-201 to synthesize azido-dUMP. EdU is also commercially available from Berry and Associates, Inc. (Dexter, Mich.). In certain embodiments, the reactive bioorthogonal moiety is carried by the sugar (ribose and deoxyribose) of the nucleoside. In certain embodiments, the bioorthogonal moiety is indirectly attached to the sugar, while in other embodiments the bioorthogonal moiety is directly and covalently attached to the sugar. In certain embodiments, the reactive bioorthogonal moiety attached to the phosphate moiety of the nucleoside. The sugar carrying the reactive bioorthogonal moiety can be covalently attached to a purine (e.g., adenine or guanine) or a pyrimidine (e.g., cytosine, uracil or thymine). In certain embodiments, the base is uracil, while in other embodiments the base is adenine. Non-limiting examples of the nucleoside analogues that may be used in the methods described herein include EdU, AzdU, or chain terminating dideoxy compounds such as AZT; 3'-Azido-2',3'-dideoxyadenosine, 3'-Azido-3'-deoxythymidine (AZT), 5'-Azido-5'-deoxythymidine, 5-(1-ethynyl)-2'-O-methyluridine, 5-(1-propynyl)-2'-deoxyuridine, 5-(propargyloxy)-2'-deoxyuridine, 8-Azido-2'-deoxyadenosine, 3'-Azido-2',3'-dideoxyadenosine.

The reactive bioorthogonal moiety or chemical handle can be a 1,3-dipole such as a nitrile oxide, an azide, a diazomethane, a nitrone or a nitrile imine. In certain embodiments, the 1,3-dipole is an azide. Alternatively, the reactive bioorthogonal functional moiety can be a dipolarophile such as an alkene (e.g., vinyl, propylenyl, and the like) or an alkyne (e.g., ethynyl, propynyl, and the like). In certain embodiments, the dipolarophile is an alkyne, such as, for example, an ethynyl group.

These bioorthogonal functional moieties described above are non-native, non-perturbing bioorthogonal chemical moieties that possess unique chemical functionality that can be modified through highly selective reactions. In particular these incorporated nucleosides are labeled using labeling reagents which comprise a chemical handle that will selectively form a covalent bond with the nucleoside in the presence of the cellular milieu.

Labeling Reagents:
Reagent A
In a particular embodiment, the labeling reagent is a first antibody, which may be conjugated to a label or bound by a second antibody that is covalently attached to a label, wherein the first antibody binds to the incorporated nucleoside. In one aspect this is an anti-BrdU antibody. In anther aspect the antibody is an anti-IdU or anti-CldU antibody. However, other antibodies which could selectively bind to incorporated nucleoside analogs are also envisioned.
Reagent B
In another embodiment, the labeling reagent comprises a label and a chemical handle. A chemical handle, as defined above, is a bioorthogonal functional moiety that selectively reacts with a functional moiety to form a covalent bond.
Labels
As already mentioned above, the role of a label is to allow visualization or detection of a nucleic acid polymer, e.g., DNA in a cell, following labeling. Preferably, a label (or detectable agent or moiety) is selected such that it generates a signal which can be measured and whose intensity is related (e.g., proportional) to the amount of labeled nucleic acid polymer, e.g., in a sample being analyzed.

A label used in a labeling reagent in the methods and compositions described herein, is any chemical moiety, organic or inorganic, that exhibits an absorption maximum at wavelengths greater than 280 nm, and retains its spectral properties when covalently attached to a modified nucleoside such as, by way of example only, an azide, and alkyne or a phosphine. Fluorophores used in the labeling reagent in the methods and compositions described herein include, without limitation; a pyrene (including any of the corresponding derivative compounds disclosed in U.S. Pat. No. 5,132,432), an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine (including any corresponding compounds in U.S. Ser. Nos. 09/968,401 and 09/969,853), a carbocyanine (including any corresponding compounds in U.S. Ser. Nos. 09/557,275; 09/969,853 and 09/968,401; U.S. Pat. Nos. 4,981,977; 5,268,486; 5,569, 587; 5,569,766; 5,486,616; 5,627,027; 5,808,044; 5,877, 310; 6,002,003; 6,004,536; 6,008,373; 6,043,025; 6,127, 134; 6,130,094; 6,133,445; and publications WO 02/26891, WO 97/40104, WO 99/51702, WO 01/21624; EP 1 065 250 A1), a carbostyryl, a porphyrin, a salicylate, an anthranilate, an azulene, a perylene, a pyridine, a quinoline, a borapolyazaindacene (including any corresponding compounds disclosed in U.S. Pat. Nos. 4,774,339; 5,187,288; 5,248,782; 5,274,113; and 5,433,896), a xanthene (including any corresponding compounds disclosed in U.S. Pat. Nos. 6,162,931; 6,130,101; 6,229,055; 6,339,392; 5,451,343 and U.S. Ser. No. 09/922,333), an oxazine (including any corresponding compounds disclosed in U.S. Pat. No. 4,714, 763) or a benzoxazine, a carbazine (including any corresponding compounds disclosed in U.S. Pat. No. 4,810,636), a phenalenone, a coumarin (including an corresponding compounds disclosed in U.S. Pat. Nos. 5,696,157; 5,459, 276; 5,501,980 and 5,830,912), a benzofuran (including an corresponding compounds disclosed in U.S. Pat. Nos. 4,603, 209 and 4,849,362) and benzphenalenone (including any corresponding compounds disclosed in U.S. Pat. No. 4,812, 409) and derivatives thereof. As used herein, oxazines include resorufins (including any corresponding compounds disclosed in U.S. Pat. No. 5,242,805), aminooxazinones, diaminooxazines, and their benzo-substituted analogs.

Xanthene type fluorophores used in labeling reagents in the methods and compositions described herein include, but are not limited to, a fluorescein, a rhodol (including any corresponding compounds disclosed in U.S. Pat. Nos. 5,227, 487 and 5,442,045), or a rhodamine (including any corresponding compounds in U.S. Pat. Nos. 5,798,276; 5,846, 737; U.S. Ser. No. 09/129,015). As used herein, fluorescein includes benzo- or dibenzofluoresceins, seminaphthofluoresceins, or naphthofluoresceins. Similarly, as used herein rhodol includes seminaphthorhodafluors (including any corresponding compounds disclosed in U.S. Pat. No. 4,945, 171). In certain embodiments, the fluorophore is a xanthene that is bound via a linkage that is a single covalent bond at the 9-position of the xanthene. In other embodiments, the xanthenes include derivatives of 3H-xanthen-6-ol-3-one attached at the 9-position, derivatives of 6-amino-3H-xanthen-3-one attached at the 9-position, or derivatives of 6-amino-3H-xanthen-3-imine attached at the 9-position.

In certain embodiments, the fluorophores used in the labeling reagent in the methods and compositions described herein include xanthene (rhodol, rhodamine, fluorescein and derivatives thereof) coumarin, cyanine, pyrene, oxazine and borapolyazaindacene. In other embodiments, such fluorophores are sulfonated xanthenes, fluorinated xanthenes, sulfonated coumarins, fluorinated coumarins and sulfonated cyanines. Also included are dyes sold under the tradenames, and generally known as Alexa Fluor, DyLight, Cy Dyes, BODIPY, Oregon Green, Pacific Blue, IRDyes, FAM, FITC, and ROX.

The choice of the fluorophore attached for the labeling reagent will determine the absorption and fluorescence emission properties of the modified nucleic acid. Physical properties of a fluorophore label that can be used for detection of modified nucleic acids include, but are not limited to, spectral characteristics (absorption, emission and stokes shift), fluorescence intensity, lifetime, polarization and photo-bleaching rate, or combination thereof. All of these physical properties can be used to distinguish one fluorophore from another, and thereby allow for multiplexed analysis. In certain embodiments, the fluorophore has an absorption maximum at wavelengths greater than 480 nm. In other embodiments, the fluorophore absorbs at or near 488 nm to 514 nm (particularly suitable for excitation by the output of the argon-ion laser excitation source) or near 546 nm (particularly suitable for excitation by a mercury arc lamp). In other embodiment a fluorophore can emit in the NIR (near infra red region) for tissue or whole organism applications. Other desirable properties of the fluorescent labeling reagent may include cell permeability and low toxicity, for example if labeling of the nucleic acid polymer is to be performed in a cell or an organism (e.g., a living animal).

In certain embodiments the labeling reagent comprises a tandem dye or FRET dye pair. This is particularly useful to obtain a set of labeling reagents that are excited at the same wavelength but which have distinct emission spectra. Two dyes function as a FRET pair when they are within close proximity, usually covalently attached, so that the energy from the excited first dye (the donor) is transferred the second dye (the acceptor) where the energy is then emitted at a longer wavelength than would have been possible by excitation only of the first dye. A particularly useful combination is the FRET dye pairs disclosed in U.S. Pat. Nos. 7,169,939; 6,849,745; 5,945,526; 5,863,727; 5,800,996; and 6,967,250.

In another embodiment the labeling reagent comprises a fluorescent nanocrystal.

For each dual labeling experiment a matched set of labeling reagents must be selected based on the instrument being used and so that the dyes can be appropriately excited and measured at the correct wavelengths to distinguish between the baseline nucleic acid synthesis and the subsequent change in nucleic acid synthesis due to treatment. Matched pairs of fluorescent labeling dyes typically produce signals that are spectrally distinguishable. For example, in some embodiments, the fluorescent dyes in a matched pair do not significantly absorb light in the same spectral range (i.e., they exhibit different absorption maxima wavelengths) and can be excited (for example, sequentially) using two different wavelengths. Alternatively, the fluorescent dyes in a matched pair may emit light in different spectral ranges (i.e., they produce a dual-color fluorescence upon excitation). Pairs of fluorescent labels are known in the art (see, for example, R. P. Haugland, "*Molecular Probes: Handbook of Fluorescent Probes and Research Chemicals*, supra).

The selection of a particular set of labels will depend on the purpose of the labeling to be performed and will be governed by several factors, such as the ease and cost of the labeling method, the quality of sample labeling desired, the effects of the detectable moiety on the cell or organism, the nature of the detection system, the nature and intensity of the signal generated by the detectable moiety, and the like. In this particular instance, one label is selected for Reagent A and the second label is selected for Reagent B.

Methods:

The above dual labeling components are used in the present methods to measure cellular nascent nucleic acid synthesis by dual pulse labeling of the cellular nucleic acid. The first pulse labeling of nucleic acid with a nucleoside analog allows establishment of a baseline rate of nucleic acid synthesis. Pulse labeling of nucleic acid with an additional second nucleoside analog then allows measurement of any changes to the nucleic acid synthesis. This method does not require a potentially artifact-inducing intermediary wash step between pulse labels. The nucleic acid synthesis can be measured as cell proliferation, in the case of DNA, or in gene expression, in the case of RNA. Additionally, this method may be used to screen compounds for their effect on cellular proliferation or gene expression by treating cells or an organism with the test compound simultaneous to or before treatment with a second nucleoside analog.

Thus, in one embodiment is provided a method for measuring a change in cellular nucleic acid synthesis, wherein the method comprises:
   a) incubating a sample with an effective amount of a first nucleoside or nucleotide analog to form a primary incubated sample;
   b) incubating the primary incubated sample with at least one second nucleoside or nucleotide analog to form a secondary incubated sample;
   c) incubating the secondary incubated sample with a first labeling reagent and at least one second labeling reagent to form a labeled sample;
   d) detecting the labeled sample wherein a level of incorporation of the first and at least one second nucleoside or nucleotide analog is measured,
      wherein a difference in a level of incorporation of the at least one second nucleoside or nucleotide analog relative to the level of incorporation of the first nucleoside or nucleotide analog is measured as a change in cellular nucleic acid synthesis,
      with the proviso that either the first nucleoside or nucleotide or the at least one second nucleoside or nucleotide contains a bioorthogonal functional moiety.

Thus, in one aspect is provided a method for measuring a change in cellular DNA synthesis, which can be measured as cell proliferation. In another aspect is provided a method for measuring a change in cellular RNA synthesis, which can be measure as gene expression.

In certain preferred embodiments of the present invention, a method for screening test compounds for their effect on cellular proliferation is provided. This method may include measuring cellular proliferation changes in a patient during the course of treatment for a disease with a specific compound.

Cancer cells could be removed from a patient and grown in culture. A baseline DNA synthesis rate can be determined with the first pulse, then a drug is added along with the second nucleoside analog and the change of DNA synthesis rate determined, which in the case of drug resistance/sensitivity in cancer cells would easily be determined. Screens for compounds which either stimulate or block DNA synthesis at various places in the cell cycle could be greatly improved by the addition having an accurate baseline synthesis measurement which does not alter the state of the cell proliferation.

For example, breast cancer cells may be removed from a patient and grown in culture. The baseline cellular proliferation rate may be established by adding a first pulse of EdU. Then, the cells may be treated with a chemotherapy drug, for example tamoxifen, and treated with a second pulse label of BrdU. The cellular proliferation rate in response to tamoxifen is then measured by comparing incorporation of EdU to BrdU. This process may be repeated over the course of the breast cancer patient's treatment to ensure that the patient's cancer cells remain responsive to the chosen chemotherapeutic agent, in this case, tamoxifen. In this present example, the clinician would be looking for a decrease in cellular proliferation upon treatment with the chemotherapy drug. Once the dual pulse labeling of DNA in the breast cancer patient's cells demonstrated no change in cellular proliferation upon treatment with a particular drug, the clinician could reevaluate whether the patient would benefit from continued treatment with that drug or should be switched to a different chemotherapeutic agent.

One of skill in the art will recognize that this method can be adapted to screen compounds for their effect on cellular proliferation in a number of diseases. As examples, and not intended to limit the scope of the present invention, the following are diseases whose progression is affected by alterations to the normal level of cellular proliferation: breast cancer, leukemia, colon cancer, prostate cancer, and the like (see, e.g., U.S. Pat. No. 6,646,008 (filed Feb. 22, 2000)); neural diseases, including neurodegenerative diseases, for example, Huntington's disease (Curtis et al., *Increased Cell Proliferation and Neurogenesis in the Adult Human Huntington's disease brain,* 100 (15) PNAS 9023-9027 (Jul. 22, 2003)), or HIV-associated dementia (Okamoto et al., *HIV/gp120 Decreases Adult Neural Progenitor Cell Proliferation via Checkpoint Kinase-Mediated Cell-Cycle Withdrawal and G1 Arrest,* 1 Cell Stem Cell 230-236 (Aug. 16, 2007)); and other hyperplasia diseases including, psoriasis, seborrhea, eczema, benign prostate hyperplasia, congenital adrenal hyperplasia, endometrial hyperplasia, squamous cell hyperplasia, sebaceous hyperplasia, Crohn's disease, carcinoma, sarcoma, glioma and lymphoma (see U.S. Pat. No. 7,256,034 (filed Jan. 5, 2004)).

In still further embodiments, the present invention concerns a method for identifying new compounds, which may be termed as "test compounds", which have a desired effect on cellular proliferation. Depending on the application, this desired effect may be to stimulate, to inhibit, or to not affect cellular proliferation.

In screening methods to identify whether test compounds have an effect on cellular proliferation, it is proposed that compounds isolated from natural sources such as plants, animals or even sources such as marine, forest or soil samples, may be assayed for the presence of potentially useful pharmaceutical agents. It will be understood that the test compounds to be screened could also be derived from chemical compositions or man-made compounds. The test compounds may also include proteins and peptides, such as those derived from recombinant DNA technology or by other means, including peptide synthesis. The test compounds may also be antibodies, including polyclonal and monoclonal antibodies. The test compounds may also include fragments or parts of naturally-occurring compounds or may be only found as active combinations of known compounds which are otherwise inactive. The test compounds may also include nucleic acids, including, but not limited to: DNA; ribonucleic acid (RNA); small interfering RNAs (siRNA); and single-stranded nucleic acids, more particularly, those designed to form in vivo triplexes.

In certain embodiments, the present invention may be used to measure cellular proliferation following treatment with compounds known to affect cellular proliferation. See, e.g., Nicholas R. Cozzarelli, *The Mechanism of Action of Inhibitors of DNA Synthesis,* 46 ANN. REV. BIOCHEM. 641-648 (1977).

In certain embodiments of the present invention, the test compound is administered to an organism. Organisms to which the claimed methods may be applied include, but are not limited to: humans, mice, rats, horses, cows, sheep, rabbits, dogs, or cats.

Test compounds and nucleoside analogs may be administered to organisms by a variety of methods known to persons of skill in the art. These include oral administration (e.g. ingestion of a pill, food or liquid containing the test compound and/or nucleoside analogs), or by subcutaneous, intravenous or intraperitoneal administration (e.g. by injection or topical application). The test compound may also be administered parenterally, intraspinally, or intracerebrally.

In certain embodiments, the present invention provides for measuring cellular proliferation in cells, rather than an organism. The nucleoside analogs may be added to the medium in which the cells are grown. Similarly, if the method includes screening test compounds for their effect on cellular proliferation, the test compound may be added to the medium in which the cells are grown.

The preceding discussion of test compounds effect on cell proliferation is also intended to relate to their effect on gene expression wherein the change in RNA synthesis is measure.

In a specific embodiment of the present invention, cellular proliferation is measured in a cell by treating the cell with an effective amount of EdU, followed by treatment with an effective amount of BrdU. The EdU pulse label is detected using click chemistry reagents, including copper sulfate ($CuSO_4$) and a dye-labeled azide (e.g. Alexa Fluor® 488-azide (Molecular Probes™/Invitrogen™, Carlsbad, Calif.)). The BrdU pulse label is detected using standard antibody-based methods. See, e.g., Jonathon Pines et al., *Assays for CDK Activity and DNA Replication in the Cell Cycle,* CURRENT PROTOCOLS IN CELL BIOLOGY (Juan S. Bonifacino et al. eds., John Wiley & Sons, Inc. 2003) (1998). Both labels are then measured using flow cytometry.

In certain embodiments of the present invention, this dual pulse labeling method may be applied to the assessment of cancer therapy ex vivo or in vivo. Cancer cells may be removed from a patient and grown in culture. A baseline DNA synthesis rate may be determined with the first pulse, then a drug is added along with the second nucleoside analog and the change of DNA synthesis rate determined. Having an accurate baseline synthesis measurement which does not alter the state of the cellular proliferation will greatly improve screening methods for compounds that either stimulate or block DNA synthesis.

In certain embodiments of the present invention, the method for measuring cellular proliferation is performed on a neural cell. This dual pulse labeling method may be applied to the assessment of treatment for nervous system diseases. For instance, changes to cellular proliferation rates of neural cells upon treatment with a test compound may be measured by contacting neural cells with a first pulse of a nucleoside analog; treating with a test compound; contacting the neural cells with a competitive nucleoside analog simultaneous to or after treatment with the test compound; detecting incorporation of the first nucleoside analog and detecting incorporation of the competitive nucleoside analog. Thus, this dual pulse labeling method may be used to identify compounds that either stimulate or inhibit neural cell proliferation.

In one embodiment of the present invention, compounds are screened for their effects on cellular proliferation using a method comprising the steps of: treating a cell with a first nucleoside analog; treating the cell with a test compound; treating the cell with at least one competitive nucleoside analog simultaneous to or after treating the cell with the test compound; detecting incorporation of the first nucleoside analog; and detecting incorporation of the second nucleoside analog.

In another embodiment of the present invention, cellular proliferation in an organism is measured by: treating an organism with a first nucleoside analog; treating the organism with at least one second nucleoside analog; detecting incorporation of the first nucleoside analog; and detecting incorporation of the second nucleoside analog.

In another embodiment of the present invention, cellular proliferation in an organism is measured by: treating an organism with a first nucleoside analog; treating the organism with a test compound; treating the organism with at least one competitive nucleoside analog simultaneous to or after treating the cells with the test compound; detecting incorporation of the first nucleoside analog; and detecting incorporation of the second nucleoside analog.

Illumination

The compounds of the invention may, at any time after or during an assay, be illuminated with a wavelength of light that results in a detectable optical response, and observed with a means for detecting the optical response. Upon illumination, such as by an violet or visible wavelength emission lamp, an arc lamp, a laser, or even sunlight or ordinary room light, the fluorescent compounds display intense visible absorption as well as fluorescence emission. Selected equipment that is useful for illuminating the fluorescent compounds of the invention includes, but is not limited to, hand-held ultraviolet lamps, mercury arc lamps, xenon lamps, argon lasers, laser diodes, and YAG lasers. These illumination sources are optionally integrated into laser scanners, flow cytometer, fluorescence microplate readers, standard or mini fluorometers, or chromatographic detectors. This fluorescence emission is optionally detected by visual inspection, or by use of any of the following devices: CCD cameras, video cameras, photographic film, laser scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, a fluorescence microscope or a fluorometer, the instrument is optionally used to distinguish and discriminate between the first pulse labeling reagent of the invention and a second labeling reagent detectably different optical properties, typically by distinguishing the fluorescence response of the first fluorescent compounds of the invention from that of the second fluorophore. Where a sample is examined using a flow cytometer, examination of the sample optionally includes isolation of particles within the sample based on the fluorescence response by using a sorting device.

Kits of the Invention

In another aspect, the present invention provides kits that includes at least one nucleoside analog and labeling reagent of the invention. The kit will generally also include instructions for using the nucleoside analog and labeling reagent in one or more methods, typically for measuring a change in cellular nucleic acid synthesis.

In an exemplary embodiment, the kit includes a first nucleoside or nucleotide analog, at least one second nucleoside or nucleotide analog, wherein in at least the first analog or the at least one second nucleoside or nucleotide analog contains a bioorthogonal functional moiety, a first labeling reagent and a second labeling reagent. Additional kit components include buffers, other detection reagents and standards.

A detailed description of the invention having been provided above, the following examples are given for the purpose of illustrating the invention and shall not be construed as being a limitation on the scope of the invention or claims.

EXAMPLES

The following examples describe some of the preferred embodiments of the present invention. However, it should be understood that these examples are for illustrative purposes only and are not meant to limit the scope of the invention.

Example 1

A standard method of preparing cultured cells for the measurement of newly synthesized DNA (cellular proliferation) is set up according to known conditions for cells to be actively growing by providing the proper media and nutrient requirements. In the present example, Jurkat cell cultures were diluted one to four to a density of $2\times10^5$ cells/ml. After these cells had been growing for two or three days, the first nucleoside analog, EdU, was added at 20 µM, a concentration appropriate for incorporation in the DNA of cells undergoing DNA synthesis. The cells were grown in the presence of EdU for thirty minutes. After thirty minutes of growth and without the removal of EdU through the washing of the cells in fresh media, an appropriate amount of the competitive nucleoside analog, BrdU, was added at a 10 µM concentration, and the cells were grown for thirty minutes. The cells were then harvested, washed, fixed with 70% ice-cold ETOH and stored at 4° C. for 96 hours. The cells were then washed and resuspended in 4M HCL for 20 minutes at room temperature. A phosphate/citric acid buffer was added, and the cells were washed twice and resuspended in 0.1% Triton® X-100/1% BSA/PBS at $1\times10^7$/ml. Then, labeling of the EdU was performed by adding click chemistry based reagents, including a solution comprised of $CuSO_4$ in Tris-buffered saline and Alexa Fluor® 488-azide (495 nm excitation maxima/519 nm emission maxima) (Molecular Probes®/Invitrogen™, Carlsbad, Calif.). The cells were then washed with 0.1% Triton® X-100/1% BSA/ PBS. After this, labeling of the BrdU was performed using the anti-BrdU antibody Alexa Fluor® 647 conjugate (650 nm excitation maxima/670 nm emission maxima) (Molecular Probes®/Invitrogen™, Carlsbad, Calif.). To detect DNA content, a nucleic acid dye, SYTOX® Blue stain (444 nm excitation maxima/480 nm emission maxima) (Molecular Probes®/Invitrogen™, Carlsbad, Calif.) was added with RNase (Invitrogen™, Carlsbad, Calif.). Detection of the three labels was performed by flow cytometry. To detect the EdU label, 488 nm excitation was used, with a 530/30 nm bandpass. To detect the BrdU label, 633 nm excitation was used, with a 660/20 nm bandpass. To detect DNA content, 405 nm excitation was used, with a 450/50 nm bandpass.

Example 2

A standard method of preparing cultured cells for the measurement of newly synthesized DNA (cellular proliferation) is set up according to known conditions for cells to be actively growing by providing the proper media and nutrient requirements. In the present example, Jurkat cell cultures were diluted one to four to a density of $2 \times 10^5$ cells/ml. After these cells have been growing for two or three days the first nucleoside analog, EdU, was added at 20 µM, a concentration appropriate for incorporation in the DNA of cells undergoing DNA synthesis. The cells were grown in the presence of EdU for one hour. After one hour of growth and without the removal of EdU through the washing of the cells in fresh media, an appropriate amount of the competitive nucleoside analog, BrdU, was added at a 10 µM concentration, and the cells were grown for thirty minutes. The cells were then harvested, washed, fixed with 70% ice-cold ETOH and stored at 4° C. for 96 hours. The cells were then washed and resuspended in 4M HCL for 20 minutes at room temperature. A phosphate/citric acid buffer was added, and the cells were washed twice and resuspended in 0.1% Triton® X-100/1% BSA/PBS at $1 \times 10^7$/ml. Then, labeling of the EdU was performed by adding click chemistry based reagents, including a solution comprised of $CuSO_4$ in Tris-buffered saline and Alexa Fluor® 488-azide (495 nm excitation maxima/519 nm emission maxima) (Molecular Probes®/Invitrogen™, Carlsbad, Calif.). The cells were then washed with 0.1% Triton® X-100/1% BSA/PBS. After this, labeling of the BrdU was performed using the anti-BrdU antibody Alexa Fluor® 647 conjugate (650 nm excitation maxima/670 nm emission maxima) (Molecular Probes™/Invitrogen™, Carlsbad, Calif.). To detect DNA content, a nucleic acid dye, SYTOX® Blue stain (444 nm excitation maxima/480 nm emission maxima) (Molecular Probes®/Invitrogen™, Carlsbad, Calif.) was added with RNase (Invitrogen™, Carlsbad, Calif.). Detection of the three labels was performed by flow cytometry. To detect the EdU label, 488 nm excitation was used, with a 530/30 nm bandpass. To detect the BrdU label, 633 nm excitation was used, with a 660/20 nm bandpass. To detect DNA content, 405 nm excitation was used, with a 450/50 nm bandpass.

Results from Examples 1-2

Figure 1:
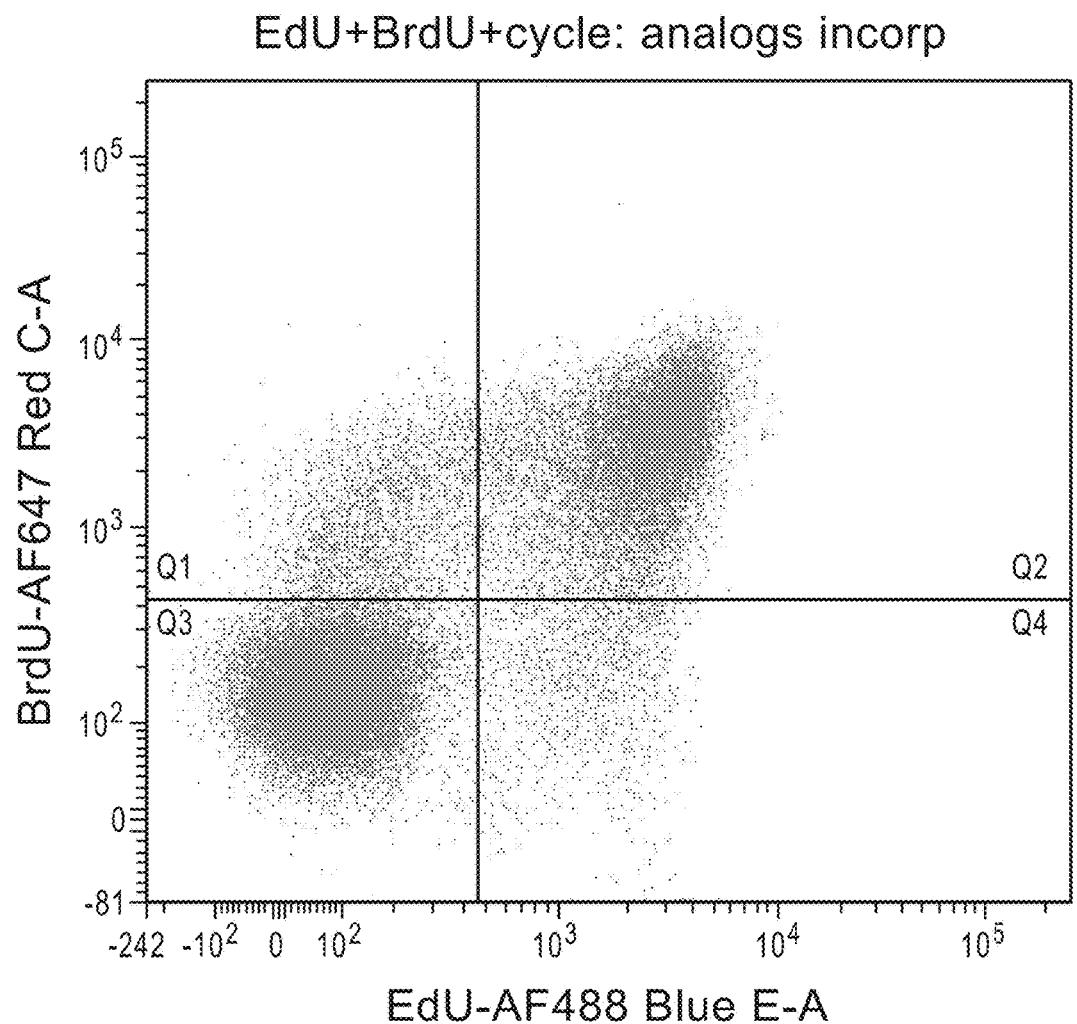
FIG. 1 presents a graph showing populations of cells treated with a first pulse label of EdU (10 μM) and a second pulse label of BrdU (10 μM), as detected by flow cytometry. The graph is divided into four quadrants with the first quadrant (Q1) located in the upper left hand corner, the second quadrant (Q2) located in the upper right hand corner, the third quadrant (Q3) located in the lower left hand corner, and the fourth quadrant (Q4) located in the lower right hand corner. Populations of cells in quadrant Q3 (lower left) are negative for both EdU (first pulse) and BrdU (second pulse). Populations of cells in quadrant Q2 (upper right) are positive for both EdU (first pulse) and BrdU (second pulse).
Figure 2A:
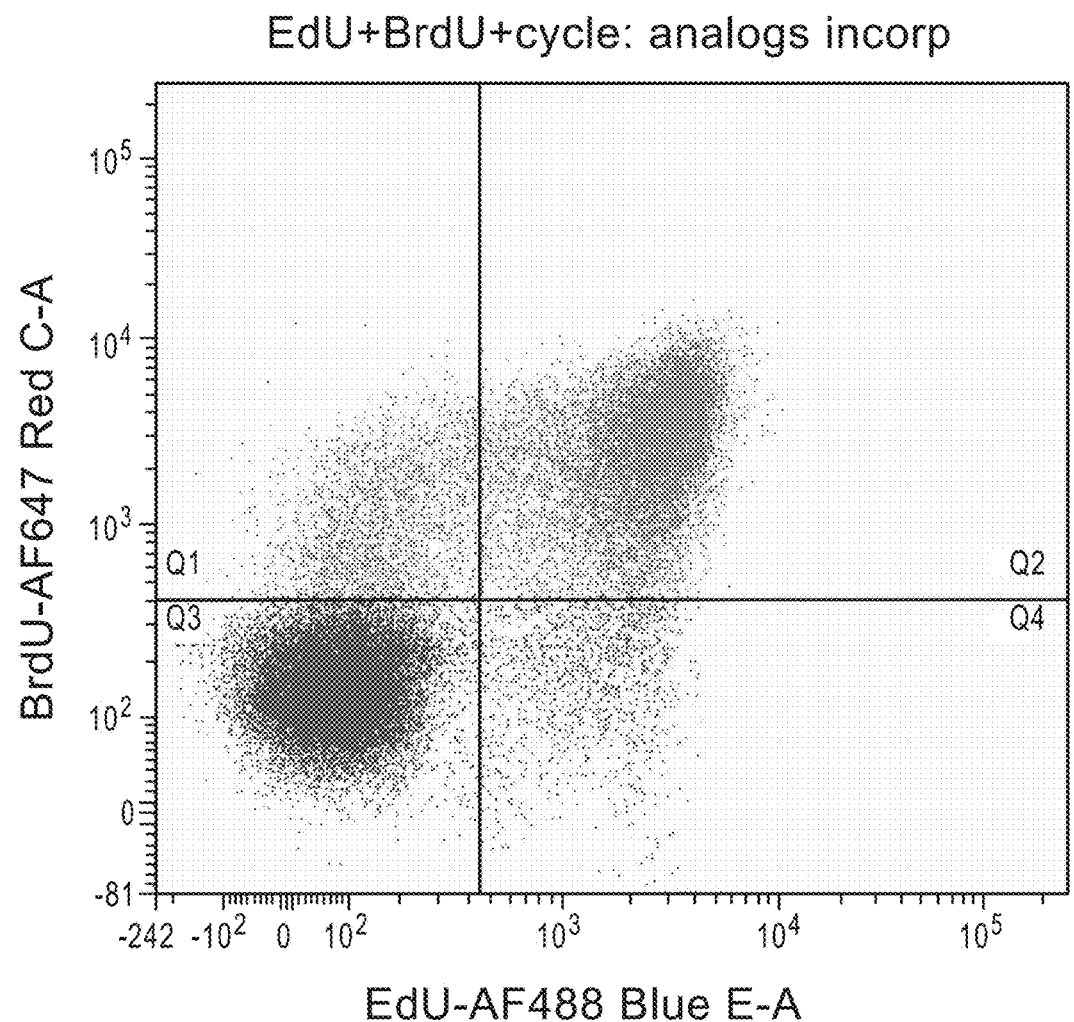
FIG. 2A, FIG. 2B and FIG. 2C present a series of graphs showing populations of cells treated with a first pulse label of EdU (10 μM) and a second pulse label of BrdU (10 μM) as detected by flow cytometry. The first graph (FIG. 2A) is divided into four quadrants with the first quadrant (Q1) located in the upper left hand corner, the second quadrant (Q2) located in the upper right hand corner, the third quadrant (Q3) located in the lower left hand corner, and the fourth quadrant (Q4) located in the lower right hand corner. Populations of cells in quadrant Q3 (lower left) are negative for both EdU (first pulse) and BrdU (second pulse). Populations of cells in quadrant Q2 (upper right) are positive for both EdU (first pulse) and BrdU (second pulse).
Figure 2B:
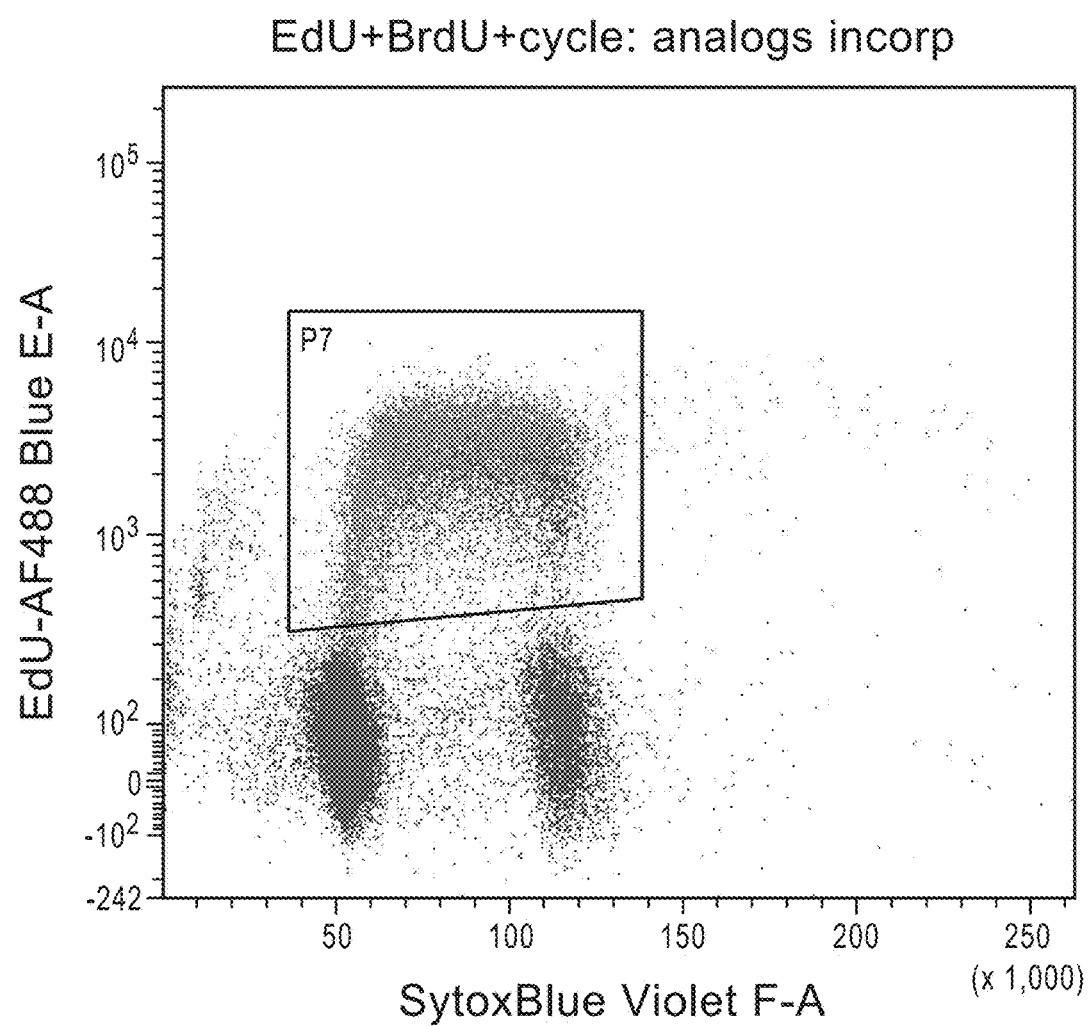
Figure 2C:
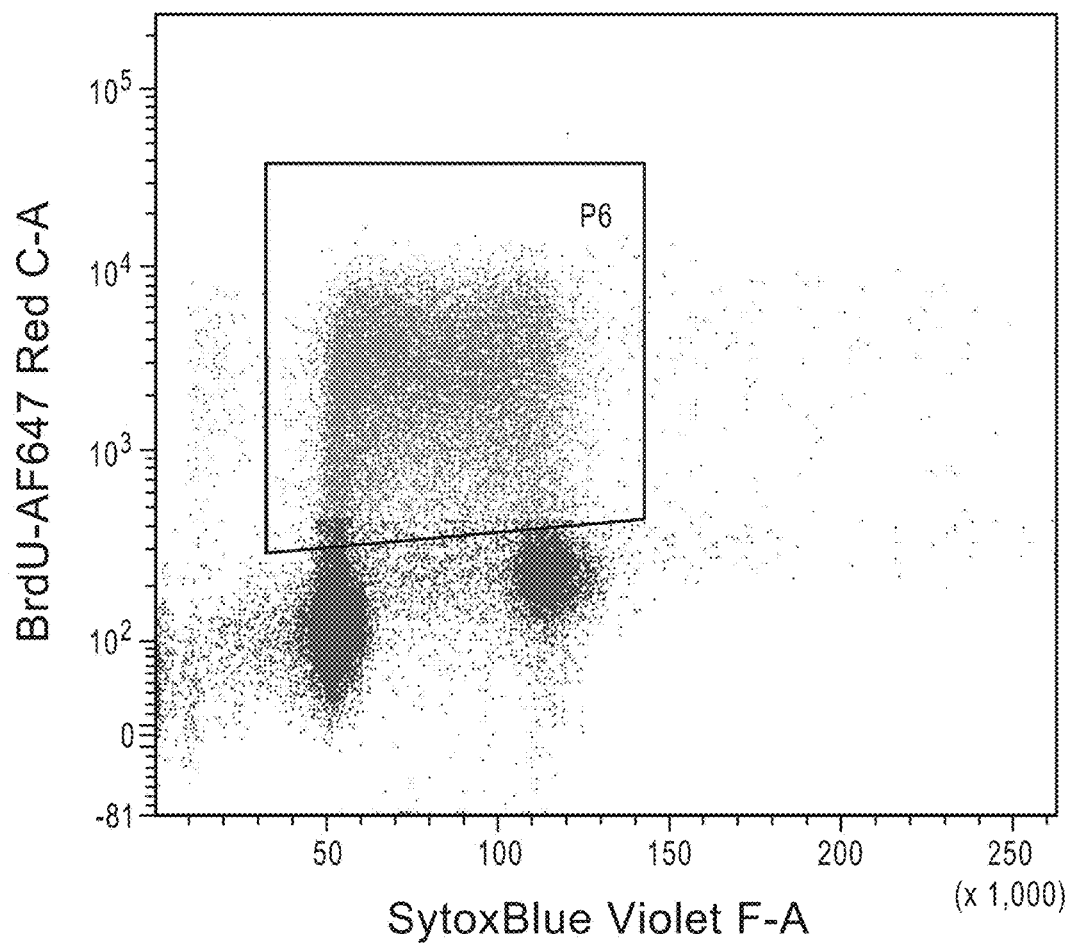
Figures 1, 3A:
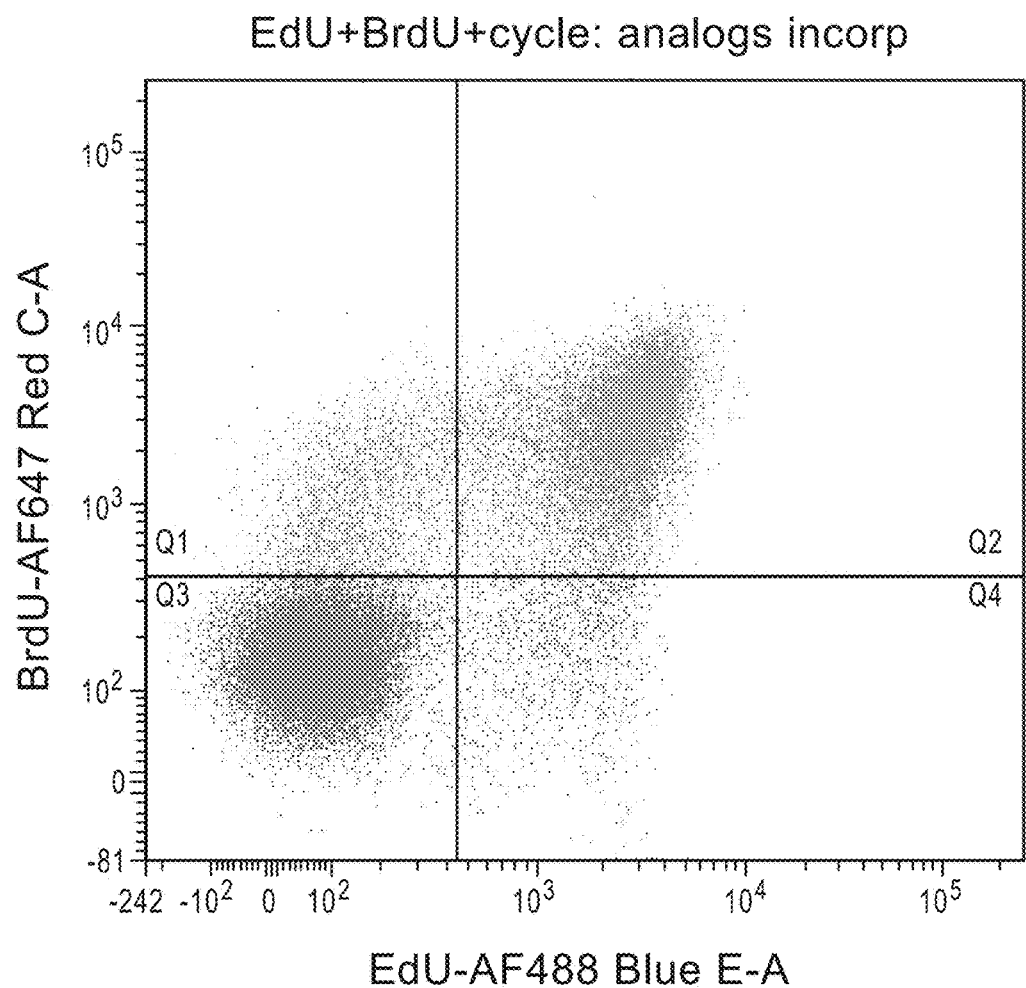
Figures 2, 3A:
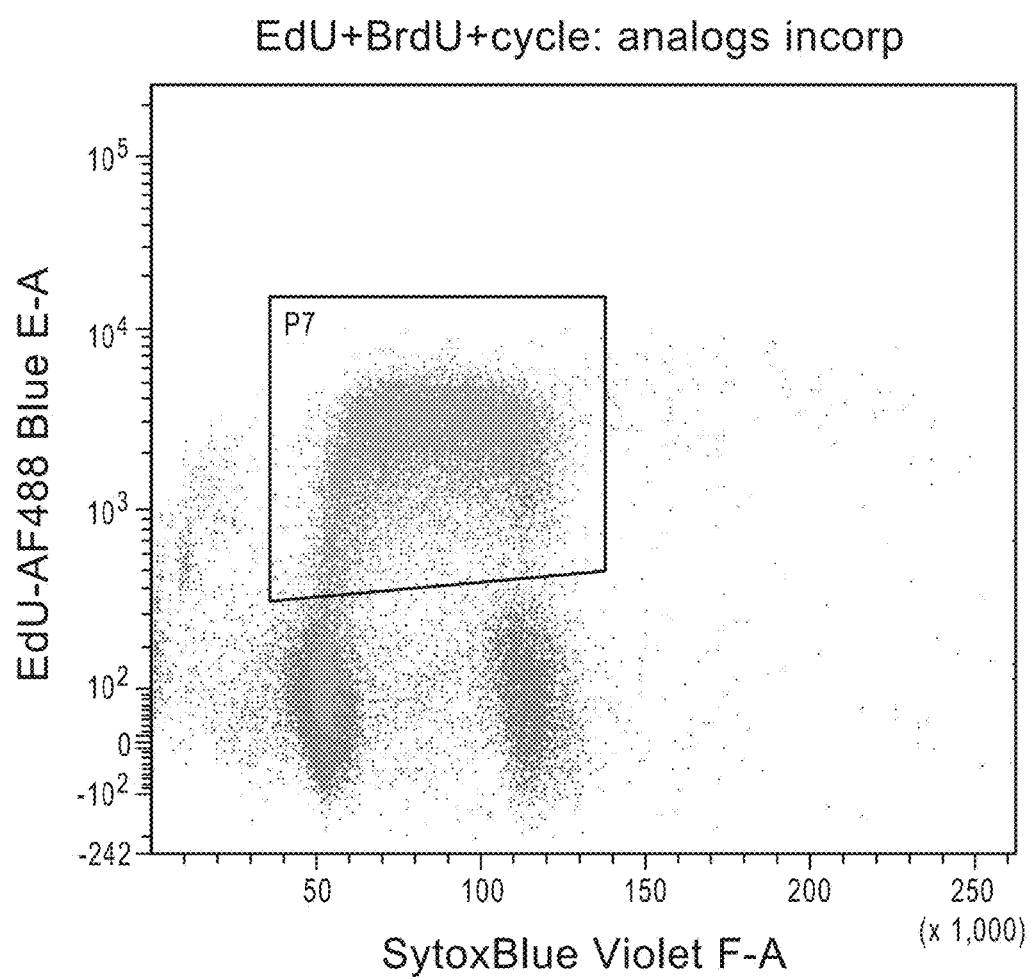
Figures 3, 3A:
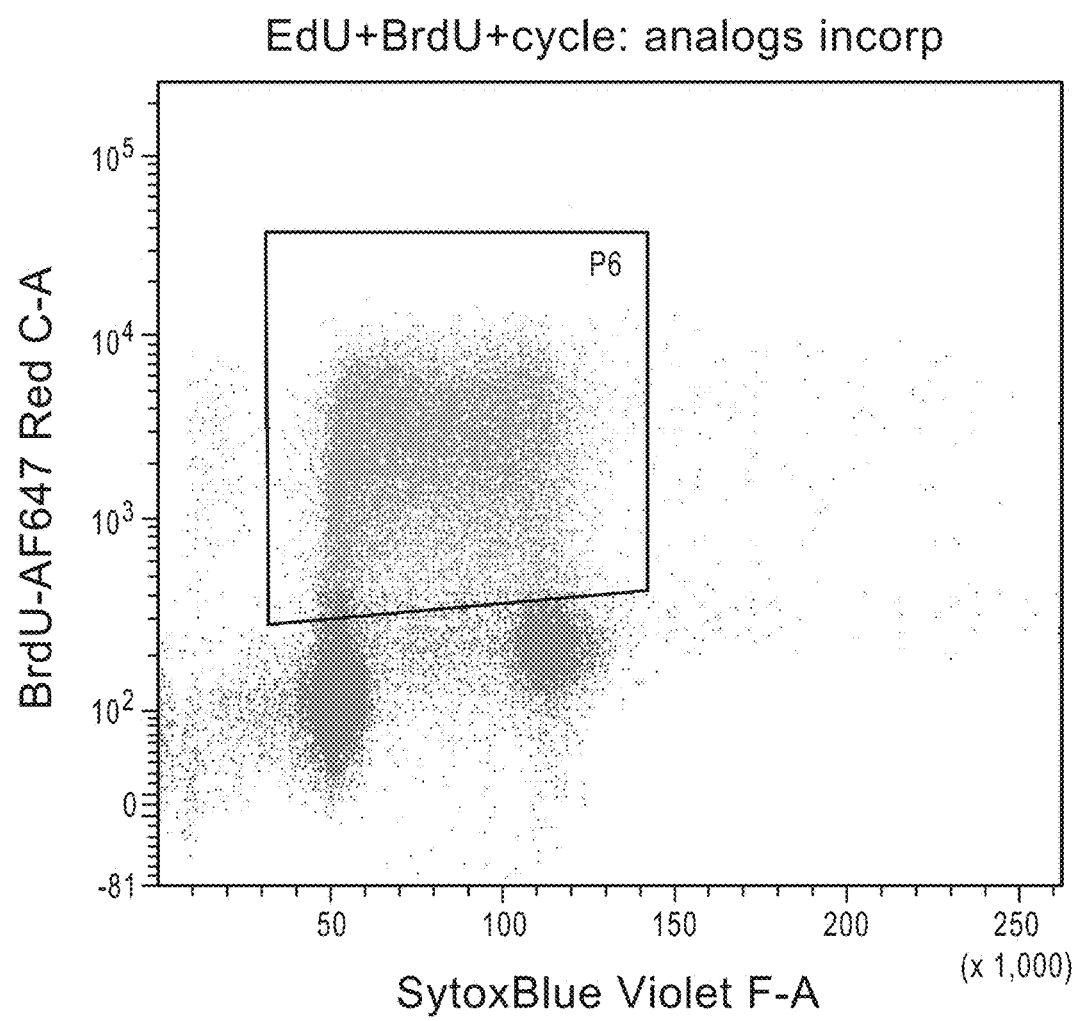
Figure 3B:
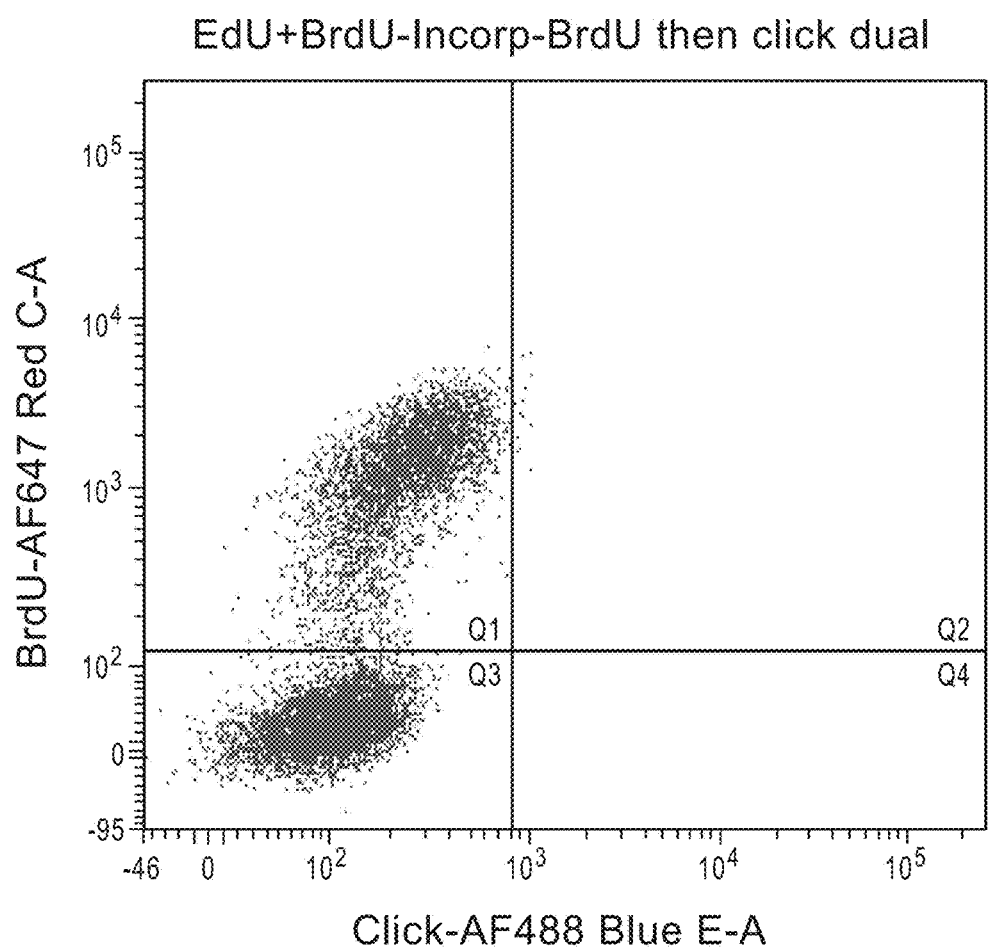
FIG. 3B presents a graph showing populations of cells treated with simultaneous pulse of EdU at a concentration of 20 μM and BrdU at a concentration of 10 μM as detected by flow cytometry. The graph is divided into four quadrants with the first quadrant (Q1) located in the upper left hand corner, the second quadrant (Q2) located in the upper right hand corner, the third quadrant (Q3) located in the lower left hand corner, and the fourth quadrant (Q4) located in the lower right hand corner. Populations of cells in quadrant Q3 (lower left) are negative for both EdU and BrdU. Populations of cells in quadrant Q2 (upper right) are positive for both EdU and BrdU. This plot shows there is only positive signal detected from the BrdU, and no signal detected from the EdU, demonstrating the BrdU is preferentially incorporated over EdU.
Figure 4A:
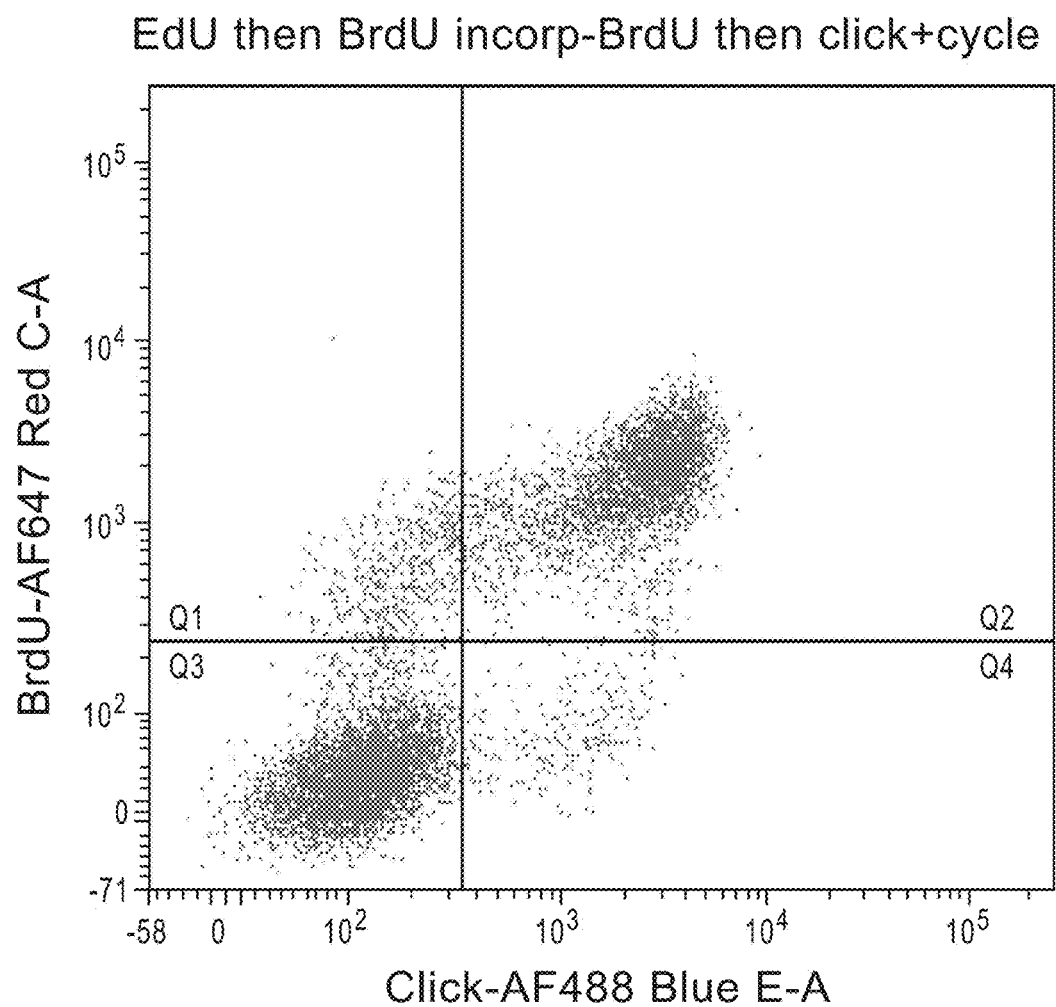
Figure 4C:
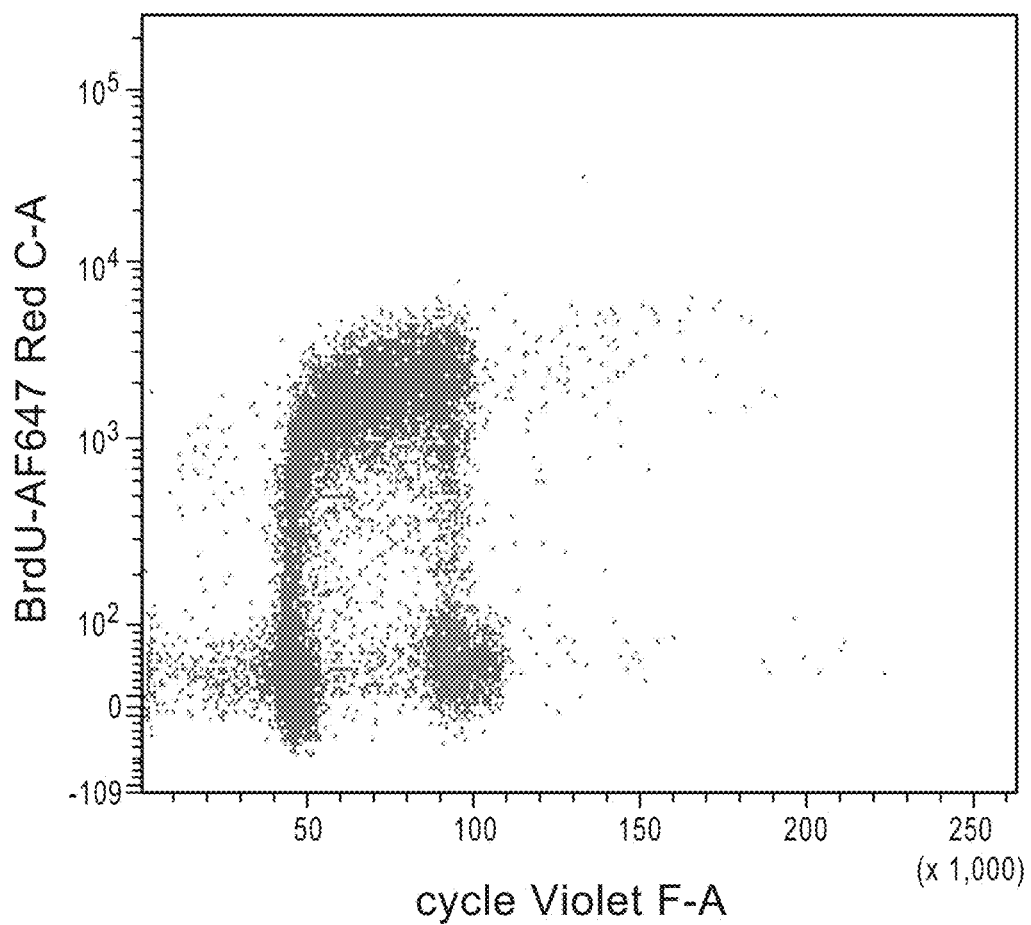
Figure 4D:
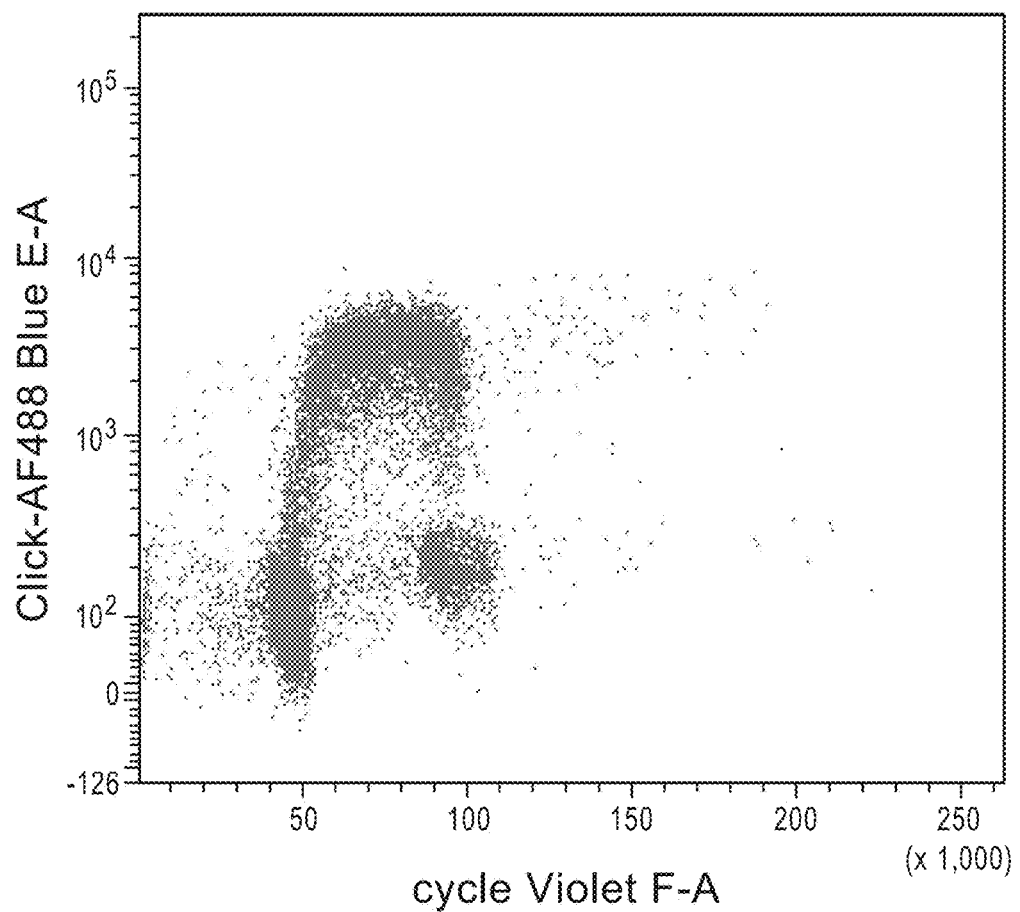
Figure 5A:
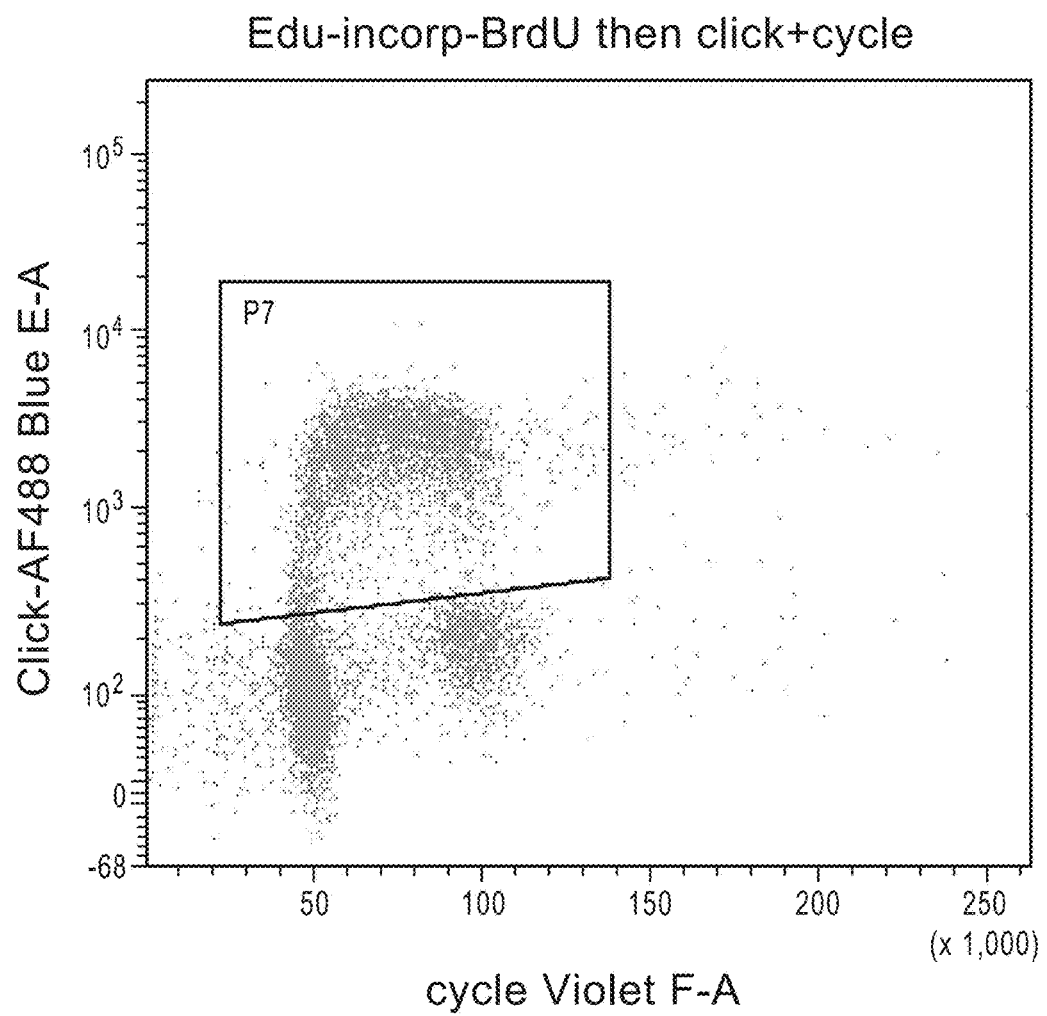
FIG. 5A, FIG. 5B, FIG. 5C and FIG. 5D present a series of graphs showing that when cells are treated with EdU and BrdU simultaneously, only a population of DNA labeled with BrdU is detected by flow cytometry. The first graph (FIG. 5A) shows a plot of EdU vs. DNA cell cycle only treated with a single pulse label of EdU. The second graph (FIG. 5B) shows a plot of BrdU vs. DNA cell cycle only treated with a single pulse label of BrdU. The third and fourth graphs (FIGS. 5C and 5D, respectively) show the dual parameter plot of fluorescent nucleotide label vs. DNA cell cycle treated with EdU and BrdU simultaneously. Only BrdU was incorporated into cells treated simultaneously with EdU and BrdU, as shown in the third and fourth graphs.
Figure 5B:
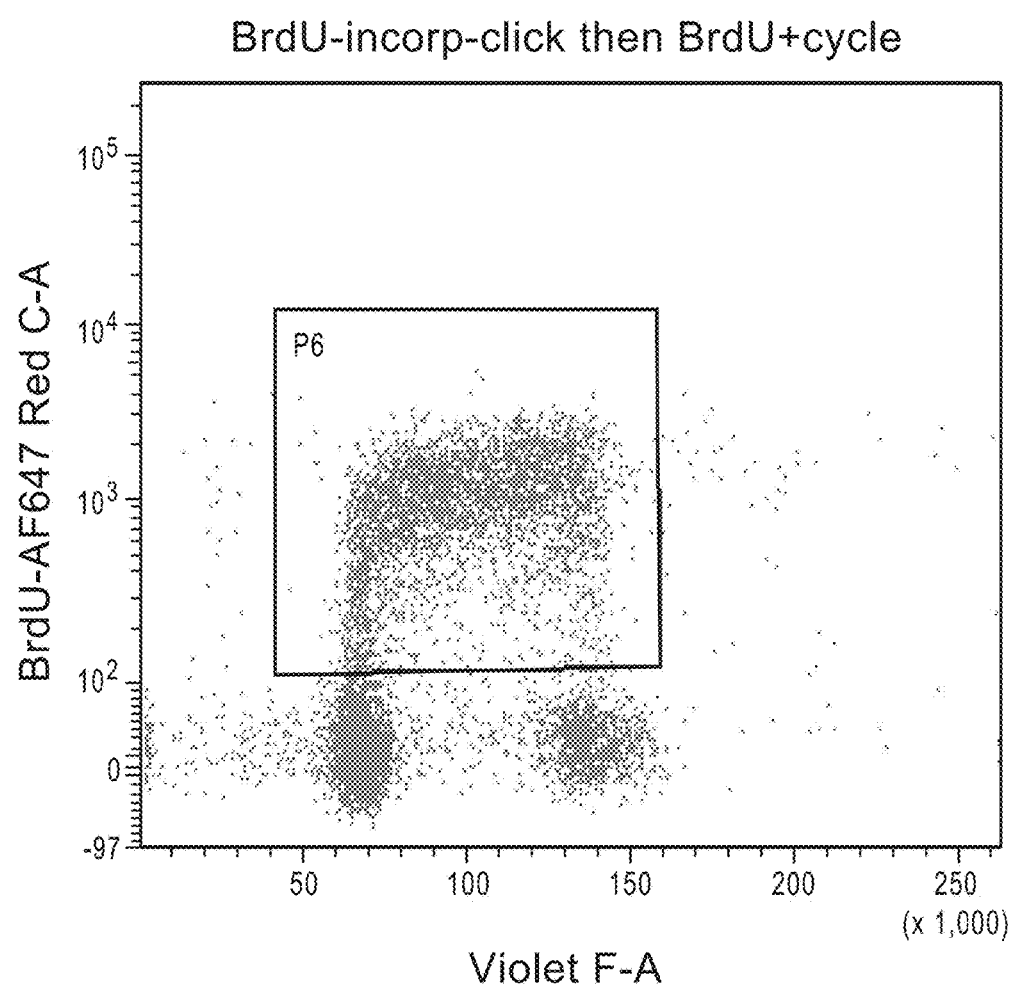
Figure 5C:
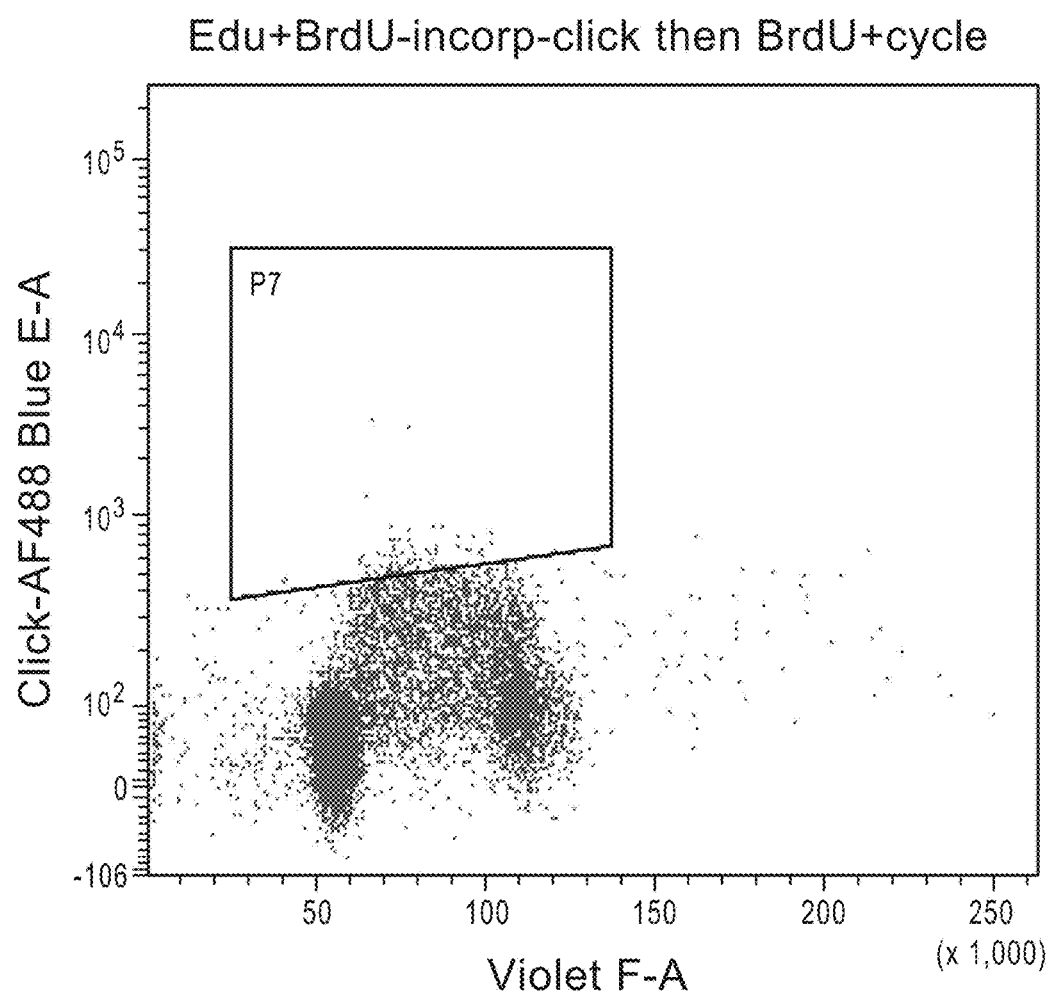
Figure 5D:
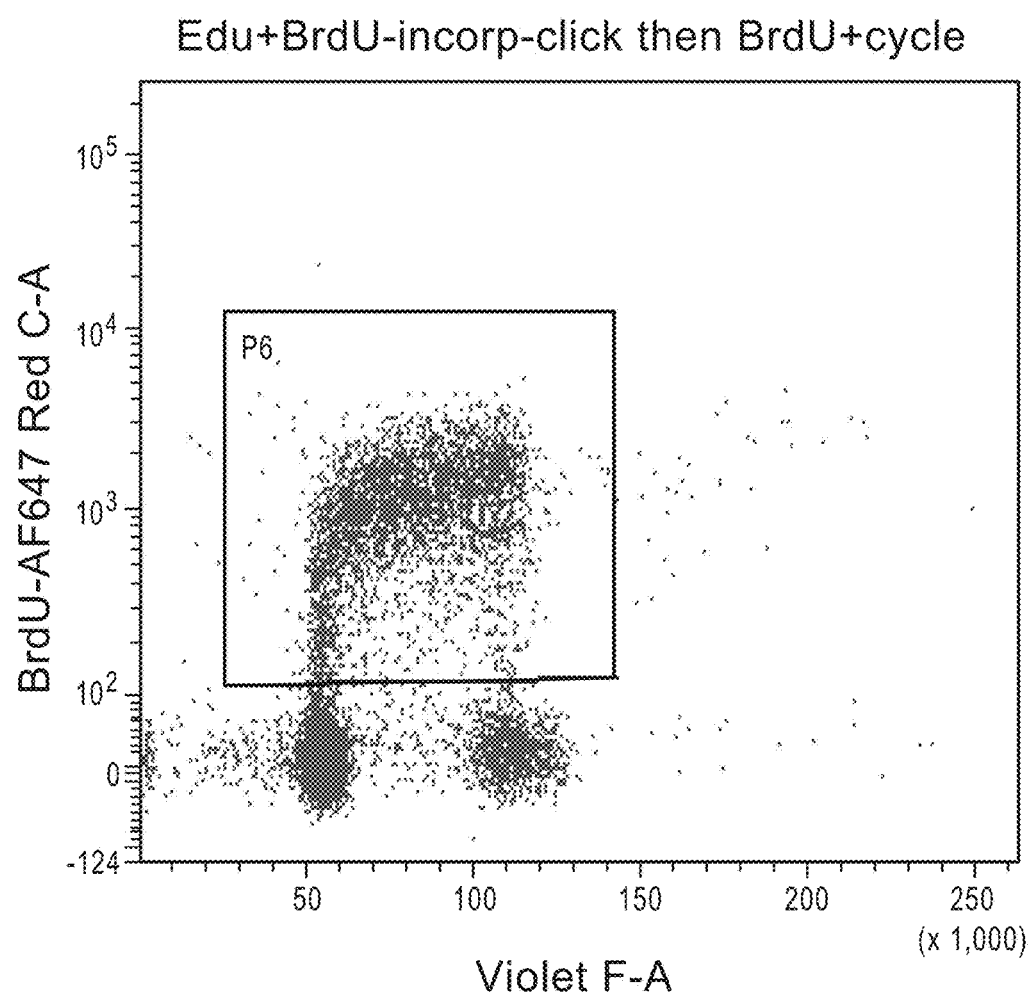
Figure 6A:
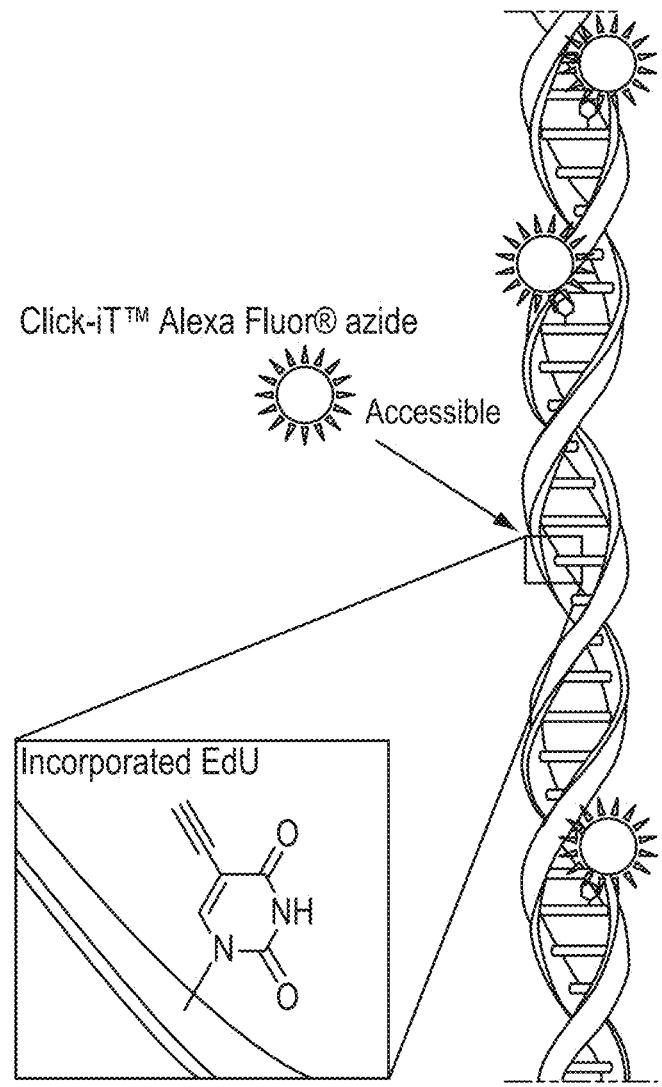
FIG. 6A and FIG. 6B present depictions of incorporation of nucleoside analogs into DNA.
Figure 6B:
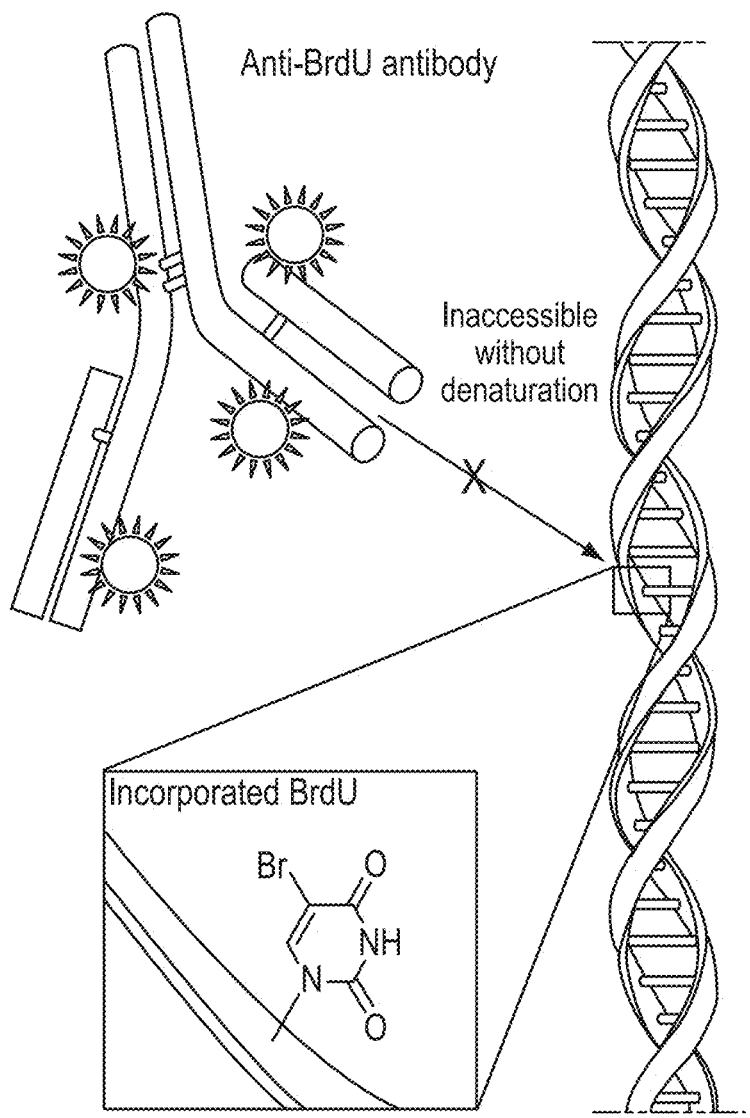

Since there was no treatment between the additions of the two pulses of nucleoside analog which might result in a change in the rate of newly synthesized DNA, the incorporation of the two analogs should be equivalent. In the graphs several cell subpopulations can be seen. There were cells which did not contain either label (FIG. 1 Q3 quadrant). These cells were not actively replicating their DNA during the testing period.

There were also cells which have both the EdU and the BrdU label incorporated into the DNA (FIG. 1 Q2 quadrant). These cells had continued DNA synthesis during the entire course of the test period of both pulses and the treatment.

There was also a population of cells which only had a label from the first pulse (EdU) (FIGS. 2A, 2B and 2C & FIGS. 4A, 4B, 4C and 4D). These cells were in late synthesis phase during the labeling by EdU. This can be seen in the mapping on the graph of total DNA vs. EdU label. By the time the pulse of BrdU was added, these cells had quit replicating their DNA.

There was also a population of cells which only had the label from the second pulse (FIGS. 3A-1, 3A-2, 3A-3 and 3B & FIGS. 4A, 4B, 4C and 4D). These cells were not actively replicating their DNA during the time of the first pulse but entered into the DNA synthesis phase during the time of the second pulse. Treatments that cause increases or decreases in the rate of synthesis can easily be seen and quantitated from the patterns of the graphs of the cell populations collected by flow cytometry.

Example 3

In a third experiment the addition of both EdU and BrdU nucleoside analogs simultaneously results in only a population of cells whose DNA was labeled with BrdU (FIGS. 5A, 5B, 5C and 5D). This third experiment is a demonstration of the no wash requirement of the first label, prior to the addition of the second label. The cells were then harvested, washed, fixed with 70% ice-cold ETOH and stored at 4° C. for 96 hours. The cells were then washed and resuspended in 4M HCL for 20 minutes at room temperature. A phosphate/citric acid buffer was added, and the cells washed twice and resuspended in 0.1% Triton® X-100/1% BSA/PBS at $1 \times 10^7$/ml. Then, labeling of the EdU was performed by adding click chemistry based reagents, including a solution comprised of $CuSO_4$ in Tris-buffered saline and Alexa Fluor® 488 conjugate (495 nm excitation maxima/519 nm emission maxima) (Molecular Probes®/Invitrogen™, Carlsbad, Calif.). The cells were then washed with 0.1% Triton® X-100/1% BSA/PBS. After this, labeling of the BrdU was performed using the anti-BrdU antibody Alexa Fluor® 647 conjugate (650 nm excitation maxima/670 nm emission maxima) (Molecular Probes™/Invitrogen™, Carlsbad, Calif.). To detect DNA content, a nucleic acid dye, SYTOX® Blue stain (444 nm excitation maxima/480 nm emission maxima) (Molecular Probes®/Invitrogen™, Carlsbad, Calif.) was added with RNase (Invitrogen™, Carlsbad, Calif.). Detection of the three labels was performed by flow cytometry. To detect the EdU label, 488 nm excitation was used, with a 530/30 nm bandpass. To detect the BrdU label, 633 nm excitation was used, with a 660/20 nm bandpass. To detect DNA content, 405 nm excitation was used, with a 450/50 nm bandpass. This result demonstrates that in the presence of both nucleoside analogs, only the BrdU analog is incorporated into the DNA, thus confirming the efficacy of the methods that do not require a wash step prior to adding the competitive nucleoside analog. The BrdU analog appears to be competitive with EdU when both are present during nucleic acid synthesis.

Example 4

A standard method of preparing cultured cells for the measurement of newly synthesized DNA (cellular proliferation) is set up according to known conditions for cells to be actively growing by providing the proper media and nutrient requirements. In the present example, Jurkat cell cultures were diluted one to four to a density of $2\times10^5$ cells/ml. After these cells have been growing for two or three days the first nucleoside analog, EdU, was added at 20 µM, a concentration appropriate for incorporation in the DNA of cells undergoing DNA synthesis. The cells were grown in the presence of EdU for one hour. After one hour of growth and without the removal of EdU through the washing of the cells in fresh media, an appropriate amount of the competitive nucleoside analog, BrdU, was added at a 10 µM concentration, and the cells were grown for one hour. The cells were then harvested, washed, fixed with 70% ice-cold ETOH and stored at 4° C. for 96 hours. The cells were then washed and resuspended in 4M HCL for 20 minutes at room temperature. A phosphate/critric acid buffer was added, and the cells washed twice and resuspended in 0.1% TritonX/1% BSA/PBS at $1\times10^7$/ml. Labeling of the BrdU was performed using the anti-BrdU antibody Alexa Fluor® 647 conjugate (650 nm excitation maxima/670 nm emission maxima) (Molecular Probes™/Invitrogen™, Carlsbad, Calif.). The cells were then washed with 0.1% TritonX/1% BSA/PBS. After this labeling of the EdU was performed by adding click chemistry based reagents, including a solution comprised of $CuSO_4$ in Tris-buffered saline and Alexa Fluor® 488-azide (495 nm excitation maxima/519 nm emission maxima) (Molecular Probes™/Invitrogen™, Carlsbad, Calif.). To detect DNA content, a nucleic acid dye, SYTOX® Blue stain (444 nm excitation maxima/480 nm emission maxima) (Molecular Probes™/Invitrogen™, Carlsbad, Calif.) was added with RNase (Invitrogen™, Carlsbad, Calif.). Detection of the three labels was performed by flow cytometry. To detect the EdU label, 488 nm excitation was used, with a 530/30 nm bandpass. To detect the BrdU label, 633 nm excitation was used, with a 660/20 nm bandpass. To detect DNA content, 405 nm excitation was used, with a 450/50 nm bandpass.

Example 5

A standard method of preparing cultured cells for the measurement of newly synthesized RNA (gene expression) is set up according to known conditions for cells to be actively growing by providing the proper media and nutrient requirements. In the present example, HeLa cell cultures are diluted one to four to a density of $2\times10^5$ cells onto coverslips within a 6 well plate. After these cells have been growing for two days the first nucleoside analog, EU, is added at a concentration appropriate for incorporation in the RNA of cells actively transcribing message. The cells are grown in the presence of EU for one hour. After one hour of growth and without the removal of EU through the washing of the cells in fresh media, an appropriate amount of the competitive nucleoside analog, BrU, is added at a 10 µM concentration, and the cells are grown for thirty minutes. The cells are then harvested, washed, fixed with 3.7% formaldehyde/PBS for 30 minutes at 4° C. The cells are then washed in 3% BSA/PBS, permeabilized in 1.0% Triton® X-100/PBS and denatured first with 1 M HCl at 4° C. for 10 minutes followed by-2 M HCl for 30 minutes room temperature. A borate buffer is then used to neutralize the cells. Labeling of the EU is performed by adding click chemistry based reagents, including a solution comprised of $CuSO_4$ in Tris-buffered saline and Alexa Fluor® 488 conjugate (495 nm excitation maxima/519 nm emission maxima) (Molecular Probes®/Invitrogen™, Carlsbad, Calif.). The cells are then washed and blocked with 1.0% Triton® X-100/3% BSA/PBS. After this, labeling of the BrU is performed using the anti-BrdU antibody and a secondary detection antibody Alexa Fluor® 647 conjugate (650 nm excitation maxima/670 nm emission maxima) (Molecular Probes®/Invitrogen™, Carlsbad, Calif. To detect the EdU label, 470/50 nm excitation is used, with a 545/75 nm bandpass. To detect the BrdU label, 630/50 nm excitation is used, with a 695/55 nm bandpass. Detection of the two labels is performed by fluorescence microscopy using standard techniques and appropriate filters.

Example 6

A standard method of preparing cultured cells for the measurement of newly synthesized RNA (gene expression) is set up according to known conditions for cells to be actively growing by providing the proper media and nutrient requirements. In the present example, HeLa cell cultures are diluted one to four to a density of $2\times10^5$ cells onto coverslips within a 6 well plate. After these cells have been growing for two days the first nucleoside analog, EU, is added at a concentration appropriate for incorporation in the RNA of cells actively transcribing message. The cells are grown in the presence of EU for one hour. After one hour of growth and without the removal of EU through the washing of the cells in fresh media, an appropriate amount of α-amanitin (100 µg/mL) along with the appropriate amount of the competitive nucleoside analog, BrU, is added at a 10 µM concentration, and the cells are grown for fifteen minutes. The cells are allowed to grow an additional time from 5 to 30 minutes. The cells are then harvested, washed, fixed with 3.7% formaldehyde/PBS for 30 minutes at 4° C. The cells are then washed in 3% BSA/PBS, permeabilized in 1.0% Triton® X-100/PBS and denatured first with 1 M HCl at 4° C. for 10 minutes followed by-2 M HCl for 30 minutes room temperature. A borate buffer is then used to neutralize the cells. Labeling of the EU is performed by adding click chemistry based reagents, including a solution comprised of $CuSO_4$ in Tris-buffered saline and Alexa Fluor® 488 conjugate (495 nm excitation maxima/519 nm emission maxima) (Molecular Probes®/Invitrogen™, Carlsbad, Calif.). The cells are then washed and blocked with 1.0% Triton® X-100/3% BSA/PBS. After this, labeling of the BrU is performed using the anti-BrdU antibody and a secondary detection antibody Alexa Fluor® 647 conjugate (650 nm excitation maxima/670 nm emission maxima) (Molecular Probes®/Invitrogen™, Carlsbad, Calif.). Detection of the two labels is performed by fluorescence microscopy using standard techniques and appropriate filters. To detect the EdU label, 470/50 nm excitation is used, with a 545/75 nm bandpass. To detect the BrdU label, 630/50 nm excitation is used, with a 695/55 nm bandpass.

Example 7

A standard method of preparing cultured cells for the measurement of newly synthesized RNA (gene expression) is set up according to known conditions for cells to be actively growing by providing the proper media and nutrient requirements. In the present example, HeLa cell cultures are diluted one to four to a density of $2\times10^5$ cells/ml. After these cells have been growing for two or three days to achieve 70% confluency they are lipofected with the first nucleoside analog, EUTP to deliver the compound to the nucleus at a concentration appropriate for incorporation in the RNA of cells actively transcribing message. The cells were grown in the presence of EUTP for 15 minutes. After 15 minutes of growth and without the removal of EUTP, the cells are lipofected with the competitive nucleoside analog, BrUTP, added at appropriate concentration and the cells are grown an additional fifteen minutes. The cells are then allowed to grow for various times before harvesting. The cells are then harvested, washed, fixed with 3.7% formaldehyde/PBS for 30 minutes at 4° C. The cells are then washed in 3% BSA/PBS, permeabilized in 1.0% Triton® X-100/PBS and denatured first with 1 M HCl at 4° C. for 10 minutes followed by-2 M HCl for 30 minutes room temperature. A borate buffer is then used to neutralize the cells. Labeling of the EU is performed by adding click chemistry based reagents, including a solution comprised of $CuSO_4$ in Tris-buffered saline and Alexa Fluor® 488 conjugate (495 nm excitation maxima/519 nm emission maxima) (Molecular Probes®/Invitrogen™, Carlsbad, Calif.). The cells are then washed and blocked with 1.0% Triton® X-100/3% BSA/PBS. After this, labeling of the BrU is performed using the anti-BrdU antibody and a secondary detection antibody Alexa Fluor® 647 conjugate (650 nm excitation maxima/670 nm emission maxima) (Molecular Probes®/Invitrogen™, Carlsbad, Calif.). Detection of the two labels is performed by fluorescence microscopy using standard techniques and appropriate filters. To detect the EdU label, 470/50 nm excitation is used, with a 545/75 nm bandpass. To detect the BrdU label, 630/50 nm excitation is used, with a 695/55 nm bandpass.

Example 8

A standard method of preparing cultured cells for the measurement of newly synthesized DNA is set up according to known conditions for cells to be actively growing by providing the proper media and nutrient requirements. In the present example, HeLa cell cultures are diluted one to four to a density of $2 \times 10^5$ cells onto coverslips within a 6 well plate. After these cells have been growing for two days the first nucleoside analog, EdU, is added at 10 µM, a concentration appropriate for incorporation in the DNA of cells undergoing DNA synthesis. The cells are grown in the presence of EdU for one hour. After one hour of growth and without the removal of EdU through the washing of the cells in fresh media, an appropriate amount of a second nucleoside analog for the labeling of newly synthesized DNA, AzdU is added at 10 mM along with a drug which alters cell proliferation rate and are grown for an additional 30 minutes. After the second incubation, a third competitive analog, BrdU, is added at a 10 µM concentration along with a second treatment which alters cell proliferation rate, and the cells are grown for an additional thirty minutes. The cells are then harvested, washed, fixed with 3.7% formaldehyde/PBS for 30 minutes at 4° C. The cells are then washed in 3% BSA/PBS, permeabilized in 1.0% Triton® X-100/PBS and denatured first with 1 M HCl at 4° C. for 10 minutes followed by-2 M HCl for 20 minutes room temperature. A borate buffer is then used to neutralize the cells. Then, labeling of the AzU is performed by washing the cells two times with 3% BSA in PBS, and adding the copper-less click chemistry based reagents, including a solution comprised of Alexa Fluor® 488-constrained cycloalkyne (495 nm excitation maxima/519 nm emission maxima) (Molecular Probes™/Invitrogen™, Carlsbad, Calif.) in Tris-buffered saline. After this reaction, labeling of the EdU is performed by adding click chemistry based reagents, including a solution comprised of $CuSO_4$ in Tris-buffered saline and Alexa Fluor® 594 conjugate (590 nm excitation maxima/615 nm emission maxima) (Molecular Probes®/Invitrogen™, Carlsbad, Calif.). The cells are then washed and blocked with 1.0% Triton® X-100/3% BSA/PBS. After this, labeling of the BrdU is performed using the anti-BrdU antibody and a secondary detection antibody Alexa Fluor® 647 conjugate (650 nm excitation maxima/670 nm emission maxima) (Molecular Probes®/Invitrogen™, Carlsbad, Calif.) Detection of the three labels is performed by fluorescence microscopy using standard techniques. To detect the AzdU label, 470/50 nm excitation is used, with a 545/75 nm bandpass. To detect the EdU label, 560/55 nm excitation is used, with a 645/75 nm bandpass. To detect the BrdU label, 630/50 nm excitation is used, with a 695/55 nm bandpass.

Example 9

A standard method of preparing cultured cells for the measurement of newly synthesized DNA (cellular proliferation) is set up according to known conditions for cells to be actively growing by providing the proper media and nutrient requirements. In the present example, Ramos human B-lymphocyte cell cultures were diluted one to four to a density of $2 \times 10^5$ cells/ml. After these cells had been growing for one or two days, the first nucleoside analog, EdU, was added at 20 µM, a concentration appropriate for incorporation in the DNA of cells undergoing DNA synthesis. The cells were grown in the presence of EdU for two hours. After 2 hours of growth and without the removal of EdU through the washing of the cells in fresh media, an appropriate amount of the competitive nucleoside analog, BrdU, was added at a 10 µM concentration, and the cells were grown for 2.5 hours. The cells were then harvested, washed, fixed with 70% ice-cold ETOH and stored at 4° C. for 96 hours. The cells were then washed and resuspended in 4M HCL for 20 minutes at room temperature. A phosphate/critric acid buffer was added, and the cells washed twice and resuspended in 0.1% TritonX/1% BSA/PBS at $1 \times 10^7$/ml. Then, labeling of the EdU was performed by adding click chemistry based reagents, including a solution comprised of $CuSO_4$ in Tris-buffered saline and Alexa Fluor® 647-azide (650 nm excitation maxima/670 nm emission maxima) (Molecular Probes™/Invitrogen™, Carlsbad, Calif.). The cells were then washed with 0.1% TritonX/1% BSA/PBS. After this, labeling of the BrdU was performed using the anti-BrdU antibody FITC conjugate (494 nm excitation maxima/518 nm emission maxima) (Exalpha Biologicals, Inc., Maynard Calif.). To detect DNA content, a nucleic acid dye, DAPI (358 nm excitation maxima/461 nm emission maxima) (Molecular Probes™/Invitrogen™, Carlsbad, Calif.) was added. Detection of the three labels was performed by flow cytometry. To detect the BrdU label, 488 nm excitation was used, with a 530/30 nm bandpass. To detect the EdU label, 633 nm excitation was used, with a 660/20 nm bandpass. To detect DNA content, 355 nm excitation was used, with a 450/50 nm bandpass.

Figure 7A:
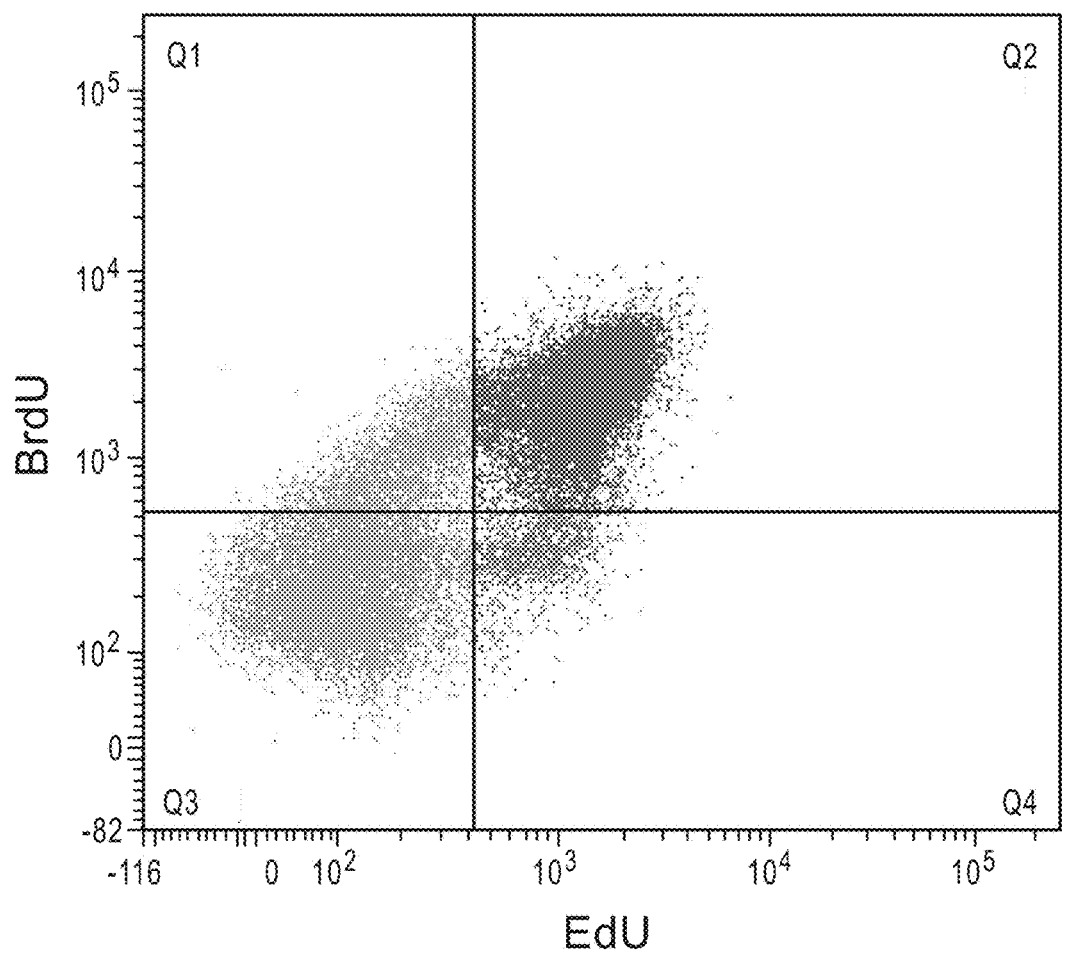
FIG. 7A, FIG. 7B and FIG. 7C show populations of cells (Ramos B-lymphocytes)
Figure 7B:
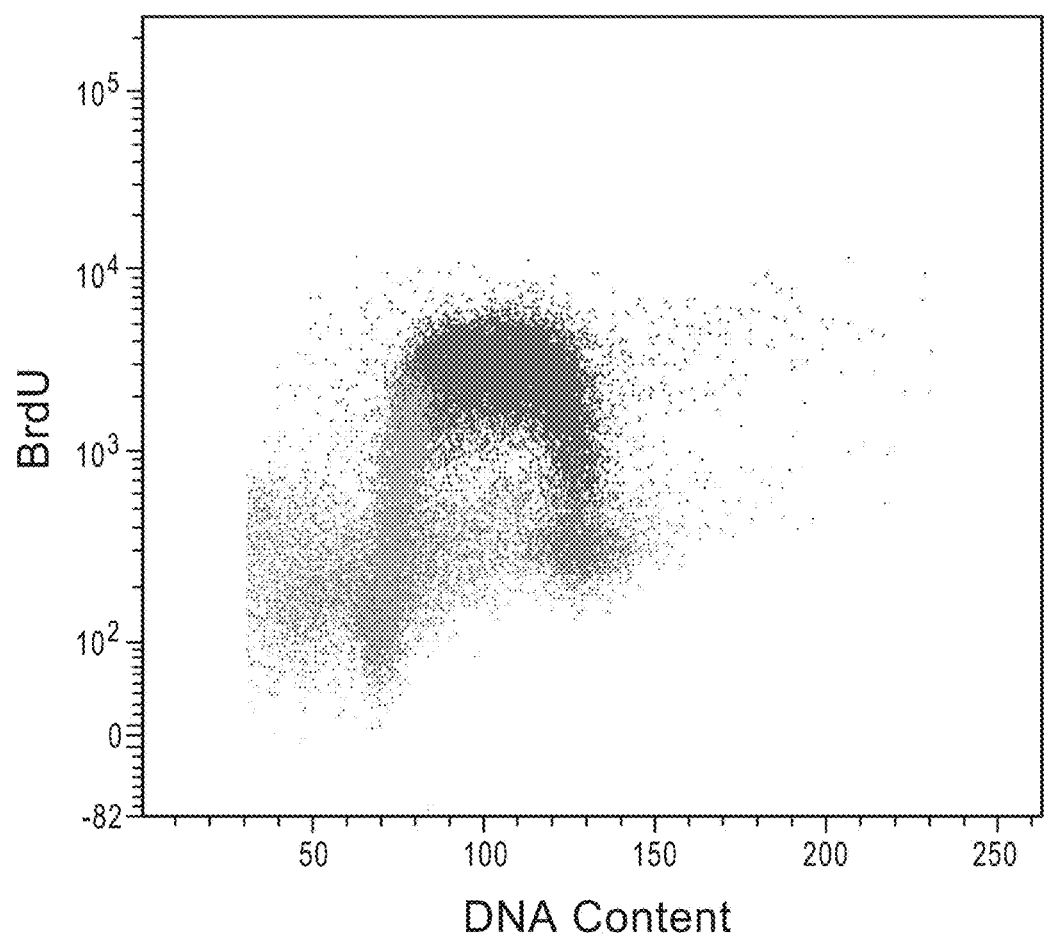
Figure 7C:
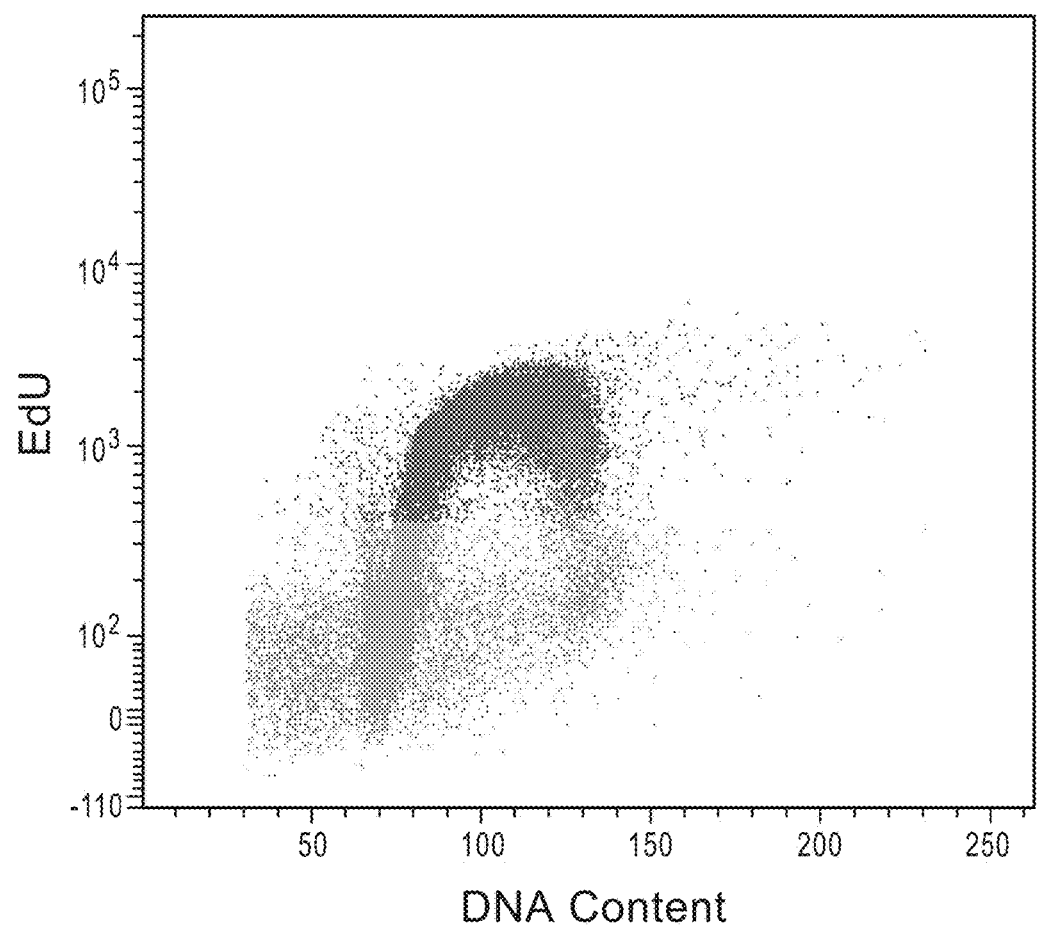

A series of result graphs labeled FIG. 7A, FIG. 7B and FIG. 7C show populations of the cells treated with a first pulse label of EdU (20 µM) and a second pulse label of BrdU (10 µm) as detected by flow cytometry. FIG. 7A is divided into four quadrants with the first quadrant (Q1) located in the upper left hand corner, the second quadrant (Q2) located in the upper right hand corner, the third quadrant (Q3) located in the lower left hand corner, and the fourth quadrant (Q4) located in the lower right hand corner. Populations of cells in quadrant Q3 (lower left, colored light blue) are negative for both EdU (first pulse) and BrdU (second pulse). Populations of cells in quadrant Q2 (upper right, colored dark blue) are positive for both EdU (first pulse) and BrdU (second pulse). Populations of cells in quadrant Q1 (upper left, colored light green) are positive for BrdU and negative for EdU, a sub-population of BrdU-positive cells which are EdU-negative, this sub-population being the population of cells entering S-phase after the EdU only incorporation. Populations of cells in Q4 (lower right, colored red) are positive for EdU and negative for BrdU, a sub-population of EdU-positive cells (late-stage S) which are BrdU-negative, this sub-population being the population of cells leaving S-phase before the BrdU-incorp. FIG. 7B is a graph of BrdU vs. DNA content showing these same colored populations from FIG. 7A. FIG. 7C is a graph of EdU vs DNA content showing these same colored populations from FIG. 7A.

Example 10

A standard method of preparing cultured cells for the measurement of newly synthesized DNA (cellular proliferation) is set up according to known conditions for cells to be actively growing by providing the proper media and nutrient requirements. In the present example, K562 human lymphoblast from chronic myelogenous leukemia cell cultures were diluted one to four to a density of $2 \times 10^5$ cells/ml. After these cells had been growing for one or two days, the first nucleoside analog, EdU, was added at 20 µM, a concentration appropriate for incorporation in the DNA of cells undergoing DNA synthesis. The cells were grown in the presence of EdU for two hours. After 2 hours of growth and without the removal of EdU through the washing of the cells in fresh media, an appropriate amount of the competitive nucleoside analog, BrdU, was added at a 10 µM concentration, and the cells were grown for 2.5 hours. The cells were then harvested, washed, fixed with 70% ice-cold ETOH and stored at 4° C. for 96 hours. The cells were then washed and resuspended in 4M HCL for 20 minutes at room temperature. A phosphate/critric acid buffer was added, and the cells washed twice and resuspended in 0.1% TritonX/1% BSA/PBS at $1 \times 10^7$/ml. Then, labeling of the EdU was performed by adding click chemistry based reagents, including a solution comprised of $CuSO_4$ in Tris-buffered saline and Alexa Fluor® 647-azide (650 nm excitation maxima/670 nm emission maxima) (Molecular Probes™/Invitrogen™, Carlsbad, Calif.). The cells were then washed with 0.1% TritonX/1% BSA/PBS. After this, labeling of the BrdU was performed using the anti-BrdU antibody FITC conjugate (494 nm excitation maxima/518 nm emission maxima) (Exalpha Biologicals, Inc., Maynard Calif.). To detect DNA content, a nucleic acid dye, DAPI (358 nm excitation maxima/461 nm emission maxima) (Molecular Probes™/Invitrogen™, Carlsbad, Calif.) was added. Detection of the three labels was performed by flow cytometry. To detect the BrdU label, 488 nm excitation was used, with a 530/30 nm bandpass. To detect the EdU label, 633 nm excitation was used, with a 660/20 nm bandpass. To detect DNA content, 355 nm excitation was used, with a 450/50 nm bandpass.

A series of result graphs labeled FIG. 8A, FIG. 8B and FIG. 8C show populations of the cells treated with a first pulse label of EdU (20 µM) and a second pulse label of BrdU (10 µm) as detected by flow cytometry. FIG. 8A is divided into four quadrants with the first quadrant (Q1) located in the upper left hand corner, the second quadrant (Q2) located in the upper right hand corner, the third quadrant (Q3) located in the lower left hand corner, and the fourth quadrant (Q4) located in the lower right hand corner. Populations of cells in quadrant Q3 (lower left, colored light blue) are negative for both EdU (first pulse) and BrdU (second pulse). Populations of cells in quadrant Q2 (upper right, colored dark blue) are positive for both EdU (first pulse) and BrdU (second pulse). Populations of cells in quadrant Q1 (upper left, colored light green) are positive for BrdU and negative for EdU, a sub-population of BrdU-positive cells which are EdU-negative, this sub-population being the population of cells entering S-phase after the Edu only incorporation. Populations of cells in Q4 (lower right, colored red) are positive for EdU and negative for BrdU, a sub-population of EdU-positive cells (late-stage S) which are BrdU-negative, this sub-population being the population of cells leaving S-phase before the BrdU-incorp. FIG. 8B is a graph of BrdU vs. DNA content showing these same colored populations from FIG. 8A. FIG. 8C is a graph of EdU vs DNA content showing these same colored populations from FIG. 8A.

Example 11

A standard method of preparing cultured cells for the measurement of newly synthesized DNA (cellular proliferation) is set up according to known conditions for cells to be actively growing by providing the proper media and nutrient requirements. In the present example, TF-1a human erythroblast cell cultures were diluted one to four to a density of $2 \times 10^5$ cells/ml. Culture media contains GM-CSF, or granulocyte-macrophage colony-stimulating factor, for growth. After these cells had been growing for one or two days, the first nucleoside analog, EdU, was added at 20 ☐M, a concentration appropriate for incorporation in the DNA of cells undergoing DNA synthesis. The cells were grown in the presence of EdU for time listed in chart 1. After initial period of growth and without the removal of EdU through the washing of the cells in fresh media, an appropriate amount of the competitive nucleoside analog, BrdU, was added at a 10 ☐M concentration, and the cells were grown for time listed in chart 1. The cells were then harvested, washed, fixed with 70% ice-cold ETOH and stored at 4° C. until use. The cells were then washed and resuspended in 4M HCL for 20 minutes at room temperature. A phosphate/critric acid buffer was added, and the cells washed twice and resuspended in 0.1% TritonX/1% BSA/PBS at $1 \times 10^7$/ml. Then, labeling of the EdU was performed by adding click chemistry based reagents, including a solution comprised of $CuSO_4$ in Tris-buffered saline and Alexa Fluor® 647-azide (650 nm excitation maxima/670 nm emission maxima) (Molecular Probes™/Invitrogen™, Carlsbad, Calif.). The cells were then washed with 0.1% TritonX/1% BSA/PBS. After this, labeling of the BrdU was performed using the anti-BrdU antibody FITC conjugate (494 nm excitation maxima/518 nm emission maxima) (Exalpha Biologicals, Inc., Maynard Calif.). To detect DNA content, a nucleic acid dye, DAPI (358 nm excitation maxima/461 nm emission maxima) (Molecular Probes™/Invitrogen™, Carlsbad, Calif.) was added. Detection of the three labels was performed by flow cytometry. To detect the BrdU label, 488 nm excitation was used, with a 530/30 nm bandpass. To detect the EdU label, 633 nm excitation was used, with a 660/20 nm bandpass. To detect DNA content, 355 nm excitation was used, with a 450/50 nm bandpass.

CHART 1

|   | first pulse-20 uM EdU | second pulse-10 uM BrdU |
| --- | --- | --- |
| A | 2 hours | 2 hours |
| B | 2 hours | 4 hours |

CHART 1-continued

|   | first pulse-20 uM EdU | second pulse-10 uM BrdU |
|---|---|---|
| C | 2 hours | 8 hours |
| D | 2 hours | 16 hours |
| E | 4 hours | 2 hours |
| F | 8 hours | 2 hours |
| G | 16 hours | 2 hours |
| H | 2 hours | none |
| I | none | 2 hours |

A series of result graphs labeled as FIGS. 9-1A, 9-1B, 9-1C, 9-2D, 9-2E, 9-2F, 9-3G, 9-3H and 9-3I show populations of cells (TF-1a human erythroblast cells). FIGS. 9-1A, 9-1B, 9-1C, 9-2D, 9-2E, 9-2F and 9-3G show the population of the cells treated with a first pulse label of EdU (20 μM) and a second pulse label of BrdU (10 μm) with the time of the pulses varied, as detected by flow cytometry. FIGS. 9-3H and 9-3I show the population of the cells treated with one pulse only, with FIG. 9-3H showing the result of a pulse label of EdU (20 μM) only and FIG. 9-3I showing result of a pulse label of BrdU (10 μm) only, as detected by flow cytometry.

The dual parameter graph is divided into four quadrants with the first quadrant (Q1) located in the upper left hand corner, the second quadrant (Q2) located in the upper right hand corner, the third quadrant (Q3) located in the lower left hand corner, and the fourth quadrant (Q4) located in the lower right hand corner. Populations of cells in quadrant Q3 are negative for both EdU (first pulse) and BrdU (second pulse). Populations of cells in quadrant Q2 are positive for both EdU (first pulse) and BrdU (second pulse). Populations of cells in quadrant Q1 are positive for BrdU and negative for EdU, a sub-population of BrdU-positive cells which are EdU-negative, this sub-population being the population of cells entering S-phase after the Edu only incorporation. Populations of cells in Q4 are positive for EdU and negative for BrdU, a sub-population of EdU-positive cells (late-stage S) which are BrdU-negative, this sub-population being the population of cells leaving S-phase before the BrdU-incorporation.

Example 12

A standard method of preparing cultured cells for the measurement of newly synthesized DNA (cellular proliferation) is set up according to known conditions for cells to be actively growing by providing the proper media and nutrient requirements. In the present example, TF-1a human erythroblast cell cultures were diluted one to four to a density of $2 \times 10^5$ cells/ml. Culture media contains varying amounts of GM-CSF, or granulocyte-macrophage colony-stimulating factor, at amounts equal to full (2 ng/ml) or ¼ (0.5 ng/ml) recommended concentration of GM-CSF, and no GM-CSF. After these cells had been growing 18 hours, the first nucleoside analog, EdU, was added at 20 μM, a concentration appropriate for incorporation in the DNA of cells undergoing DNA synthesis. The cells were grown in the presence of EdU for three hours. After initial period of growth and without the removal of EdU through the washing of the cells in fresh media, an appropriate amount of the competitive nucleoside analog, BrdU, was added at a 10 μM concentration, and GM-CSF was added at the same time as the BrdU in amounts to equal the full amount recommended for GM-CSF concentration of 2 ng/ml or kept at the same initial concentration of GM-CSF. The cells were grown for six hours. The cells were then harvested, washed, fixed with 70% ice-cold ETOH and stored at 4° C. until use. The cells were then washed and resuspended in 4M HCL for 20 minutes at room temperature. A phosphate/critric acid buffer was added, and the cells washed twice and resuspended in 0.1% TritonX/1% BSA/PBS at $1 \times 10^7$/ml. Then, labeling of the EdU was performed by adding click chemistry based reagents, including a solution comprised of $CuSO_4$ in Tris-buffered saline and Alexa Fluor® 647-azide (650 nm excitation maxima/670 nm emission maxima) (Molecular Probes™/Invitrogen™, Carlsbad, Calif.). The cells were then washed with 0.1% TritonX/1% BSA/PBS. After this, labeling of the BrdU was performed using the anti-BrdU antibody FITC conjugate (494 nm excitation maxima/518 nm emission maxima) (Exalpha Biologicals, Inc., Maynard Calif.). To detect DNA content, a nucleic acid dye, DAPI (358 nm excitation maxima/461 nm emission maxima) (Molecular Probes™/Invitrogen™, Carlsbad, Calif.) was added. Detection of the three labels was performed by flow cytometry. To detect the BrdU label, 488 nm excitation was used, with a 530/30 nm bandpass. To detect the EdU label, 633 nm excitation was used, with a 660/20 nm bandpass. To detect DNA content, 355 nm excitation was used, with a 450/50 nm bandpass.

Chart 2 shows the percentage of cells that are EdU positive and BrdU positive during the various CM-CSF treatments. The dual pulse with the full amount of 2 ng/ml GM-CSF is the control and shows the percentage of EdU and BrdU positive cell that are expected. The dual pulse with no GM-CSF shows decreased proliferation with both analogs, and addition of GM-CSF with just the BrdU pulse shows some proliferative recovery of cells with an increase of BrdU positivity. The dual pulse with 0.5 ng/ml GM-CSF shows only a slight decrease of proliferation over control, and does not show any proliferative recovery with addition of GM-CSF to 2 ng/ml with the BrdU pulse. This demonstrates the usefulness of using a dual pulse system to look at changes of proliferation, with addition of a growth factor in-between the pulses.

CHART 2

| GM-CSFconcentration with EdU pulse | GM-CSFconcentration with BrdU pulse | % EdU Pos | % BrdU Pos |
|---|---|---|---|
| 2 ng/ml (control) | 2 ng/ml (control) | 53.9 | 72.2 |
| none | none | 38.1 | 44.5 |
| none | 2 ng/ml | 42.3 | 53 |
| 0.5 ng/ml | 0.5 ng/ml | 57 | 66.3 |
| 0.5 ng/ml | 2 ng/ml | 57.5 | 65.1 |

Example 13

A standard method of preparing cultured cells for the measurement of newly synthesized DNA (cellular proliferation) is set up according to known conditions for cells to be actively growing by providing the proper media and nutrient requirements. In the present example, THP-1 monocyte cell cultures were diluted one to four to a density of $2 \times 10^5$ cells/ml. After these cells had been growing for 1-2 days, the first nucleoside analog, EdU, was added at 20 μM, a concentration appropriate for incorporation in the DNA of cells undergoing DNA synthesis. The cells were grown in the presence of EdU for one hour. After initial period of growth and without the removal of EdU through the washing of the cells in fresh media, an appropriate amount of the competitive nucleoside analog, BrdU, was added at a 10 μM concentration, and the cells were grown for one hour. The cells were then harvested, washed, fixed with 70% ice-cold ETOH and stored at 4° C. until use. The cells were then washed and resuspended in 4M HCL for 20 minutes at room temperature. A phosphate/critric acid buffer was added, and the cells washed twice and resuspended in 0.1% TritonX/1% BSA/PBS at 1×10$^7$/ml. Then, labeling of the EdU was performed by adding click chemistry based reagents, including a solution comprised of $CuSO_4$ in Tris-buffered saline and Alexa Fluor® 647-azide (650 nm excitation maxima/670 nm emission maxima) (Molecular Probes®/Invitrogen™, Carlsbad, Calif.). The cells were then washed with 0.1% TritonX/1% BSA/PBS. After this, labeling of the BrdU was performed using the anti-BrdU antibody FITC conjugate (494 nm excitation maxima/518 nm emission maxima) (Exalpha Biologicals, Inc., Maynard Calif.). To detect DNA content, a nucleic acid dye, DAPI (358 nm excitation maxima/461 nm emission maxima) (Molecular Probes™/Invitrogen™, Carlsbad, Calif.) was added. Detection of the three labels was performed by flow cytometry. To detect the BrdU label, 488 nm excitation was used, with a 530/30 nm bandpass. To detect the EdU label, 633 nm excitation was used, with a 660/20 nm bandpass. To detect DNA content, 355 nm excitation was used, with a 450/50 nm bandpass.

Figure 10A:
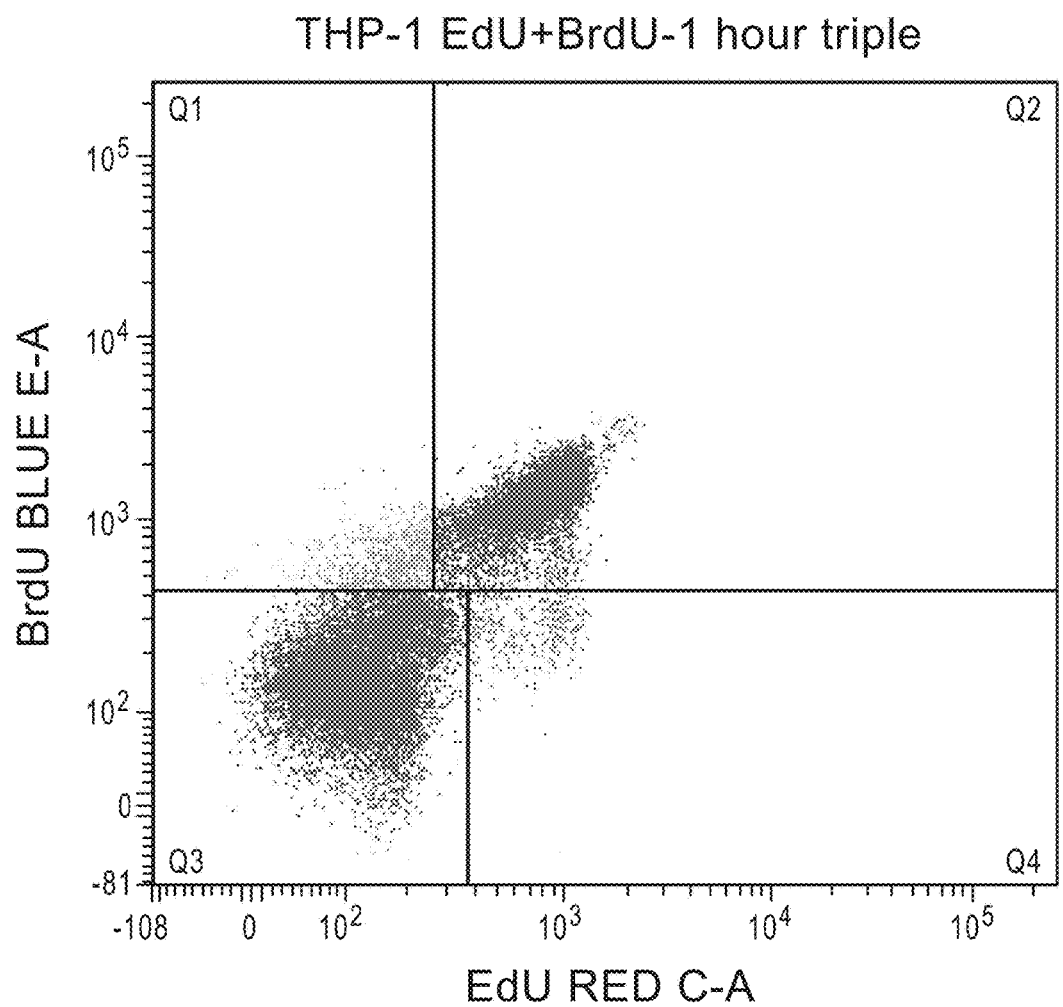
Figure 10B:
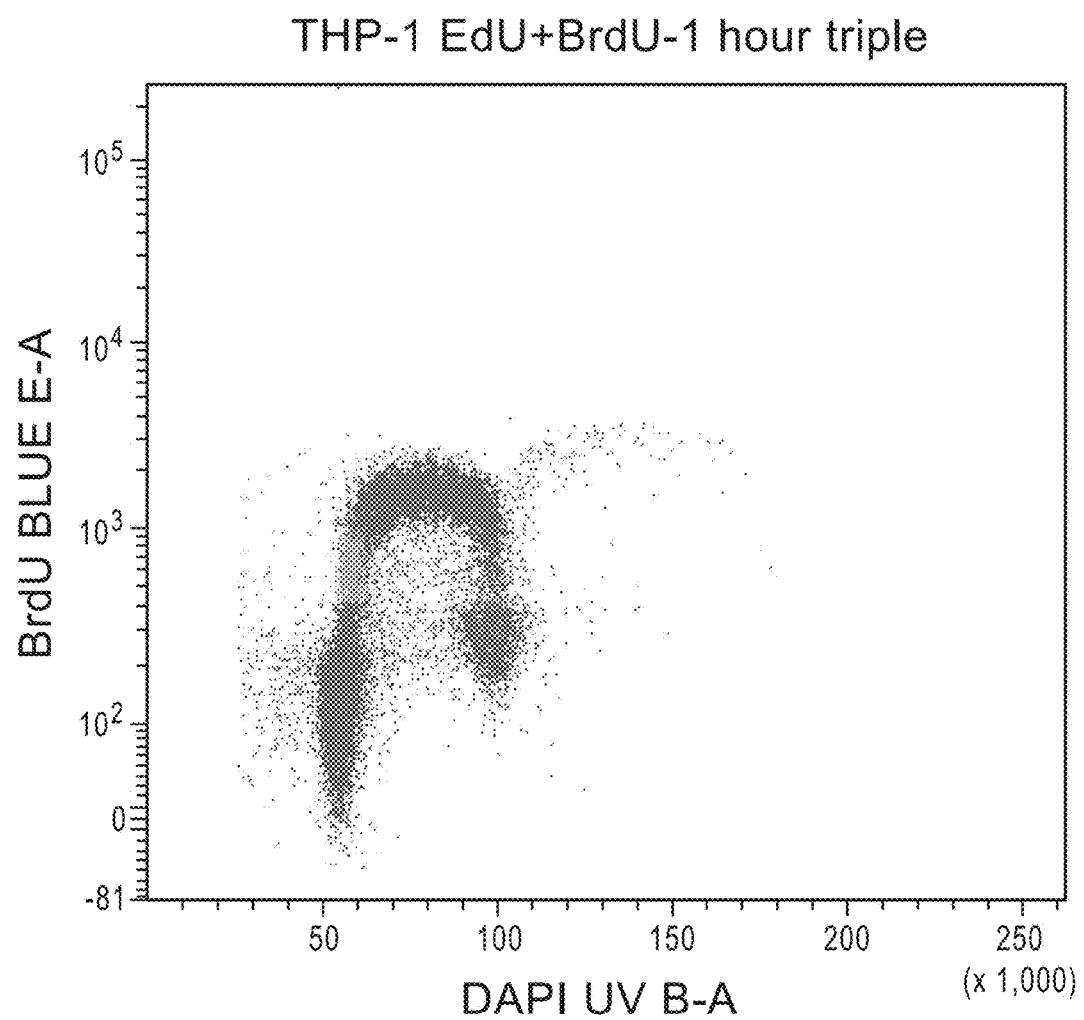
Figure 10C:
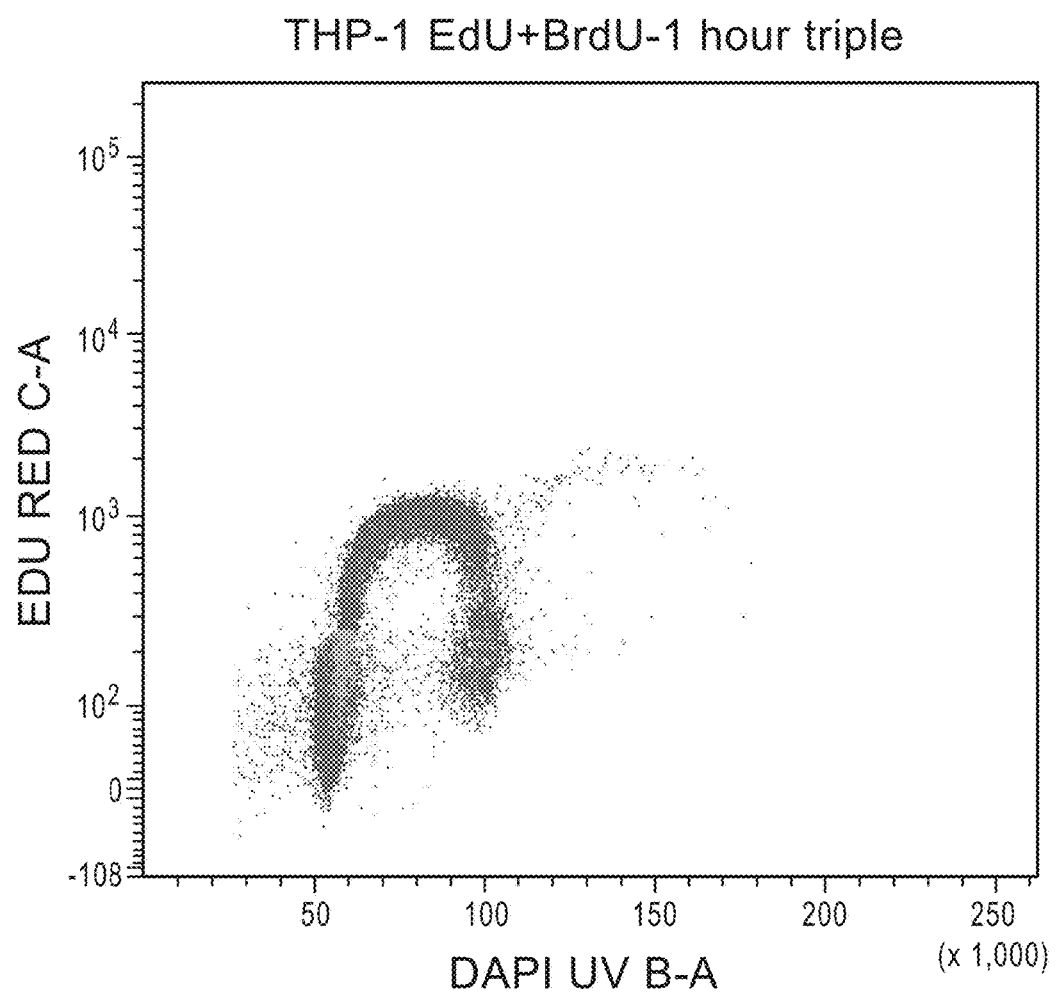
Figure 10D:
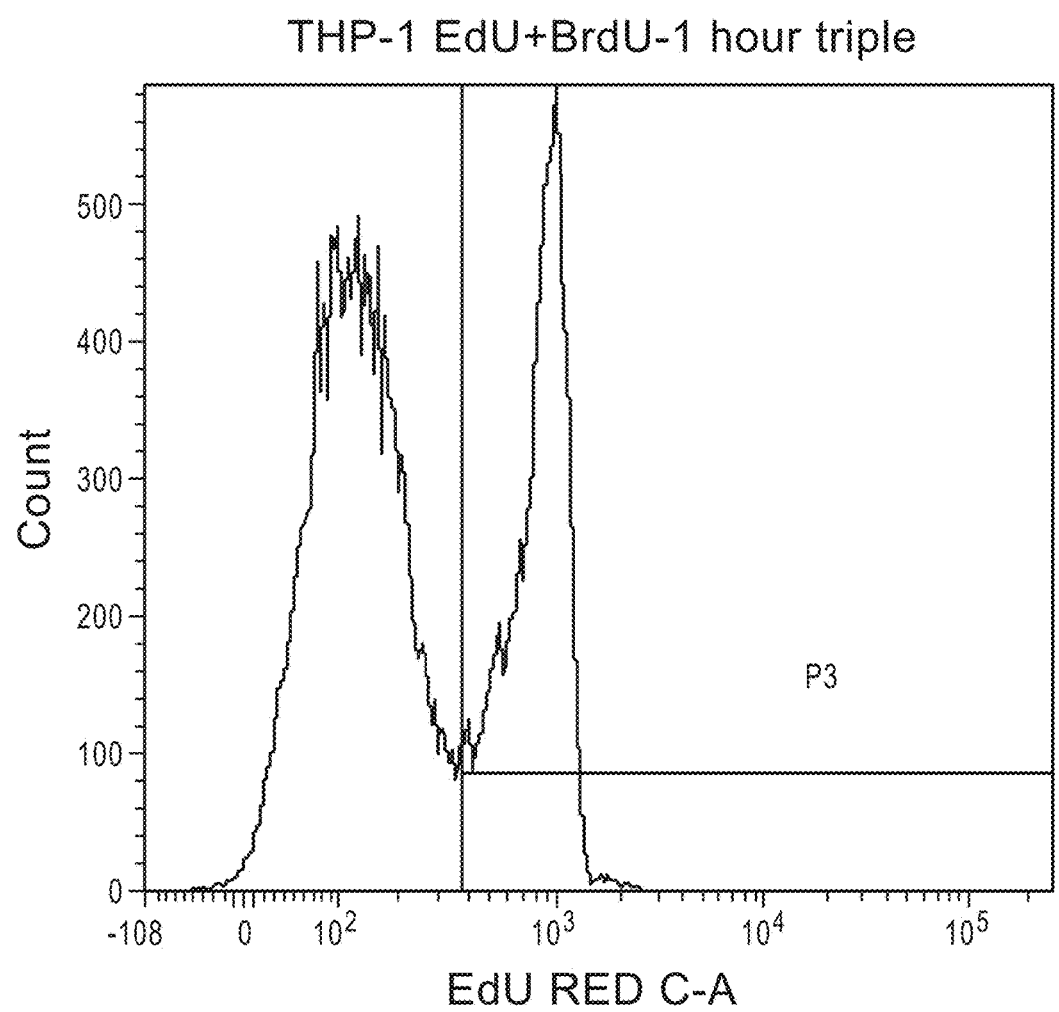
Figure 10E:
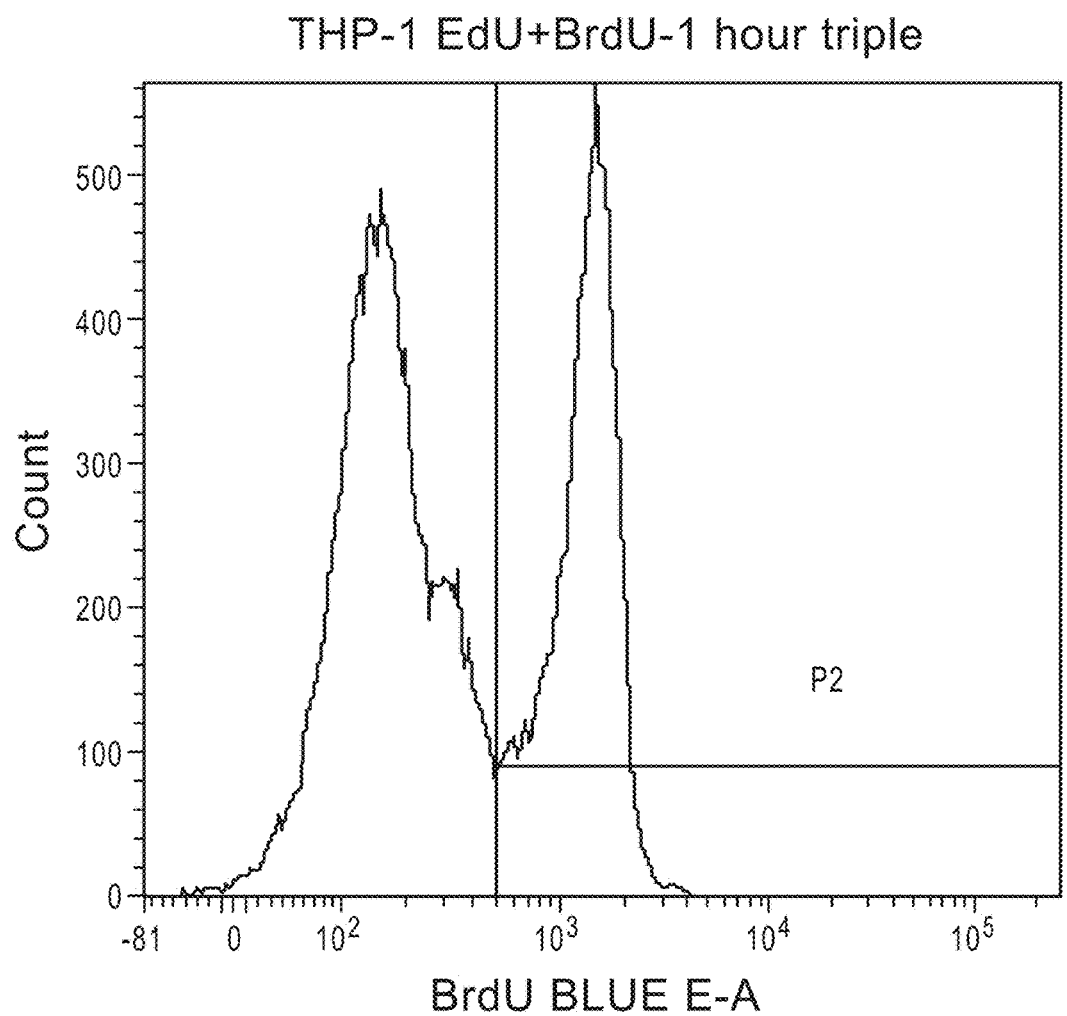

A series of result graphs labeled FIG. 10A, FIG. 10B, FIG. 10C, FIG. 10D and FIG. 10E show populations of cells (THP-1 monocyte cells) treated with a first pulse label of EdU (20 μM) and a second pulse label of BrdU (10 μm) as detected by flow cytometry. FIG. 10A is divided into four quadrants with the first quadrant (Q1) located in the upper left hand corner, the second quadrant (Q2) located in the upper right hand corner, the third quadrant (Q3) located in the lower left hand corner, and the fourth quadrant (Q4) located in the lower right hand corner. Populations of cells in quadrant Q3 (lower left, colored dark green) are negative for both EdU (first pulse) and BrdU (second pulse). Populations of cells in quadrant Q2 (upper right, colored dark blue) are positive for both EdU (first pulse) and BrdU (second pulse). Populations of cells in quadrant Q1 (upper left, colored light green) are positive for BrdU and negative for EdU, a sub-population of BrdU-positive cells which are EdU-negative, this sub-population being the population of cells entering S-phase after the Edu only incorporation. Populations of cells in Q4 (lower right, colored red) are positive for EdU and negative for BrdU, a sub-population of EdU-positive cells (late-stage S) which are BrdU-negative, this sub-population being the population of cells leaving S-phase before the BrdU-incorp. FIG. 10B is a graph of BrdU vs. DNA content showing these same colored populations from FIG. 10A. FIG. 10C is a graph of EdU vs DNA content showing these same colored populations from FIG. 10A. FIGS. 10D and 10E show single parameter histograms for each EdU (FIG. 10D) with the P3 marker showing the positive events for EdU; and BrdU (FIG. 10E) with the P2 marker showing the positive events for BrdU.

Example 14

A standard method of preparing cultured cells for the measurement of newly synthesized DNA (cellular proliferation) is set up according to known conditions for cells to be actively growing by providing the proper media and nutrient requirements. In the present example, Jurkat T-cell lymphocyte cell cultures were diluted one to four to a density of 2×10$^5$ cells/ml. The cultures were treated with a cell cycle blocking agent, colchicine, which stops proliferation at the G2M stage of the cell cycle, at concentrations of 0, 32 nM, 75 nM, 125 nM, 250 nM, 500 nM and 1 μM for 18 hours. To each condition, the first nucleoside analog, EdU, was then added at 10 μM, a concentration appropriate for incorporation in the DNA of cells undergoing DNA synthesis. The cells were grown in the presence of EdU for one hour. The cells were then centrifuged to pellet the cells and remove the media with blocking agent, and cells had replacement of fresh media. The cell cultures were allowed to recover for two hours before an appropriate amount of the second nucleoside analog, BrdU, was added at a 10 μM concentration, and the cells were grown for one hour. The cells were then harvested, washed, fixed with 70% ice-cold ETOH and stored at 4° C. until use. The cells were then washed and resuspended in 4M HCL for 20 minutes at room temperature. A phosphate/critric acid buffer was added, and the cells washed twice and resuspended in 0.1% TritonX/1% BSA/PBS at 1×10$^7$/ml. Then, labeling of the EdU was performed by adding click chemistry based reagents, including a solution comprised of $CuSO_4$ in Tris-buffered saline and Alexa Fluor® 647-azide (650 nm excitation maxima/670 nm emission maxima) (Molecular Probes™/Invitrogen™, Carlsbad, Calif.). The cells were then washed with 0.1% TritonX/1% BSA/PBS. After this, labeling of the BrdU was performed using the anti-BrdU antibody FITC conjugate (494 nm excitation maxima/518 nm emission maxima) (Exalpha Biologicals, Inc., Maynard Calif.). To detect DNA content, a nucleic acid dye, DAPI (358 nm excitation maxima/461 nm emission maxima) (Molecular Probes™/Invitrogen™, Carlsbad, Calif.) was added. Detection of the three labels was performed by flow cytometry. To detect the BrdU label, 488 nm excitation was used, with a 530/30 nm bandpass. To detect the EdU label, 633 nm excitation was used, with a 660/20 nm bandpass. To detect DNA content, 355 nm excitation was used, with a 450/50 nm bandpass.

FIG. 11 shows the percentage of cells which are EdU and BrdU co-positive (Q2), EdU and BrdU co-negative (Q3), BrdU positive and EdU negative (Q1), and BrdU negative and EdU positive (Q4) of the seven different treatment conditions. The control, which has no colchicine blocker added shows proliferation as detected by both EdU and BrdU pulses. All of the concentrations of colchicine treated cells shows decreased proliferation with both pulses of EdU and BrdU, as expected. If there were some cell recovery during the two hours after the removal of the colchicine, the BrdU percentage is expected to increase. However, there is no recovery seen at any colchicine concentration after the first EdU pulse from the removal of the colchicine treatment, as seen by the second pulse of BrdU.

Figures 1A, 12:
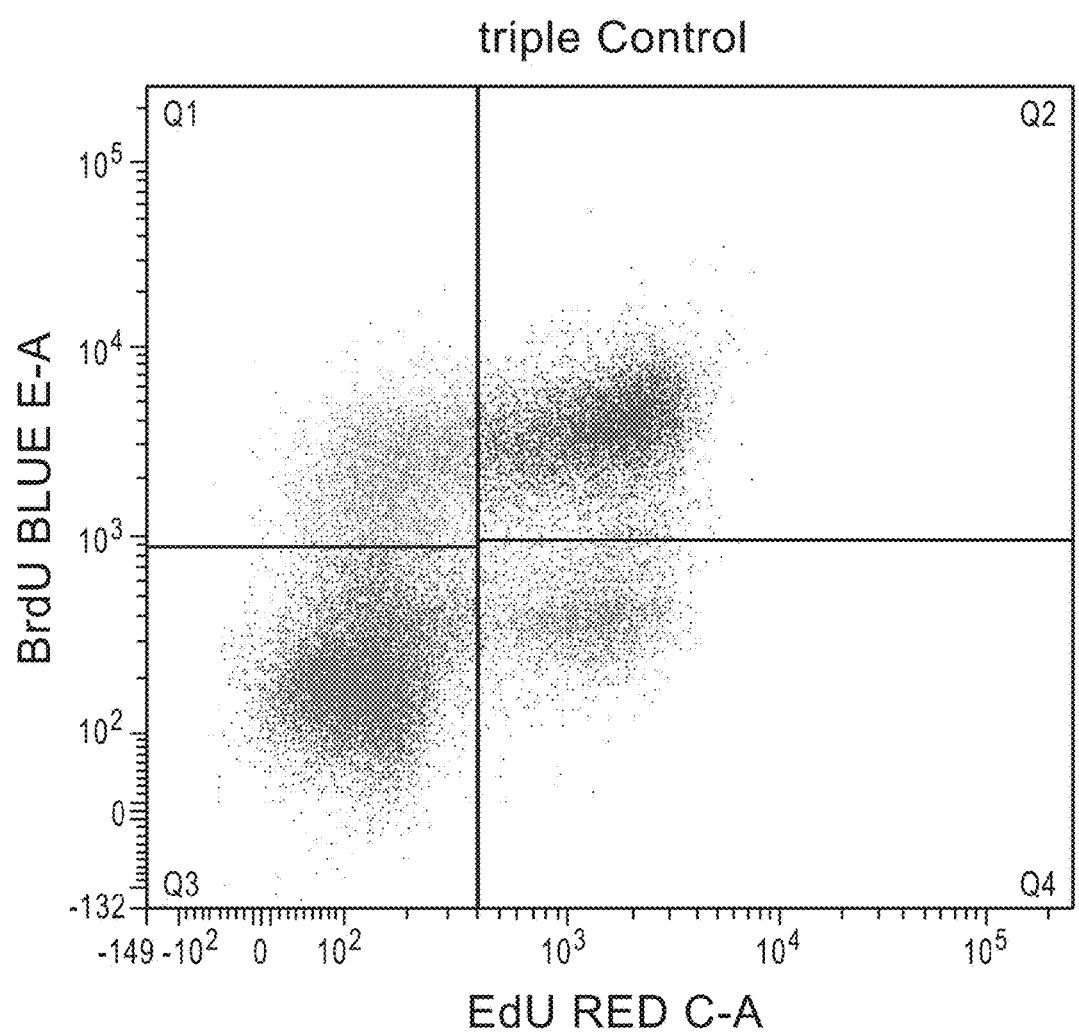
Figures 1B, 12:
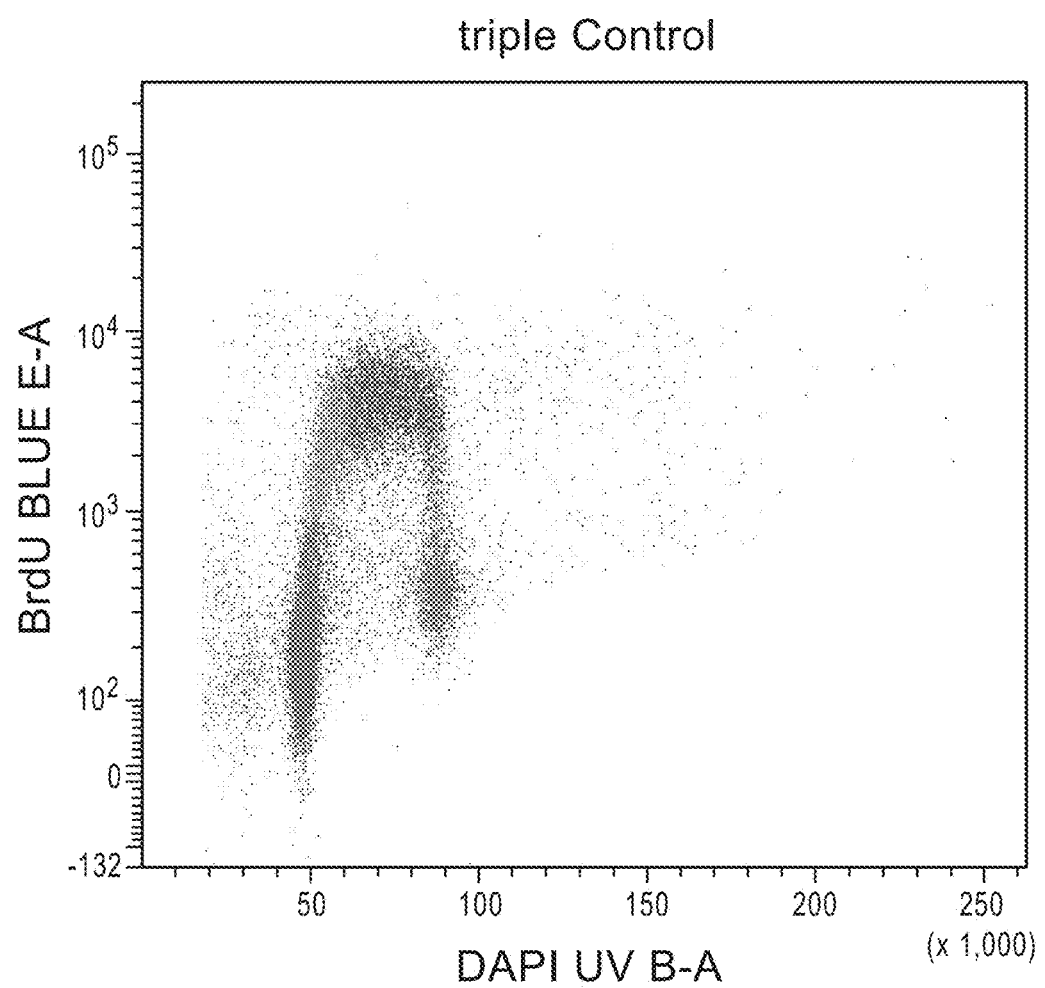
Figures 1C, 12:
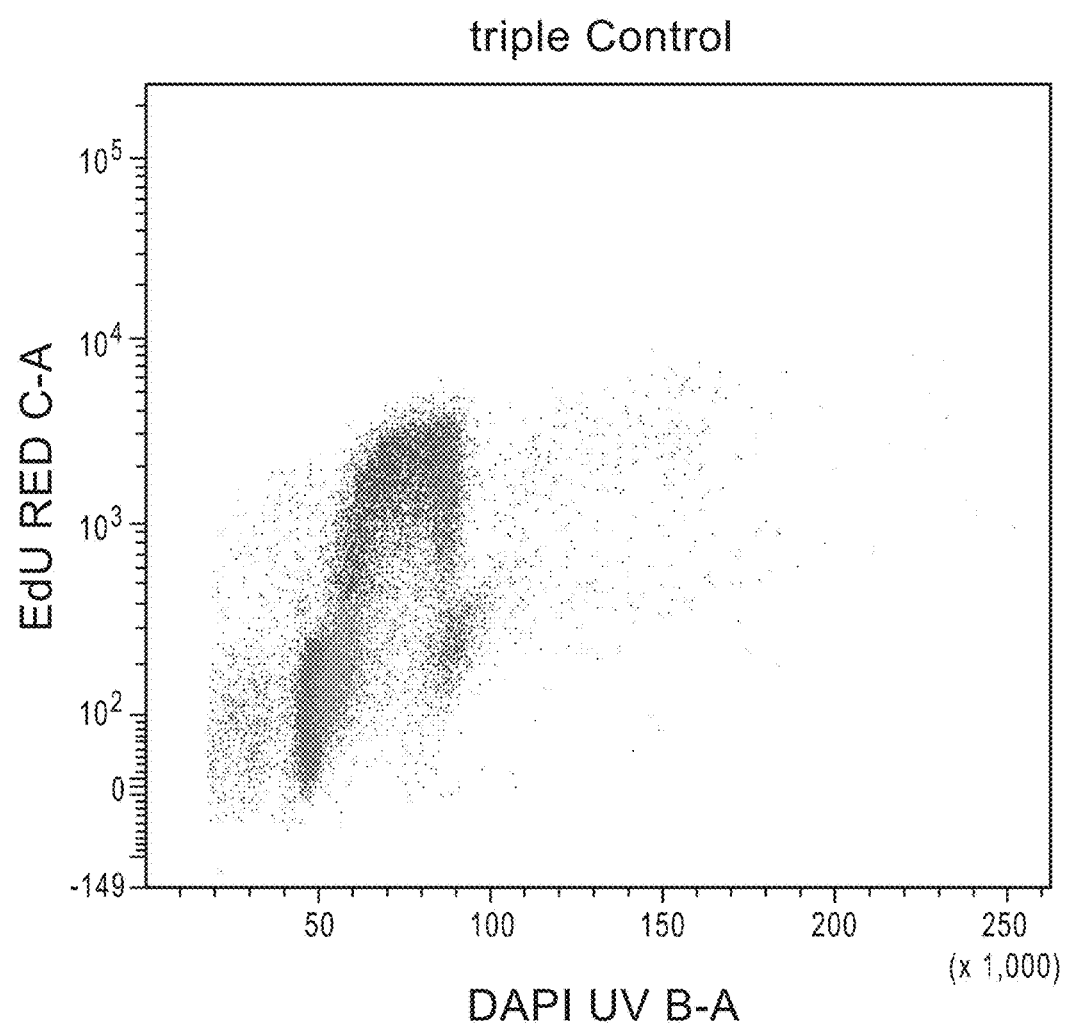
Figures 1D, 12:
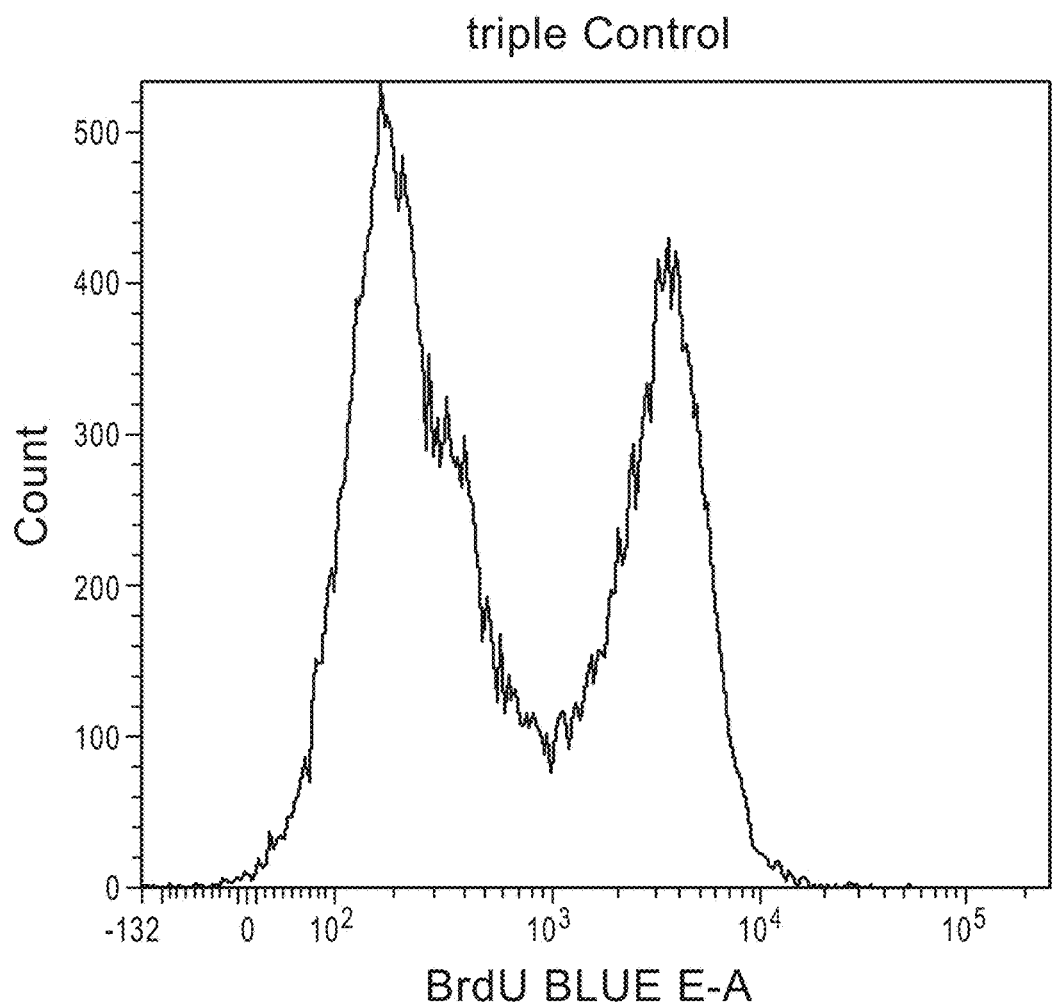
Figures 1E, 12:
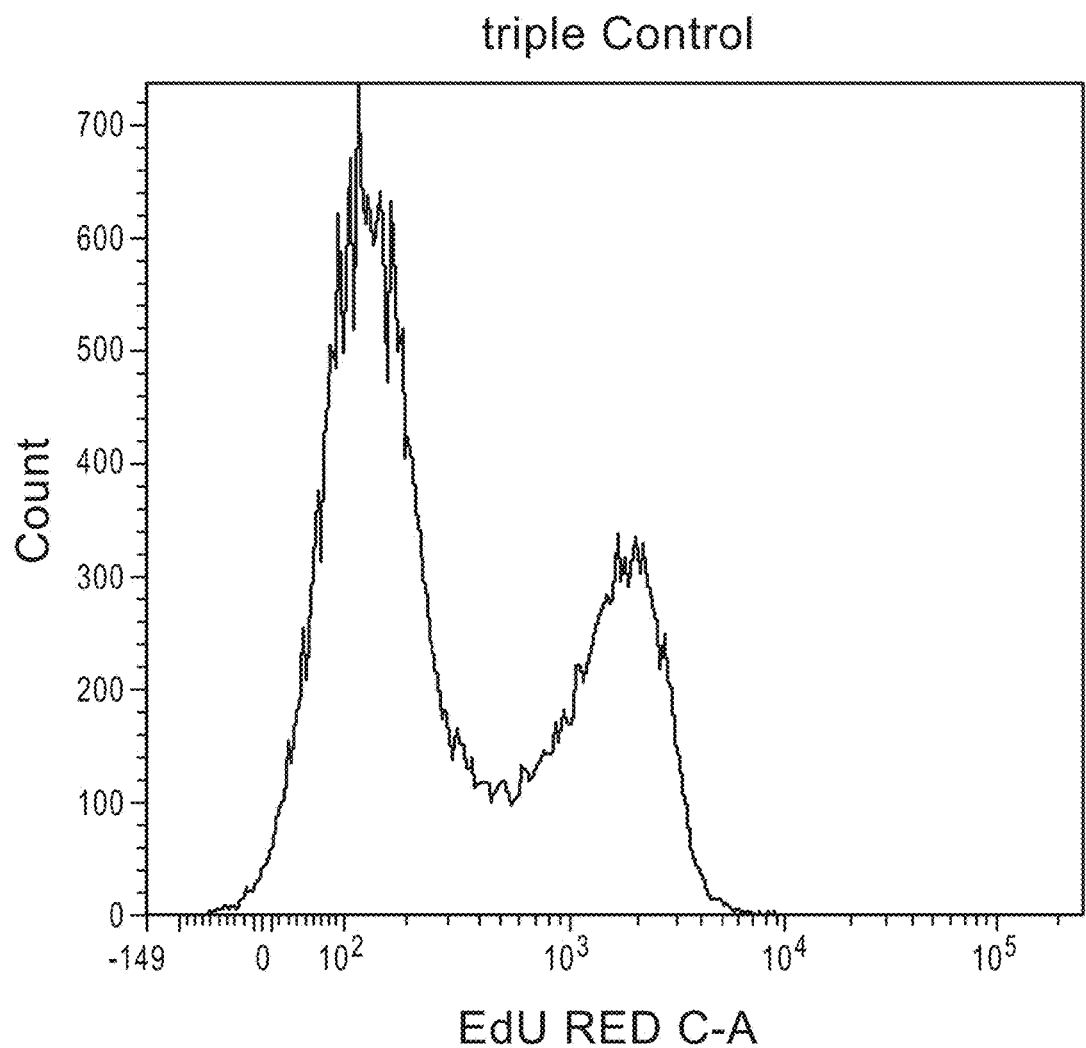
Figures 2F, 12:
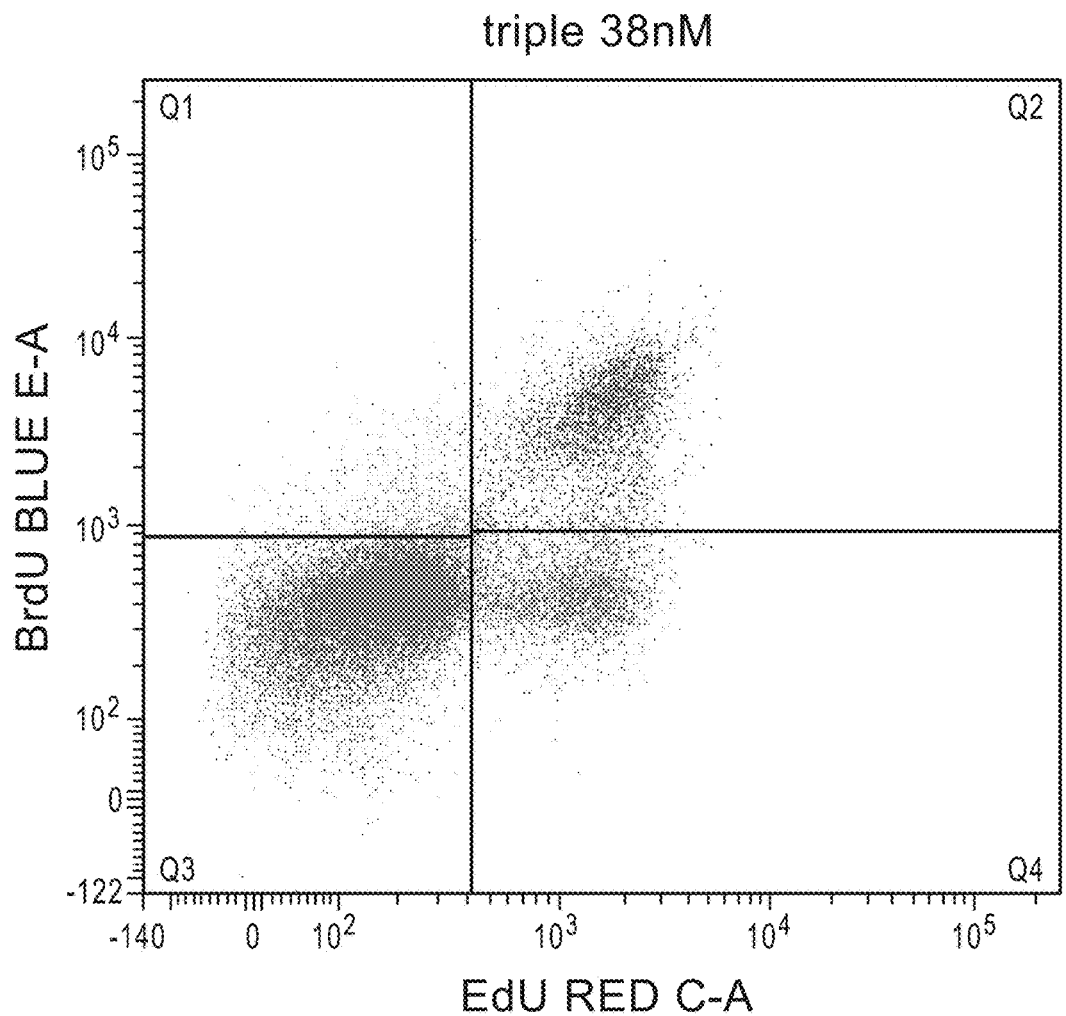
Figures 2G, 12:
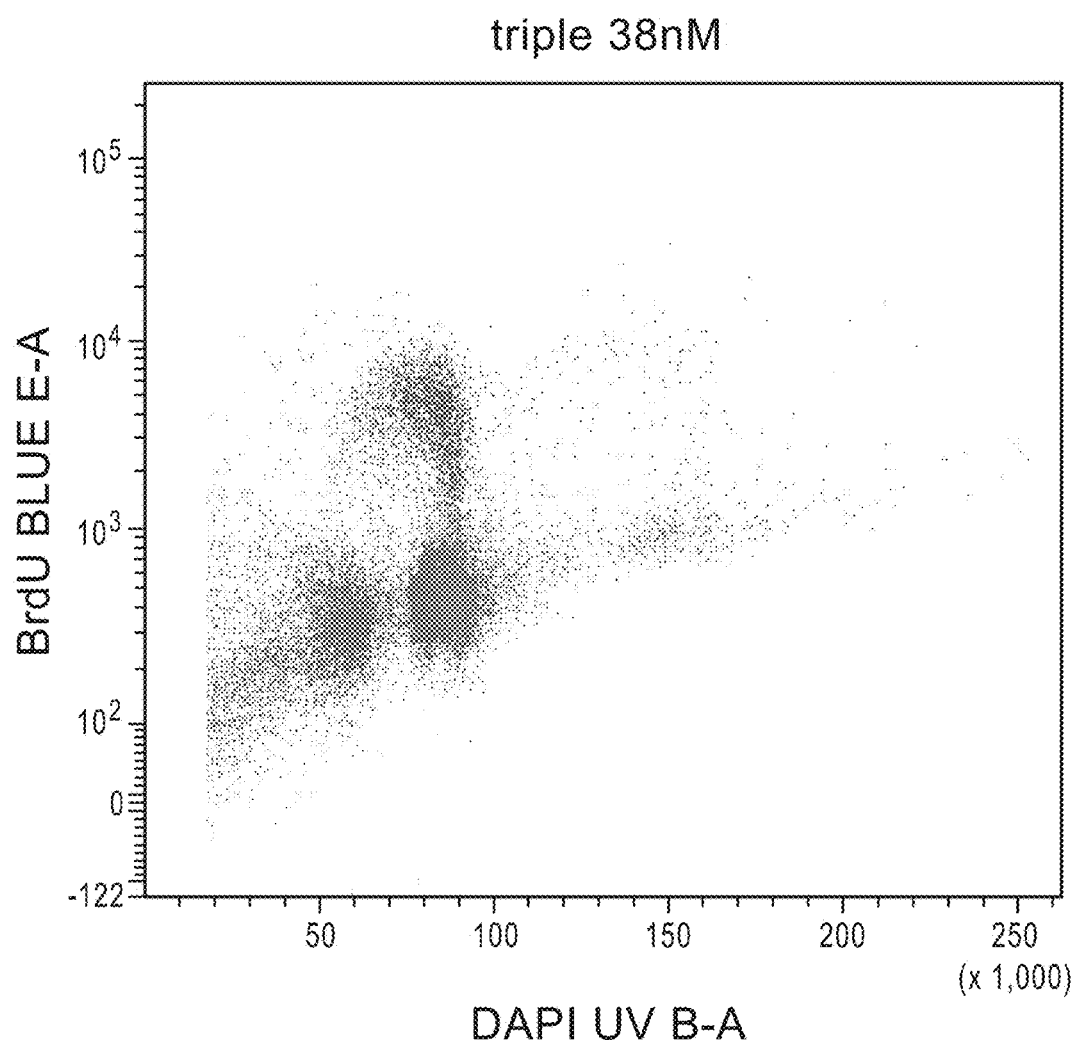
Figures 2H, 12:
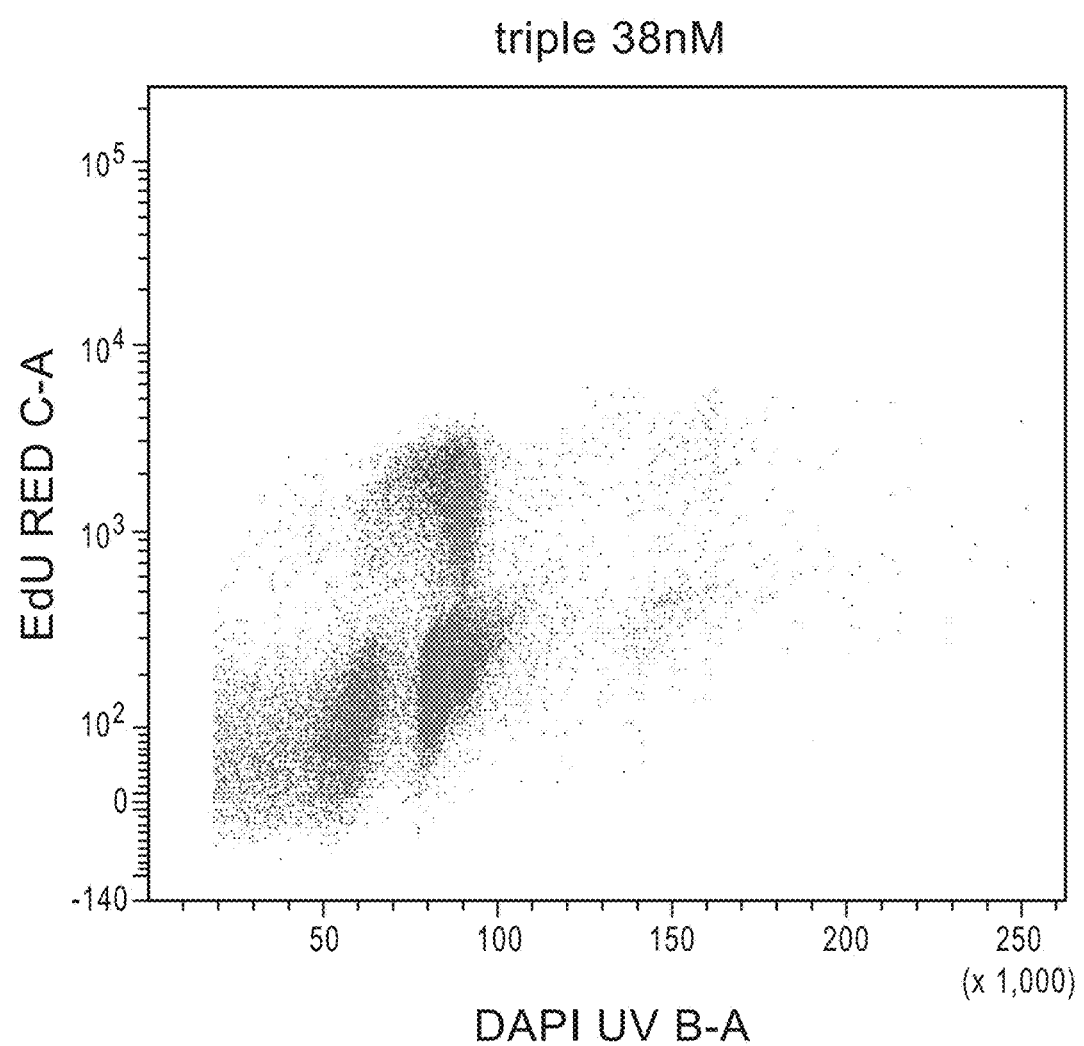
Figures 2I, 12:
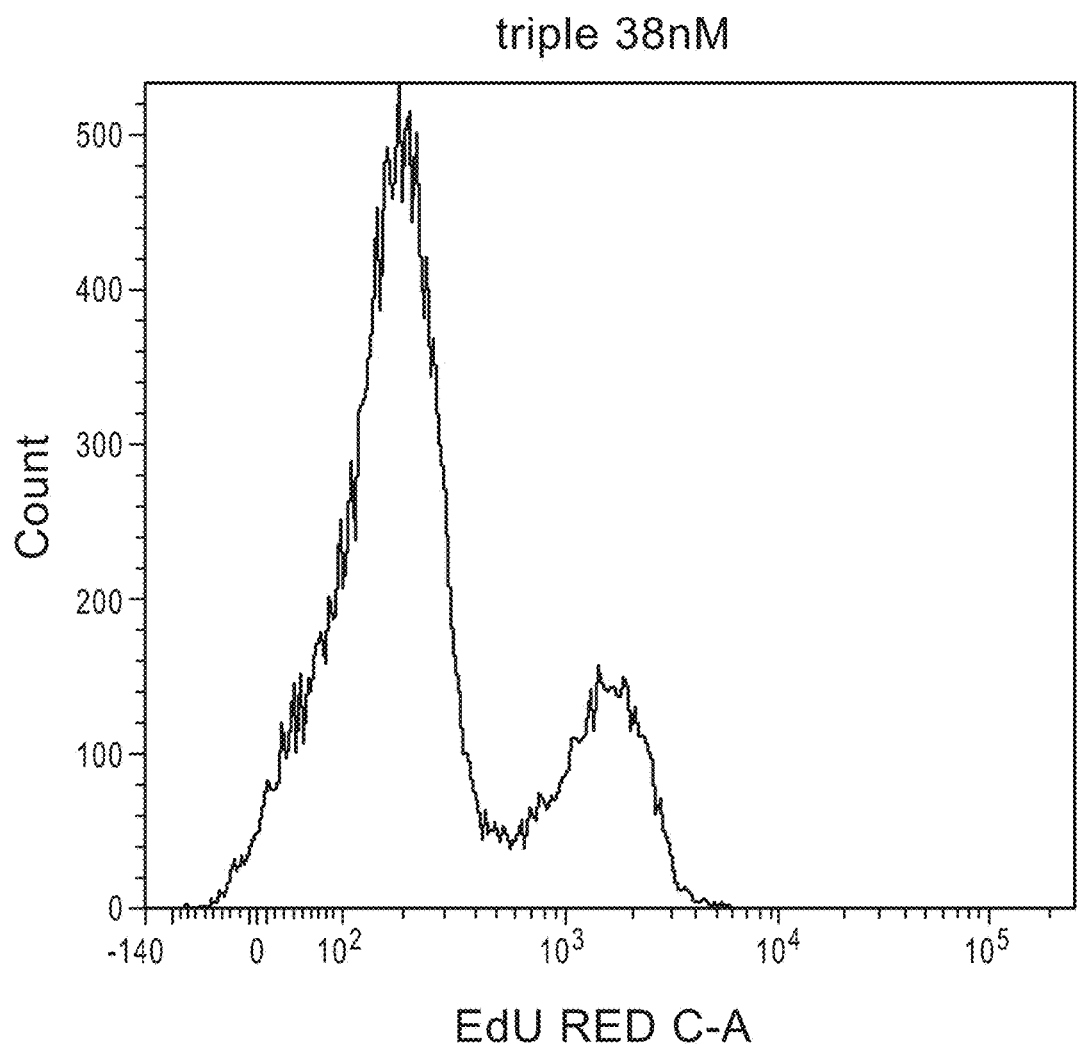
Figures 2J, 12:
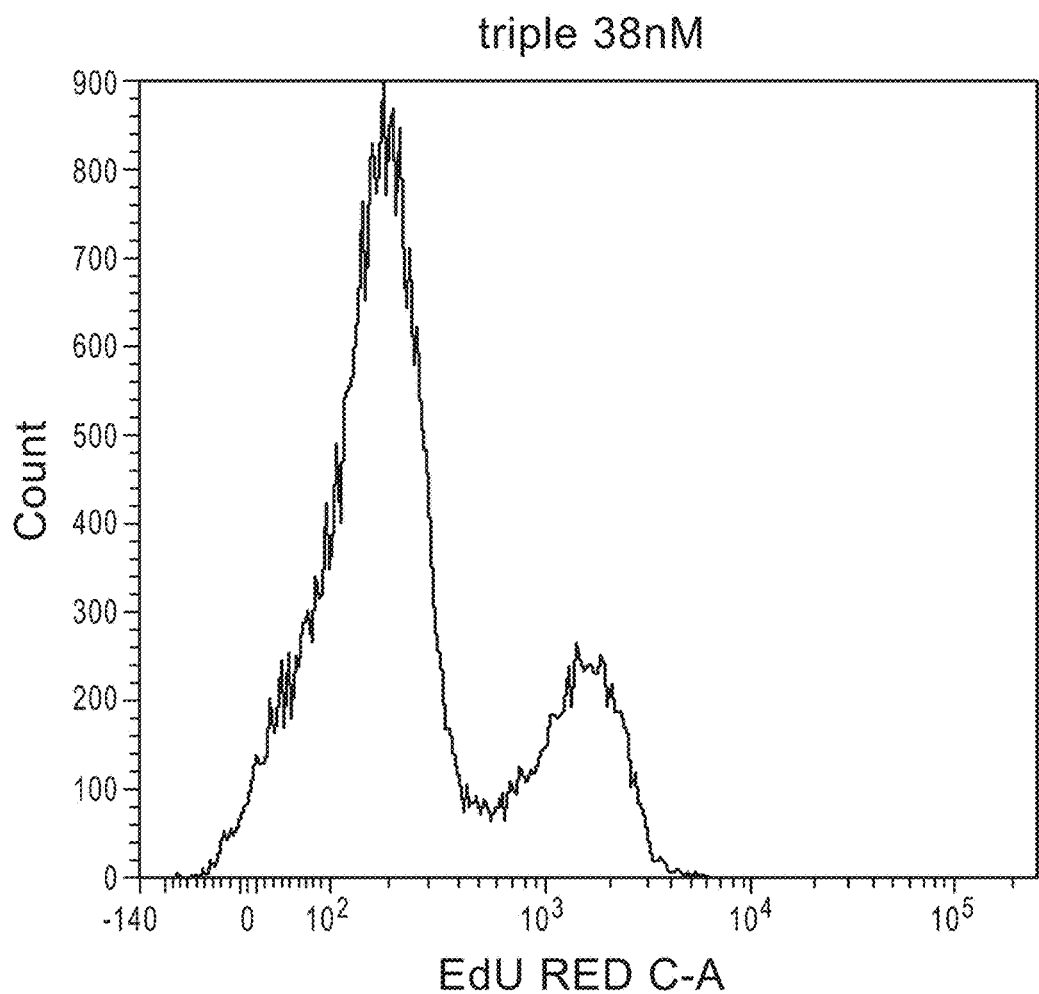

A series of result graphs labeled FIGS. 12-1A, 12-1B, 12-1C, 12-1D, 12-1E, 12-2F, 12-2G, 12-2H, 12-2I and 12-2J show populations of cells treated with a first pulse label of EdU (20 μM) and a second pulse label of BrdU (10 μm) as detected by flow cytometry. FIGS. 12-1A through 12-1E represent the control cells untreated with colchicine, and FIGS. 12-2F through 12-2J represent cells treated with 32 nM colchicine for 18 hours before the first pulse. Dual parameter graphs FIGS. 12-1A and 12-2F are divided into four quadrants with the first quadrant (Q1) located in the upper left hand corner, the second quadrant (Q2) located in the upper right hand corner, the third quadrant (Q3) located in the lower left hand corner, and the fourth quadrant (Q4) located in the lower right hand corner. Populations of cells in quadrant Q3 (lower left, colored light blue) are negative for both EdU (first pulse) and BrdU (second pulse). Populations of cells in quadrant Q2 (upper right, colored dark blue) are positive for both EdU (first pulse) and BrdU (second pulse). Populations of cells in quadrant Q1 (upper left, colored light green) are positive for BrdU and negative for EdU, a sub-population of BrdU-positive cells which are EdU-negative, this sub-population being the population of cells entering S-phase after the EdU only incorporation. Populations of cells in Q4 (lower right, colored red) are positive for EdU and negative for BrdU, a sub-population of EdU-positive cells (late-stage S) which are BrdU-negative, this sub-population being the population of cells leaving S-phase before the BrdU-incorp. FIGS. 12-1B and 12-2G are graphs of BrdU vs. DNA, FIGS. 12-1C and 12-2H are graphs of EdU vs DNA content showing these same colored populations FIGS. 12-1A and 12-2F. FIGS. 12-1D and 12-2I show single parameter histograms for BrdU with two populations of cells distinguishable, those cells which are positive for BrdU and those cells which are negative for BrdU. FIGS. 12-1E and 12-2J show single parameter histograms for EdU with two populations of cells distinguishable, those cells which are positive for EdU and those cells which are negative for EdU. The control graphs (FIGS. 12-1A through 12-1E) show higher EdU and BrdU positive events, the expected proliferation for the cells, than the graphs from the cells treated with 32 nM colchicine (FIGS. 12-2F through 12-2J), which show decreased proliferation as expected with the blocker treatment.

What is claimed is:

1. A method for measuring a change in cellular DNA synthesis:
   a) incubating a sample with an effective amount of a first nucleoside or nucleotide analog comprising an ethynyl group to form a primary incubated sample,
      wherein the first nucleoside or nucleotide analog is ethynyl-deoxyuracil (EdU);
   b) incubating the primary incubated sample with a second nucleoside or nucleotide analog comprising a halogen moiety to form a secondary incubated sample,
      wherein the second nucleoside or nucleotide analog is BrdU, and wherein the first nucleoside or nucleotide analog is not incorporated into a DNA polymer when the second nucleoside or nucleotide analog is present;
   c) incubating the secondary incubated sample with a first labeling reagent comprising an azide group that can undergo a [3+2] cycloaddition reaction with the ethynyl group of the first nucleoside or nucleotide analog and a second labeling reagent that is an antibody that binds to the second nucleoside or nucleotide analog to form a labeled sample; and
   d) detecting the labeled sample wherein a level of incorporation of the first nucleoside or nucleotide analog is measured and allows establishment of a baseline rate of the cellular DNA synthesis and a level of incorporation of the second nucleoside or nucleotide analog is measured,
      wherein a difference between the level of incorporation of the second nucleoside or nucleotide analog relative to the baseline rate indicates a change in cellular DNA synthesis,
      with the proviso that there is no wash step prior to adding the second nucleoside or nucleotide analog.

2. A method for measuring a change in cellular nucleic acid synthesis:
   a) incubating a sample with an effective amount of a first nucleoside or nucleotide analog comprising an ethynyl group to form a primary incubated sample,
      wherein the first nucleoside or nucleotide analog is ethynyl-deoxyuracil (EdU);
   b) incubating the primary incubated sample with a second nucleoside or nucleotide analog comprising a halogen moiety to form a secondary incubated sample,
      wherein the second nucleoside or nucleotide analog is BrdU, and wherein the first nucleoside or nucleotide analog is not incorporated into a nucleic acid polymer when the second nucleoside or nucleotide analog is present;
   c) incubating the secondary incubated sample with a first labeling reagent comprising an azide group that can undergo a [3+2] cycloaddition reaction with the ethynyl group of the first nucleoside or nucleotide analog and a second labeling reagent that is an antibody that binds to the second nucleoside or nucleotide analog to form a labeled sample; and
   d) detecting the labeled sample wherein a level of incorporation of the first nucleoside or nucleotide analog is measured and allows establishment of a baseline rate of the cellular nucleic acid synthesis and a level of incorporation of the second nucleoside or nucleotide analog is measured,
      wherein a difference between the level of incorporation of the second nucleoside or nucleotide analog relative to the baseline rate indicates a change in cellular nucleic acid synthesis,
      with the proviso that there is no wash step prior to adding the second nucleoside or nucleotide analog.

3. The method according to claim 2 wherein the sample is treated with a test compound simultaneous to or before treatment with the second nucleoside or nucleotide analog.

4. The method according to claim 2, wherein the first labeling reagent or the second labeling reagent comprises a fluorescent dye.

5. The method according to claim 2, wherein the antibody is an anti-BrdU antibody.

6. The method according to claim 2, wherein the first labeling reagent is a dye-labeled azide.

7. The method according to claim 2, wherein incorporation of said first nucleoside analog and said second nucleoside analog is detected by flow cytometry.

8. The method according to claim 2, wherein incorporation of said first nucleoside analog and said second nucleoside analog is detected by fluorescence microscopy.

9. The method according to claim 2, wherein the sample is an organism or cells in cell culture.

* * * * *